US009921165B2

(12) United States Patent
Bailey et al.

(10) Patent No.: US 9,921,165 B2
(45) Date of Patent: Mar. 20, 2018

(54) OPTICAL ANALYTE DETECTION SYSTEMS AND METHODS OF USE

(75) Inventors: Ryan C. Bailey, Urbana, IL (US); Abraham J. Qavi, Champaign, IL (US); Jared T. Kindt, Champaign, IL (US); Ji-Yeon Byeon, Daejeon (KR); Matthew S. Luchansky, Champaign, IL (US); Melinda S. McClellan, Champaign, IL (US); Adam L. Washburn, Savoy, IL (US); Tate Owen, Del Mar, CA (US); Martin Anthony Gleeson, San Diego, CA (US); Lawrence C. Gunn, III, Encinitas, CA (US)

(73) Assignees: Genalyte, Inc., San Diego, CA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/883,280

(22) PCT Filed: Nov. 4, 2011

(86) PCT No.: PCT/US2011/059454
§ 371 (c)(1),
(2), (4) Date: May 2, 2013

(87) PCT Pub. No.: WO2012/061778
PCT Pub. Date: May 10, 2012

(65) Prior Publication Data
US 2013/0295688 A1 Nov. 7, 2013

Related U.S. Application Data
(60) Provisional application No. 61/410,595, filed on Nov. 5, 2010, provisional application No. 61/452,796, filed on Mar. 15, 2011.

(51) Int. Cl.
*G01N 21/00* (2006.01)
*G01N 21/75* (2006.01)
(Continued)

(52) U.S. Cl.
CPC .......... *G01N 21/75* (2013.01); *C12Q 1/6804* (2013.01); *C12Q 1/6825* (2013.01);
(Continued)

(58) Field of Classification Search
CPC ............... G01N 21/7746; G01N 21/41; G01N 2201/0873; G01N 33/54373;
(Continued)

(56) References Cited

U.S. PATENT DOCUMENTS

| 4,474,893 A | 10/1984 | Reading |
| 4,714,681 A | 12/1987 | Reading |

(Continued)

FOREIGN PATENT DOCUMENTS

| CA | 2 355 816 | 6/2000 |
| CA | 2 555 962 | 9/2007 |

(Continued)

OTHER PUBLICATIONS

European Search Report dated Mar. 31, 2014 of corresponding European Patent Application No. 11838918.8—10 pages.
(Continued)

*Primary Examiner* — Erik B Crawford
(74) *Attorney, Agent, or Firm* — Knobbe, Martens, Olson & Bear, LLP

(57) ABSTRACT

Various embodiments are drawn to systems and methods for detecting an analyte of interest in a sample including an optical sensor, a capture probe attached to a surface of the optical sensor wherein the capture probe is capable of binding to the analyte to form a duplex or complex, and an antibody capable of binding to the analyte, duplex, or
(Continued)

complex. In several embodiments, systems and methods further include a particle attached to the antibody or capable of binding to the antibody. In several embodiments, systems and methods for analyte detection feature one or more of the following: high detection sensitivity and specificity, scalability and multiplex capacity, ability to analyze large analytes, and ability to detect or measure multiple individual binding events in real-time.

21 Claims, 39 Drawing Sheets

(51) Int. Cl.
*C12Q 1/68* (2018.01)
*G01N 33/543* (2006.01)
*G01N 21/77* (2006.01)

(52) U.S. Cl.
CPC ... *G01N 21/7746* (2013.01); *G01N 33/54373* (2013.01); *G01N 2021/7789* (2013.01)

(58) Field of Classification Search
CPC ........ G01N 33/54393; C12Q 2522/101; C12Q 2563/131; C12Q 1/6804; C12Q 1/6816; G02B 6/29338
USPC ........... 356/128, 337, 481; 385/12; 435/6.11
See application file for complete search history.

(56) References Cited

U.S. PATENT DOCUMENTS

| | | | |
|---|---|---|---|
| 4,925,648 A | 5/1990 | Hansen et al. | |
| 5,270,163 A | 12/1993 | Gold et al. | |
| 5,475,096 A | 12/1995 | Gold et al. | |
| 5,478,755 A | 12/1995 | Attridge et al. | |
| 5,539,082 A | 7/1996 | Nielsen et al. | |
| 5,567,588 A | 10/1996 | Gold et al. | |
| 5,573,920 A | 11/1996 | Randle | |
| 5,595,877 A | 1/1997 | Gold et al. | |
| 5,601,819 A | 2/1997 | Wong et al. | |
| 5,637,459 A | 6/1997 | Burke et al. | |
| 5,681,702 A | 10/1997 | Collins et al. | |
| 5,683,867 A | 11/1997 | Biesecker et al. | |
| 5,705,337 A | 1/1998 | Gold et al. | |
| 5,714,331 A | 2/1998 | Buchardt et al. | |
| 5,719,262 A | 2/1998 | Buchardt et al. | |
| 5,939,021 A | 8/1999 | Hansen et al. | |
| 6,043,060 A | 3/2000 | Imanishi | |
| 6,210,891 B1 | 4/2001 | Nyren et al. | |
| 6,268,490 B1 | 7/2001 | Imanishi et al. | |
| 6,583,399 B1 | 6/2003 | Hunziker et al. | |
| 7,083,920 B2 | 8/2006 | Werner et al. | |
| 7,391,936 B2 | 6/2008 | Pau et al. | |
| 7,528,403 B1 | 5/2009 | Borselli et al. | |
| 7,778,499 B2 | 8/2010 | Janz et al. | |
| 7,796,262 B1* | 9/2010 | Wang et al. ................. 356/436 |
| 2002/0012930 A1 | 1/2002 | Rothberg et al. | |
| 2002/0037526 A1 | 3/2002 | Tashiro et al. | |
| 2003/0017579 A1 | 1/2003 | Corn et al. | |
| 2003/0027327 A1 | 2/2003 | Cunningham et al. | |
| 2003/0039978 A1 | 2/2003 | Hannah | |
| 2003/0096302 A1 | 5/2003 | Yguerabide et al. | |
| 2003/0153023 A1* | 8/2003 | Starzl et al. ................. 435/7.92 |
| 2004/0023396 A1* | 2/2004 | Boyd ................. G01N 21/7746 385/12 |
| 2004/0145752 A1 | 7/2004 | Angeley | |
| 2004/0180362 A1* | 9/2004 | Lazar et al. ................. 435/6 |
| 2004/0191765 A1 | 9/2004 | Mozdy | |
| 2005/0014179 A1 | 1/2005 | Karlsson et al. | |
| 2005/0250094 A1 | 11/2005 | Storhoff et al. | |
| 2006/0087656 A1 | 4/2006 | Barford | |
| 2006/0119859 A1 | 6/2006 | Su et al. | |
| 2006/0182659 A1 | 8/2006 | Unlu et al. | |
| 2006/0194232 A1 | 8/2006 | Turner et al. | |
| 2006/0215165 A1 | 9/2006 | Melman | |
| 2006/0256350 A1 | 11/2006 | Nolte et al. | |
| 2007/0081163 A1 | 4/2007 | Liang et al. | |
| 2007/0147732 A1* | 6/2007 | Sanders ................. B82Y 20/00 385/32 |
| 2007/0237460 A1 | 10/2007 | Fan et al. | |
| 2008/0026394 A1 | 1/2008 | Labgold et al. | |
| 2008/0038738 A1 | 2/2008 | Weigum et al. | |
| 2008/0129997 A1* | 6/2008 | Yi et al. ................. 356/337 |
| 2008/0131939 A1 | 6/2008 | Roper | |
| 2008/0138801 A1 | 6/2008 | He | |
| 2008/0160622 A1 | 7/2008 | Su et al. | |
| 2008/0204760 A1 | 8/2008 | Gollier et al. | |
| 2009/0170212 A1 | 7/2009 | Van Dijk et al. | |
| 2009/0309049 A1 | 12/2009 | Van Dijk et al. | |
| 2010/0009456 A1 | 1/2010 | Prins et al. | |
| 2010/0105566 A1 | 4/2010 | Bieniarz et al. | |
| 2010/0124787 A1* | 5/2010 | Nitkowski ......... G01N 21/7746 436/164 |
| 2010/0165351 A1 | 7/2010 | Xu et al. | |
| 2011/0045472 A1 | 2/2011 | Gunn, III | |
| 2011/0275061 A1 | 11/2011 | Weidemaier et al. | |
| 2012/0092650 A1 | 4/2012 | Gunn, III et al. | |
| 2013/0157283 A1 | 6/2013 | Yung et al. | |
| 2013/0261010 A1 | 10/2013 | Bailey et al. | |
| 2014/0070082 A1 | 3/2014 | Guo et al. | |
| 2014/0273029 A1 | 9/2014 | Bailey et al. | |

FOREIGN PATENT DOCUMENTS

| | | |
|---|---|---|
| EP | 0740156 A1 | 10/1996 |
| EP | 2347247 | 7/2011 |
| EP | 2635710 | 9/2013 |
| EP | 2825885 | 1/2015 |
| JP | 2924707 | 7/1999 |
| JP | 2002-526773 | 8/2002 |
| JP | 2004-354068 | 12/2004 |
| JP | 2004-361087 | 12/2004 |
| JP | 2005-140683 | 6/2005 |
| JP | 2005-321244 | 11/2005 |
| JP | 2006-029883 | 2/2006 |
| JP | 2006-153643 | 6/2006 |
| JP | 2006-267052 | 10/2006 |
| JP | 2007-309886 | 11/2007 |
| JP | 2008-057997 | 3/2008 |
| JP | 2010-518394 | 5/2010 |
| JP | 2012-507035 | 3/2012 |
| JP | 5656853 | 12/2014 |
| WO | WO 91/000360 | 1/1991 |
| WO | WO 92/000509 | 1/1992 |
| WO | WO 92/005793 | 4/1992 |
| WO | WO 92/008802 | 5/1992 |
| WO | WO 93/017715 | 9/1993 |
| WO | WO 98/039352 | 9/1998 |
| WO | WO 99/014226 | 3/1999 |
| WO | WO 00/020861 | 4/2000 |
| WO | WO 00/056746 | 9/2000 |
| WO | WO 00/056748 | 9/2000 |
| WO | WO 00/066604 | 11/2000 |
| WO | WO 01/000641 | 1/2001 |
| WO | WO 01/001455 | 1/2001 |
| WO | WO 03/052097 | 6/2003 |
| WO | WO 2005/066612 A2 | 7/2005 |
| WO | WO 2005/080602 A2 | 9/2005 |
| WO | WO 2007/081163 | 7/2007 |
| WO | WO 2008/054170 | 5/2008 |
| WO | WO 2008/081719 | 7/2008 |
| WO | WO 2008/097199 | 8/2008 |
| WO | WO 2009/069009 A1 | 6/2009 |
| WO | WO 2009/075473 A1 | 6/2009 |
| WO | WO 2009/076323 A2 | 6/2009 |
| WO | WO 2009/076323 A3 | 6/2009 |
| WO | WO 2010/062627 A2 | 6/2010 |
| WO | WO 2011/091037 A2 | 7/2011 |
| WO | WO 2012/061778 A2 | 5/2012 |

(56) References Cited

FOREIGN PATENT DOCUMENTS

WO  WO 2013/138251 A1  9/2013
WO  WO 2014/143637 A   9/2014

OTHER PUBLICATIONS

Office Action dated Mar. 10, 2015 in corresponding European Application No. 11838918.8, 4 pgs.
Office Action dated Oct. 13, 2015 in corresponding European Application No. 11838918.8, 4 pgs.
International Search Report dated Jun. 16, 2010 for International Patent Application No. PCT/US2009/062268.
International Search Report and Written Opinion dated May 24, 2013 in corresponding PCT Application No. PCT/US2013/030274.
International Preliminary Report on Patentability and Written Opinion dated May 3, 2011 for International Patent Application No. PCT/US2009/062268.
International Search Report and Written Opinion dated Jun. 16, 2014 in Application No. PCT/US2014/026852, filed Mar. 13, 2014.
International Search Report and Written Opinion dated Jun. 1, 2012 in Application No. PCT/US2011/59454, 22pgs.
Office Action dated Jan. 14, 2014 in corresponding Japanese Application No. 2011-534688, 20 pgs.
Decision to Grant dated Sep. 24, 2014 in corresponding Japanese Application No. 2011-534688, 3 pgs.
Office Action dated Oct. 20, 2015 in corresponding Japanese Application No. 2014-238245, 3 pgs.
International Written Opinion dated May 26, 2009 in Application No. PCT/US2008/085988, 4 pgs.
Bailey er al. A Robust Silicon Phtotonic Platform for Multiparameter Biological Analysis. Proc. Of SPIE. 2009, vol. 7220, p. 72200N-6. (Table of Conents for Proc. Of SPIE. 2009, vol. 7220 uploaded to establish priority and avialable from <http://spie.org/x648.html?product_id=799296&origin_id=x4325&start_volume_number=7200&end_volume_number=7299&start at=21>) esp: abstract, p. 72200N-4 first paragraph; p. 72200N-2 top of page; p. 72200N-3 first paragraph; Figs, 5, 6, 7.
Frank Vollmer, et al. Multiplexed DNA Qualification by Spectoscopic Shift of Two Microsphere Cavities, Biophysical Journal, Sep. 2003, vol. 85, pp. 1974 to 1979. See pp. 1974 to 1977.
Kajiura M et al: "Biosensing by optical waveguide spectroscopy based on localized surface plasmon resonance of gold nanoparticles used as a probe or as a label", Journal of Colloid and Interface Science, Academic Press, New York, NY, US, vol. 335, No. 1, Jul. 1, 2009 (Jul. 1, 2009), pp. 140-145.
Matthew S. Luchansky et al: "Silicon Photonic Microring Resonators for Quantitative Cytokine Detection and T-Cell Secretion Analysis", Analytical Chemistry, vol. 82, No. 5, Mar. 1, 2010 (Mar. 1, 2010), pp. 1975-1981.
Matthew S. Luchansky et al: "Sensitive on-chip detection of a protein biomarker in human serum and plasma over an extended dynamic range using silicon photonic microring resonators and sub-micron beads", Lab on a Chip, vol. 11, No. 12, Jan. 1, 2011 (Jan. 1, 2011), p. 2042.
A. Ramachandran, et al. A Universal Biosensing platform Based on Optical Micro-rin resonators, Biosensors and Bioelectronics, Sep. 21, 2007, vol. 23, pp. 939 to 944. Se abstract, pp. 940 to 942.
Rachel McKendry, et al. Multiple Label-Free Biodetection and Quantative DNA-Binding assays on Nanomechanical Cantilever Array, PNAS, Jul. 23, 2002, vol. 99, No. 15, paged 9783 to 9788. See pp. 9783 to 9785.
Song et al. "Detection of Oligonucleotide Hybridization at Femtomolar Level and Sequence-Specific gene analysis of the *Arabidopsis thaliana* Leaf Extract with an Unltrasensitive Surface Plasmon Resonance Spectrometer" Nucleic Acids Research, 2002, 30(14): e72, pp. 1-11.
Abraham J. Qavi et al: "Anti-DNA:RNA Antibodies and Silicon Photonic Microring Resonators: Increased Sensitivity for Multiplexed micro RNA Detection", Analytical Chemistry, vol. 83, No. 15, Aug. 1, 2011 (Aug. 1, 2011), pp. 5949-5956.
Z. Li, et al. Sequence-Specific Label Free DNA Sensors Based on Silicon Nanowires, Nano Lett., Aug. 1, 2004, vol. 4, No. 2, pp. 245 to 247. See pp. 246-247.
Allen et al., "Nuclear factor-kappaB-related serum factors as longitudinal biomarkers of response and survival in advanced oropharyngeal carcinoma," Clin. Cancer Res. 13(11): 3182-3190, (2007).
Anderson et al., "The human plasma proteome: history, character, and diagnostic prospects," Mol. Cell. Proteomics, 1: 845-867, (2002).
Angelopoulos et al., "Cytokines in Alzheimer's disease and vascular dementia," Int. J. Neurosci., 118(12): 1659-1672, (2008).
Anoop et al., "CSF Biomarkers for Alzheimer's Disease Diagnosis," Int. J. Alzheimers Dis., 2010: 1-12, (2010).
Azevedo et al., "Stability of free and immobilised peroxidase in aqueous-organic solvents mixtures," J. Mol. Catal. B: Enzym., 15: 147-153, (Nov. 2001).
Baker et al., "Plasma and cerebrospinal fluid interleukin-6 concentrations in posttraumatic stress disorder," Neuroimmunomodulation, 9(4): 209-217, (2001).
Bell et al., "Interleukin-6 and interleukin-10 in cerebrospinal fluid after severe traumatic brain injury in children," J. Neurotrauma, 14: 451-457, (1997).
Blennow et al., "Cerebrospinal fluid and plasma biomarkers in Alzheimer disease," Nat Rev Neurol, 6(3): 131-144, (2010).
Blum-Degen et al., "Interleukin-1 beta and interleukin-6 are elevated in the cerebrospinal fluid of Alzheimer's and de novo Parkinson's disease patients," Neurosci. Lett., 202(1-2): 17-20, (1995).
Boguslawski et al., "Characterization of monoclonal antibody to DNA.RNA and its application to immunodetection of hybrids," J. Immunological Methods, 89(1): 123-130, (1986).
Braasch et al., "Novel antisense and peptide nucleic acid strategies for controlling gene expression," Biochemistry, 41(14): 4503-4510, (2002).
Byeon et al., "Efficient bioconjugation of protein capture agents to biosensor surfaces using aniline-catalyzed hydrazone ligation," Langmuir, 26(19): 15430-15435, (2010).
Byeon et al., "Multiplexed evaluation of capture agent binding kinetics using arrays of silicon photonic microring resonators," Analyst, 136(17): 3430-3433, (2011).
Capule et al., "An ELISA-based method to quantify the association of small molecules with aggregated amyloid peptides," Anal. Chem., 84(3): 1786-1791, (2012).
Casebolt et al., "Monoclonal Antibody Solution Hybridization Assay for Detection of Mouse Hepatitis Virus Infection," Journal of Clinical Microbiology, 30(3): 608-612, (1992).
Chen et al., "Plasmon-Enhanced Colorimetric ELISA with Single Molecule Sensitivity," Nano Lett., 11(4): 1826-1830, (2011).
Clark et al., "Characteristics of the microplate method of enzyme-linked immunosorbent assay for the detection of plant viruses," J. Gen. Virol., 34: 475-483, (1977).
Conyers et al., "Chromogenic substrates for horseradish peroxidase," Anal. Biochem., 192: 207-211, (1991).
Ellison et al., "Standard additions: myth and reality," Analyst, 133: 992-997, (2008).
Engelborghs et al., "Unchanged levels of interleukins, neopterin, interferon-gamma and tumor necrosis factor-alpha in cerebrospinal fluid of patients with dementia of the Alzheimer type," Neurochem. Int., 34: 523-530, (1999).
"EnzMet TM HRP Detection Kit for IHC / ISH", Nanoprobes Inc., Yaphank, NY, Jan. 2008. http://www.nanoprobes.com/products/EnzMet-SISH-enzyme-metallography-for-ISH-and-IHC.html, downloaded Jan. 19, 2017.
Fagan et al., "Cerebrospinal fluid biomarkers of Alzheimer's disease," Biomarkers Med., 4(1): 51-63, (2010).
Fliss et al., "Anti-DNA.RNA antibodies: an efficient tool for non-isotopic detection of *Listeria* species through a liquid-phase hybridization assay," Appl Microbiol Biotechnol, 43(4): 717-724, (1995).

(56) References Cited

OTHER PUBLICATIONS

Fortin et al., "Imaging of DNA hybridization on microscopic polypyrrole patterns using scanning electrochemical microscopy (SECM): the HRP bio-catalyzed oxidation of 4-chloro-1-naphthol," Analyst, 131: 186-193, (2006).
Gabay, "Interleukin-6 and chronic inflammation," Arthritis Res. Ther., 8(Suppl 2): S3, 6 pp., (2006).
Gauldie et al., "Interferon beta 2/B-cell stimulatory factor type 2 shares identity with monocyte-derived hepatocyte-stimulating factor and regulates the major acute phase protein response in liver cells," Proc. Natl. Acad. Sci. U.S.A., 84(20): 7251-7255, (1987).
Gorris et al., "Mechanistic Aspects of Horseradish Peroxidase Elucidated through Single-Molecule Studies," Am. Chem. Soc., 131(17): 6277-6282, (2009).
Hansson et al., "Association between CSF biomarkers and incipient Alzheimer's disease in patients with mild cognitive impairment: a follow-up study," Lancet Neurol, 5(3): 228-234, (2006).
Heath et al., "Nanotechnology and Cancer," Annu. Rev. Med., 59: 251-265, (2008).
Hosoda et al., "A comparison of chromogenic substrates for horseradish peroxidase as a label in steroid enzyme immunoassay," Chem. Pharm. Bull. (Tokyo), 34: 4177-4182, (1986).
Huell et al., "Interleukin-6 is present in early stages of plaque formation and is restricted to the brains of Alzheimer's disease patients," Acta Neuropath., 89(6): 544-551, (1995).
Ihenetu et al., Pharmacological characterisation of cannabinoid receptors inhibiting interleukin 2 release from human peripheral blood mononuclear cells, European Journal of Pharmacology 454 (2003) 207-215.
Iqbal et al., "Label-Free Biosensor Arrays Based on Silicon Ring Resonators and High-Speed Optical Scanning Instrumentation," IEEE J. Sel. Top. Quantum Electron., 16(3): 654-661, (2010).
Ivanov et al., "Chip-Based Nanostructured Sensors Enable Accurate Identification and Classification of Circulating Tumor Cells in Prostate Cancer Patient Blood Samples," Anal. Chem., 85(1): 398-403, (2013).
Jia et al., "Cerebrospinal fluid tau, Aβ1-42 and inflammatory cytokines in patients with Alzheimer's disease and vascular dementia," Neurosci. Lett., 282: 12-16, (2005).
Khuseyinova et al., "Determination of C-reactive protein: comparison of three high-sensitivity immunoassays," Clin. Chem., 49: 1691-1695, (2003).
Kindt et al., "Chaperone probes and bead-based enhancement to improve the direct detection of mRNA using silicon photonic sensor arrays," Anal. Chem., 84(18): 8067-8074, (2012).
Kindt J.T. et al., "Subpicogram Per Milliliter Detection of Interleukins Using Silicon Photonic Microring Resonators and an Enzymatic Signal Enhancement Strategy," Anal Chem 85: 10653-10657 (2013).
Konry et al., "Microsphere-based rolling circle amplification microarray for the detection of DNA and proteins in a single assay," Anal. Chem., 81(14): 5777-5782, (2009).
Kostelny et al., "Formation of a bispecific antibody by the use of leucine zippers," J. Immunol., 148(5): 1547-1553, (1992).
Krishnan et al., "Attomolar detection of a cancer biomarker protein in serum by surface plasmon resonance using superparamagnetic particle labels," Agnew Chem. Int. Ed. Engl., 50: 1175-1178, (Feb. 2011).
Lafer et al., "The effect of anti-Z-DNA antibodies on the B-DNA-Z-DNA equilibrium," J Biol Chem, 261(14): 6438-6443, (1986).
Li et al., "Detection of protein biomarkers using RNA aptamer microarrays and enzymatically amplified surface plasmon resonance imaging," Anal. Chem., 79(3): 1082-1088, (2007).
Llano et al., "Cerebrospinal fluid cytokine dynamics differ between Alzheimer disease patients and elderly controls," Alzheimer Dis. Assoc. Disord., 26(4): 322-328, (2012).
Luchansky et al., "Rapid, multiparameter profiling of cellular secretion using silicon photonic microring resonator arrays," J. Am. Chem. Soc., 133(50): 20500-20506, (2011).
Supplemental Materials for Luchansky, M.S., et al. "Sensitive on-chip detection of a protein biomarker in human serum and plasma over an extended dynamic range using silicon photonic microring resonators and sub-micron beads," The Royal Society of Chemistry (Supp): 1-14 (2011).
Martinez et al., "Increased cerebrospinal fluid fas (Apo-1) levels in Alzheimer's disease. Relationship with IL-6 concentrations," Brain Res., 869(1-2): 216-219, (2000).
Marz et al., "Interleukin-6 (IL-6) and soluble forms of IL-6 receptors are not altered in cerebrospinal fluid of Alzheimer's disease patients," Neurosci. Lett., 239(1): 29-32, (1997).
Munge et al., "Nanostructured immunosensor for attomolar detection of cancer biomarker interlukin-8 using massively labeled supermagnetic particles," Agnew Chem. Int. Ed. Engl., 50(34): 7915-7918, (Aug. 2011).
Nielsen et al., "Sequence-selective recognition of DNA by strand displacement with a thymine-substituted polyamide," Science, 254(5037): 1497-1500, (1991).
Olson et al., "Growth factors and cytokines/chemokines as surrogate biomarkers in cerebrospinal fluid and blood for diagnosing Alzheimer's disease and mild cognitive impairment," Exp. Gerontol., 45(1): 41-46, (2010).
Palandra et al., "Highly specific and sendsitive measurements of human and monkey interleukin 21 using sequential protein and tryptic peptide immunoaffinity LC-MS/MS," Anal. Chem., 85(11): 5522-5529, (2013).
Parker et al., Monoclonal Antibodies against the Human Epidermal Growth Factor Receptor from A431 Cells, The Journal of Biological Chemistry, 259(15), 9906-9912, 1984.
Riley et al., "Stability of DNA/anti-DNA complexes. II. Salt lability and avidity," J Immunol, 124(1): 1-7, (1980).
Rissin et al., "Single-molecule enzyme-linked immunosorbent assay detects serum proteins at subfemtomolar concentrations," Nat. Biotechnol., 28: 595-599, (2010).
Sheehan et al., "Detection limits for nanoscale biosensors," J. Nano Lett., 5: 803-807, (2005).
Sokolova et al., "Monocyte Chemoattractant Protein-1 Plays a Dominant Role in the Chronic Inflammation Observed in Alzheimer's Disease," Brain Pathol., 19(3): 392-398, (2009).
Soleymani et al., "Hierarchical Nanotextured Microelectrodes Overcome the Molecular Transport Barrier to Achieve Rapid, Direct Bacterial Detection," ACS Nano, 5(4): 3360-3366, (2011).
Squires et al., "Making it stick: convection, reaction and diffusion in surface-based biosensors," Nat. Biotechnol., 26(4): 417-426, (2008).
Steensberg et al., "Cerebrospinal fluid IL-6, HSP72, and TNF-alpha in exercising humans," Brain Behav. Immun., 20(6): 585-589, (2006).
Stelmasiak et al., "Interleukin-6 concentration in serum and cerebrospinal fluid in multiple sclerosis patients," Med. Sci. Monit., 6(6): CR1104-CR1108, (2000).
Stollar et al., "Immunochemical approaches to gene probe assays," Anal. Biochem., 161(2): 387-394, (1987).
Stollar, "Molecular analysis of anti-DNA antibodies," FASEB J, 8(3): 337-342, (1994).
Tarkowski et al., "Early intrathecal production of interleukin-6 predicts the size of brain lesion in stroke," Stroke, 26: 1393-1398, (1995).
Tarkowski et al., "Intracerebral production of tumor necrosis factor-alpha, a local neuroprotective agent, in Alzheimer disease and vascular dementia," J. Clin. Immunol., 19(4): 223-230, (1999).
Tsai et al., "Cerebrospinal fluid interleukin-6, prostaglandin E2 and autoantibodies in patients with neuropsychiatric systemic lupus erythematosus and central nervous system infections," Scand. J. Rheumatol., 23(2): 57-63, (1994).
Tutt et al., "Trispecific F(ab')3 derivatives that use cooperative signaling via the TCR-CD3 complex and CD2 to activate and redirect resisting cytotoxic T cells," J. Immunol., 147(1): 60-69, (1991).
Vandermeeren et al., "Detection of Proteins in Normal and Alzheimer's Disease Cerebrospinal Fluid with a Sensitive Sandwich Enzyme-Linked Immunosorbent Assay," Journal of Neurochemistry, 61(5): 1828-1834, (1993).

(56) References Cited

OTHER PUBLICATIONS

Veitch, "Horseradish peroxidase: a modern view of a classic enzyme," Phytochemistry, 65(3): 249-259, (2004).
Vollmer et al., "Whispering-gallery-mode biosensing: label-free detection down to single molecules," Nature Methods, 5: 591-596, (2008).
Wang et al., "Cyclohexene Nucleic Acids (CeNA): Serum Stable Oligonucleotides that Activate RNase H and Increase Duplex Stability with Complementary RNA," J. Am. Chem. Soc., 122(36): 8595-8602, (2000).
Washburn et al., "Label-free quantitation of a cancer biomarker in complex media using silicon photonic microring resonators," Anal. Chem. 81(22): 9499-9506, (2009).
eBioscience Enzyme Linked Immunosorbent Assay 2010, ELISA Protocols, http://www.ebioscience.com/media/pdf/best-protocols/enzyme-linked-immunosorbent-assay-elisa.pdf.
SABiosciences Single Analyte ELISA Kits 2010, Product List, http://www.sabiosciences.com/singleelisa.php.
Elia, G; Silacci, M; Scheurer, S; Scheuermann, J; Neri, 0 Affinity-capture reagents for protein arrays. Trends Biotech. 2002, 20, S19-S22.
Phelan, M L; Nock, S Generation of bioreagents for protein chips. Proteomics 2003, 3, 2123-2134.
Brody, EN; Gold, L Aptamers as therapeutic and diagnostic agents. J. Biotechol. 2000, 74,5-13.
Kodadek, T; Reddy, M M; Olivos, H J; Bach hawat-Si kder, K; Alluri, P G Synthetic Molecules as Antibody Replacements. Acc. Chem. Res. 2004,37,711-718.
Engvall, E; Perlmann, P Enzyme-linked immunosorbent assay (ELISA) quantitative assay for immunoglobulin G. Immunochem 1971, 8,871-874.
http://www.luminexcorp.com/.
Kodadek, T Protein microarrays: prospects and problems. Chem. Biot. 2001, 8, 105-115.
Sun, Y S; Landry, J P; Fei, Y Y; Zhu, X 0; Luo, J T; Wang, X B; Lam, K S Effect of Fluorescently Labeling Protein Probes on Kinetics of Protein-Ligand Reactions. Langmuir 2008, 24, 13399-13405.
Qavi, A J; Washburn, A L; Byeon, J-Y; Bailey, R C Label-free technologies for quantitative multiparameter biological analysis. Anal. Bioanal. Chem. 2009, 394, 121-135.
Homola, J; Vee, S S; Gauglitz, G Surface plasmon resonance sensors: review. Sens. Actuators B. 1999, 54,3-15.
Stuart, 0 A; Haes, A J; Yonzon, C R; Hicks, E M; Van Duyne, R P Biological Applications of Localized Surface Plasmon Resonance Phenomena. IEEE Proc.—Nanobiotechnol.2005, 152, 13-32.
Bailey, R C; Parpia, M; Hupp, J T Sensing via Optical Interference. Materials Today 2005, 8, 46-52.
Wolfbeis, 0 S Fiber-Optic Chemical Sensors and Biosensors. Anal. Chem. 2002, 74, 2663-2678.
Boozer, C; Kim, G; Cong, S; Guan, H; Londergan, T Looking towards label-free biomolecular interaction analysis in a high-throughput format: a review of new surface plasmon resonance technologies. Curro Op. Biotech. 2006, 17, 400-405.
Vahala, K J Optical microcavities. Nature 2003, 424, 839-846.
Luchansky, M S; Washburn, A L; Martin, T A; Iqbal, M; Gunn, L C; Bailey, R C Characterization of the evanescent field profile and bound mass sensitivity of a label-free silicon photonic microring resonator biosensing platform. Biosens. Bioelectron.2010, doi:1 0.1016/j.bios.201 0.1 007.1 010.
Washburn, A L; Luchansky, M S; Bowman, A L; Bailey, R C Quantitative Multiplexed Detection of Five Protein Biomarkers Using Arrays of Silicon Photonic Microring Resonators. Anal. Chem. 2010, 82,69-72.
Eddowes, M J Direct immunochemical sensing: basic chemical principles and fundamental limitations. Biosensors 1987, 3, 1-15.
Byeon, J-Y; Bailey, R C Label-Free, Multiplexed Determination of Aptamer and Antibody Capture Agent Binding Affinities Using Silicon Photonic Microring Resonator Arrays and Implications for Sensitive Biomolecule Detection. Chem. Commun., 136, 3430-3433, 2011.

Qavi, A J; Mysz, T M; Bailey, R C Label-Free Detection of DNA and Isothermal Discrimination of Single Nucleotide Polymorphisms via Kinetic Desorption Rates using Silicon Photonic Microring Resonator Arrays. J. Am. Chem. Soc. 6827-6833, 2011.
Qavi, A J; Bailey, R C Multiplexed Detection and Label-Free Quantitation of MicroRNAs Using Arrays of Silicon Photonic Microring Resonators. Angew. Chem. 2010, 49,4608-4611.
Wolter, A; Niessner, R; Seidel, M Preparation and Characterization of Functional Poly(ethylene glycol) Surfaces for the Use of Antibody Microarrays. Anal. Chem. 2007, 79,4529-4537.
Ladd, J; Zhang, Z; Chen, S; Hower, J C; Jiang, S Zwitterionic Polymers Exhibiting High Resistance to Nonspecific Protein Adsorption from Human Serum and Plasma. Biomacromolecules 2008, 9, 1357-1361.
Soderberg, 0; Leuchowius, K-J; Kamali-Moghaddam, M; Jarvius, M; Gustafsdottir, S; Schall meiner, E; Gullberg, M; Jarvius, J; Landegren, U Proximity Ligation: A Specific and Versatile Tool for the Proteomic Era. Genetic Eng. 2007, 28, 85-93.
Gulberg, M; Fredriksson, S; Taussig, M; Jarvius, J; Gustafsdottir, S; Landegren, U A sense of closeness: protein detection by proximity ligation. Curro Op. Biotech. 2003, 14, 82-86.
Heyduk, E; Dummit, B; Chang, Y-H; Heyduk, T Molecular Pincers: Antibody-Based Homogeneous Protein Sensors. Anal. Chem. 2008, 80,5152-5159.
Reddy, M M; Bachhawat-Sikder, K; Kodadek, T Transformation of Low-Affinity Lead Compounds into High-Affinity Protein Capture Agents. Chem. Biol. 2004, 11, 1127-1137.
Agnew, H D; Rohde, R D; Millward, S W; Nag, A; Yeon, W-S; Hein, J; Pitram, S M; A.A., T; Burns, V M; Krom, R J; Fokin, V V; Sharpless, K B; Heath, J R Iterative In Situ Click Chemistry Creates Antibody-like Protein-Capture Agents. Angew. Chern. 2009, 48,4944-4948.
Krasinski, A; Radic, Z; Manetch, R; Raushel, J; Taylor, P; Sharpless, K B; Kolb, H C In Situ Selection of lead Compounds by Click Chemistry: Target-Guided Optimization of Acetylcholinesterase Inhibitors. J. Arn. Chern. Soc. 2005, 127, 6686-6692.
Manetsch, R; Krasinski, A; Radic, Z; Raushel, J; Taylor, P; Sharpless, K B; Kolb, H C In Situ Click Chemistry: Enzyme Inhibitors Made to Their Own Specifications. J. Arn. Chern. Soc. 2004, 126, 12809 12818.
Erlanson, D A; lam, J W; Wiesmann, C; luong, T N; Simmons, R I; Delano, W I; Choong, I C; Burdett, M T; Flanagan, W M; lee, D; Gordon, E M; O'Brien, T In situ assembly of enzyme inhibitors using extended tethering. Nature Biotech. 2003, 21, 308-314.
Bachhawat-Sikder, K; Kodadek, T Mixed-Element Capture Agents: A Simple Strategy for the Construction of Synthetic, High-Affinity Protein Capture Ligands. J. Arn. Chern. Soc. 2003, 125,9550-9551.
Naffin, J I; Han, Y; Olivos, H J; Reddy, M M; Sun, T; Kodadek, T Immobilized Peptides as High-Affinity Capture Agents for Self-Associating Proteins. Chern. Biol. 2003, 10, 251-259.
Niemeyer, C M Semisynthetic DNA-Protein Conjugates for Biosensing and Nanofabrication. Angew. Chern. Inti. Ed. 2010, 49, 1200-1216.
Bailey, R C; Kwong, G A; Radu, C G; Witte, 0 N; Heath, J R DNA-Encoded Antibody Libraries: A Unified Platform for Multiplexed Cell Sorting and Detection of Genes and Proteins. J. Arn. Chern. Soc. 2007, 129, 1959-1967.
Ge, Y. Turner, A P F Molecularly Imprinted Sorbent Assays: Recent Developments and Applications. Chern. Eur. J. 2009, 15, 8100-8107.
Scheck, R A; Francis, M B Regioselective Labeling of Antibodies through N-Terminal Transamination. ACS Chern. Biol. 2007, 2, 247-251.
Niemeyer, C M; Adler, M; Wacker, R Detecting antigens by quantitative immuno-PCR. Nature Protocols 2007, 2, 1918-1930.
Bayley, H; Cremer, P S Stochastic sensors inspired by biology. Nature 2001, 413, 226-230.
Thaxton, C S; Rosi, N L; Mirkin, C A Optically and chemically encoded nanoparticie materials for DNA and protein detection. MRS Bulletin 2005, 30, 376-380.
Palik, E, Ed. Handbook of Optical Constants of Solids; Academic Press: San Diego, CA,1998.

(56) References Cited

OTHER PUBLICATIONS

Bailey, R C; Nam, J-M; Mirkin, C A; Hupp, J T Real-Time Multicolor DNA Detection with Chemoresponsive Diffraction Gratings and Nanoparticle Probes. J. Am. Chem. Soc. 2003, 125, 13541-13547.

Hao, E; Li, S; Bailey, R C; Zou, S; Schatz, G C; Hupp, J T The Optical Properties of Metal Nanoshells. J. Phys. Chem. B. 2004, 108, 1224-1229.

Hao, E; Bailey, R C; Hupp, J T; Schatz, G C; Li, S Synthesis and Optical Properties of 'Three-Pointed' Star-Shaped Gold Nanoparticles. Nano. Lett. 2004, 4, 327-330.

Bailey, R C; Hupp, J T Large-Scale Resonance Amplification of Optical Sensing of Volatile Compounds with Chemoresponsive Visible-Region Diffraction Gratings. J. Am. Chem. Soc. 2002, 124, 6767-6774.

Fang, W.; Bucholz, D.B.; Bailey, R.C.; Hupp, J.T.; Chang, R.P.H.; Cao, H. Detection of Chemical Species Using Ultraviolet Microdisk Lasers. Appl. Phys. Lett. 2004, 85, 3666-3668.

Krioukov, E.; Klunder, D.J.W.; Driessen, A; Greve, J.; Otto, C. Sensor based on an integrated optical microcavity. Opt. Lett. 2002, 27, 512-514.

Vollmer, F.; Braun, D.; Libchaber, A; Khoshima, M.; Teraoka, I.; Arnold, S. Protein detection by optical shift of a resonant microcavity. Appl. Phys. Lett. 2002, 80, 4057-4059.

Chao, C.-Y.; Guo, L.J. Biochemical sensors based on polymer microrings with sharp asymmetrical resonances. Appl. Phys. Lett. 2003, 83, 1527-1529.

Schmidt, J. Stochastic sensors. J. Mater. Chem. 2005, 15,831-840.

Bayley, H.; Martin, C.R. Resistive-Pulse Sensing—From Microbes to Molecules. Chem. Rev. 2000, 100, 2575-2594.

Armani, A.M.; Kulkarni, R.P.; Fraser, S.E.; Flagan, R.C.; Vahala, K.J. Label-free single-molecule detection with optical microcavities. Science 2007, 317,783-787.

Perez-Luna, V.H.; O'Brien, M.J.; Opperman, K.A.; Hampton, P.O.; Lopez, G.P.; Klumb, L.A.; Stayton, P.S. Molecular Recognition between Genetically Engineered Streptavidin and Surface-Bound Biotin. J. Am. Chem. Soc. 1999, 121,6469-6478.

Berezovski, M.; Nutiu, R.; Li, Y.; Krylov, S.N. Affinity Analysis of a Protein-Aptamer Complex Using Nonequilibrium Capillary Electrophoresis of Equilibrium Mixtures. Anal. Chem. 2003, 75, 1382-1386.

Wayment, J.R.; Harris, J.M. Controlling Binding Site Densities on Glass Surfaces. Anal. Chem. 2006, 78,7841-7849.

Pierres, A.; Touchard, D.; Benoliel, A.-M.; Bongrand, P. Dissecting Steptavidin-Biotin Interaction with a Laminar Flow Channel. Biophys. J. 2002, 82, 3214-3223.

Cao, L.; Chen, H.-Z.; Zhu, L.; Zhang, X.-B.; Wang, M. Optical absorption and structural studies of erbium biphthalocyanine sublimed films. Mater. Lett. 2003, 57, 4309-4314.

Su, X.-C.; Huber, T.; Dixon, N.E.; Otting, G. Site-Specific Labelling of Proteins with a Rigid-Lanthanide-Binding Tag. ChemBioChem 2006, 7, 1599-1604.

Turner, E.H.; Cohen, D.; Pugsley, H.R.; Gomez, D.G.; Whitmore, C.D.; Zhu, C.; Dovichi, N.J. Chemical cytometry: the chemical analysis of single cells. Anal. Bioanal. Chem. 2008, 390, 223-226.

Ellington, A.D.; Szostak, J.W. In vitro selection of RNA molecules that bind specific ligands. Nature 1990,346,818-822.

Tuerk, C.; Gold, L. Systematic evolution of ligands by exponential enrichment: RNA ligands to bacteriophage T4 DNA polymerase. Science 1990, 249, 505-510.

Supplementary European Search Report dated Jan. 8, 2016 in corresponding European Application No. EP 13760958, 9 pgs.

Luxton R. et al: "Use of External Magnetic Fields to Reduce Reaction Times in an Immunoassay Using Micrometer-Sized Paramagentic Particles as Labels (Magentoimmunoassay)", Analytical Chemistry, Americal Chemical Society, US, vol. 76, No. 6, Mar. 15, 2004 (Mar. 15, 2004), pp. 1715-1719, XP001196657, ISSN: 0003-2700, DOI: 10.1021/AC034906+.

Gijs et al: Microfluidic Application of Magentic Particles for Biological Analysis and Catalysis:, Chemical Review, American Chemical Society, US, vol. 110, No. 3, Jan. 1, 2010 (Jan. 1, 2010), pp. 1518-1563, XP007917138, ISSN: 0009-2665, DOI: 10.1021/CR9001929 [retrieved on Apr. 12, 2009].

Office Action in corresponding Japanese application No. 2014-238245 dated Jul. 26, 2016, 9 pgs.

Schuler et al., "A Disposable and Cost Efficient Microfluidic Device for the Rapid Chip-Based Electrical Detection of DNA", Biosensors and Bioelectronics 25 (2009) 15-21.

European Search Report dated Jul. 25, 2017 in EP Application No. 08858855.3, 14 pgs.

Sipova et al., "Surface Plasmon Resonance Biosensor for Rapid Label-Free Detection of Microribonucleic Acid at Subfemtomole Level," Analytical Chemistry, vol. 82, No. 24, Dec. 15, 2010, pp. 10110-10115.

Coutlee et al., "Immunodetection of DNA with biotinylated RNA probes: A study of reactivity of a monoclonal antibody to DNA-RNA hybrids," Analytical Biochemistry, Elsevier, Amsterdam, NL, vol. 181, No. 1, Aug. 15, 1989, pp. 95-105.

European Search Report dated Oct. 18, 2017 in EP Application No. 17185137.1, 9 pgs.

\* cited by examiner

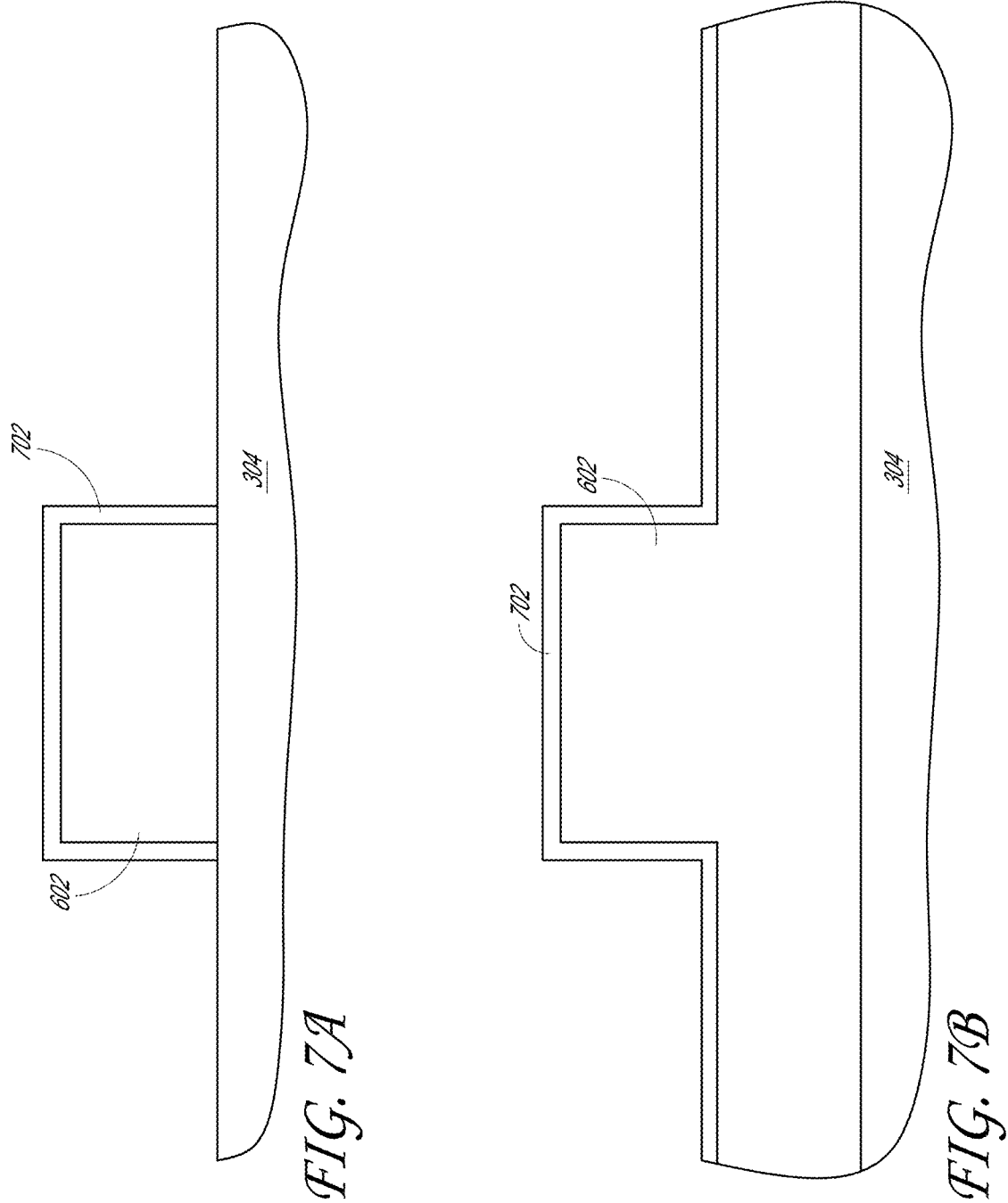

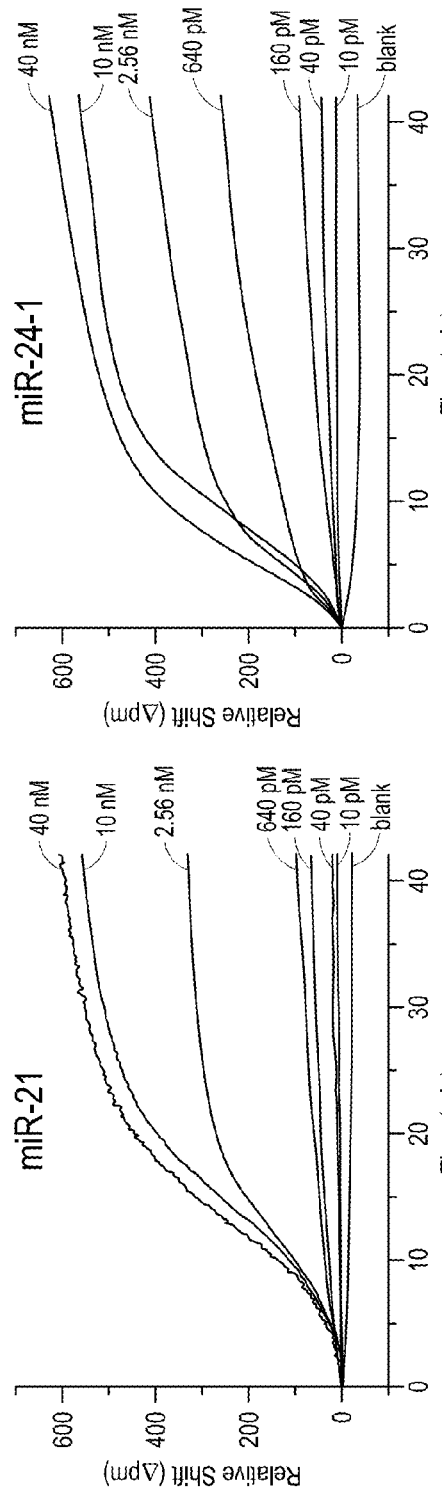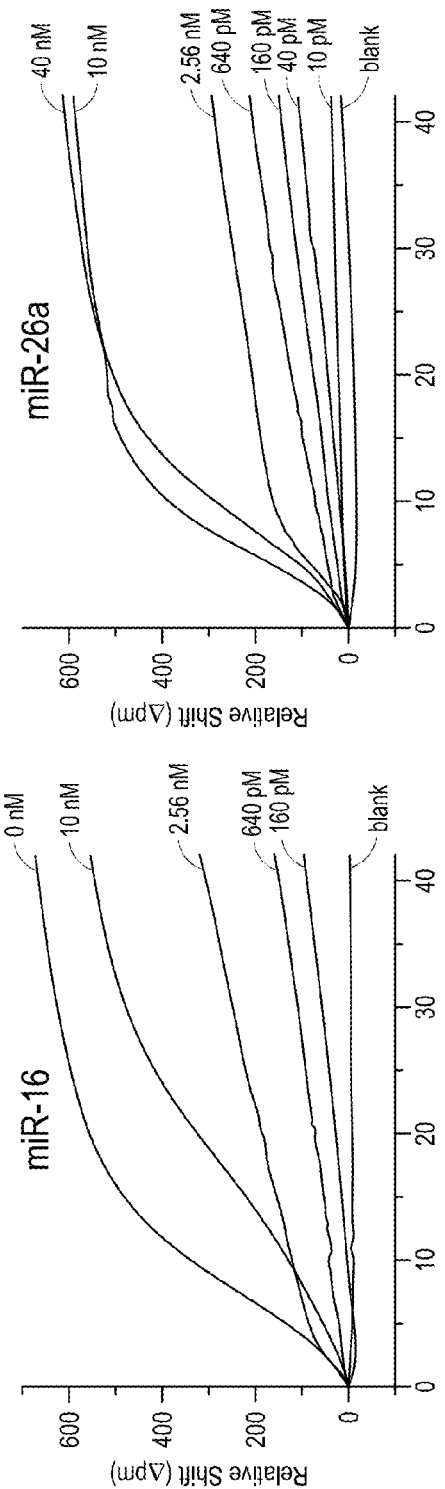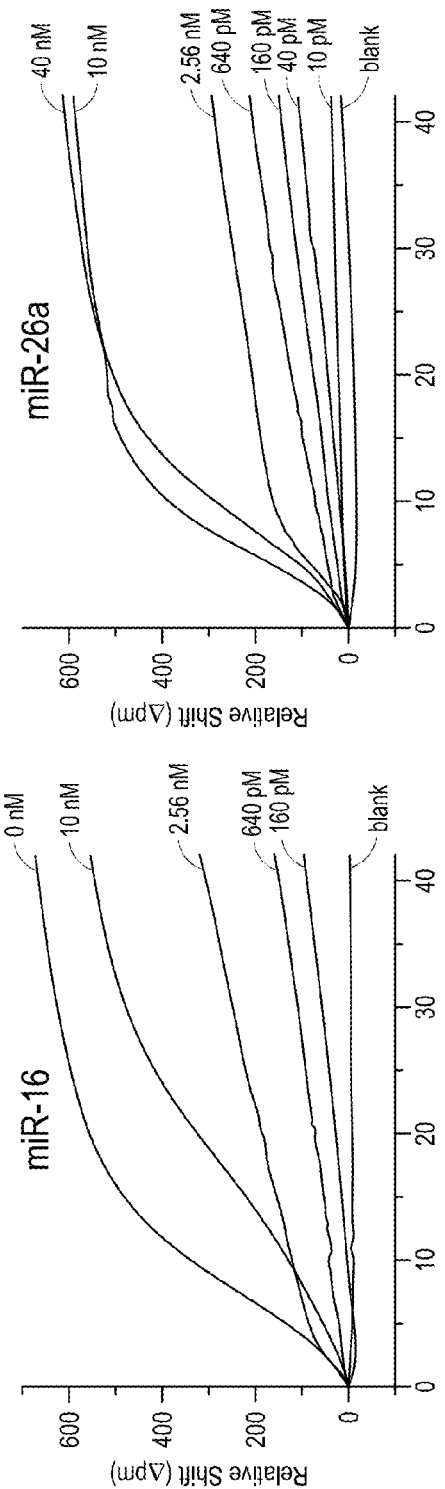

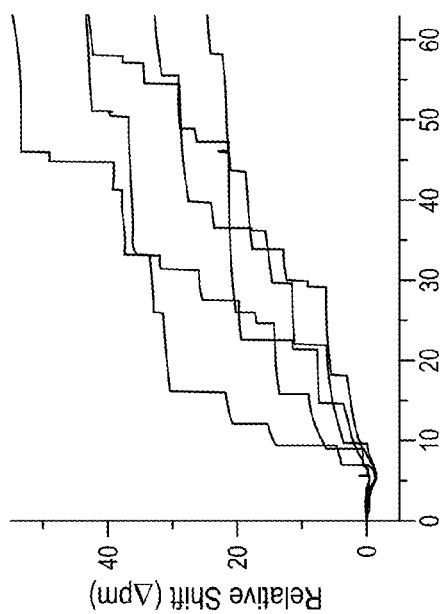
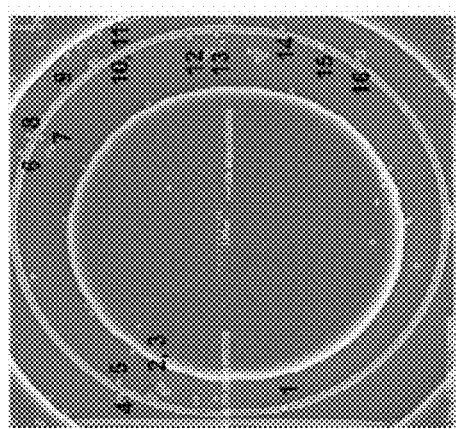
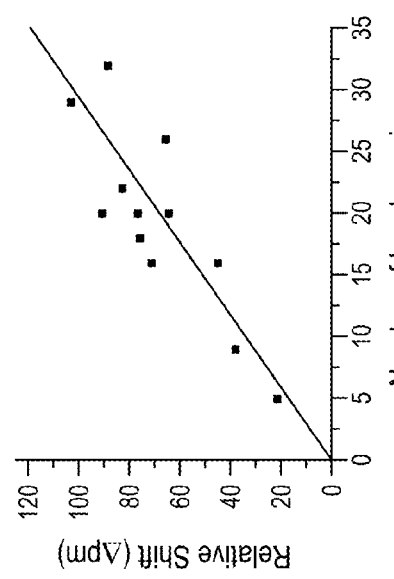
FIG. 22A
FIG. 22B
FIG. 22C

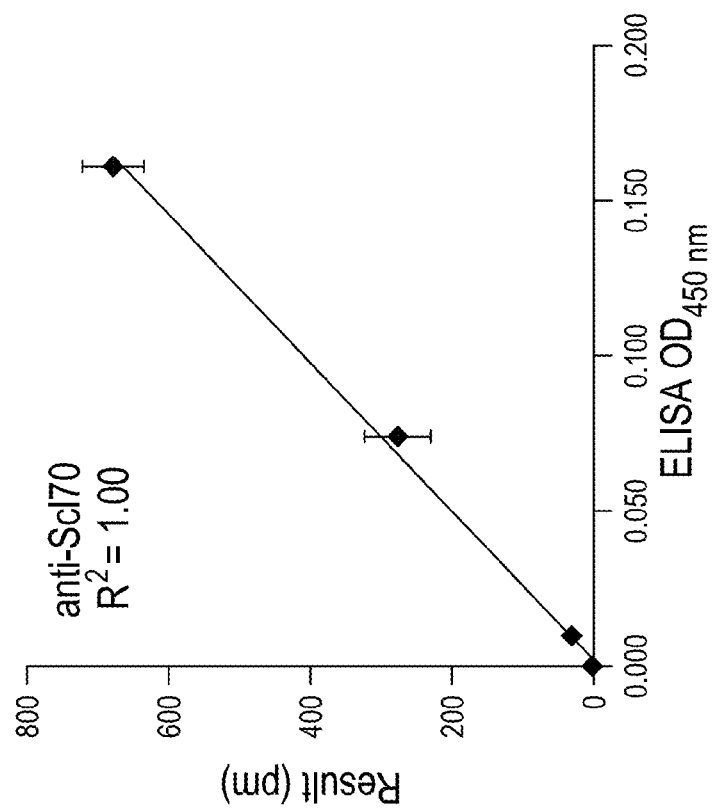
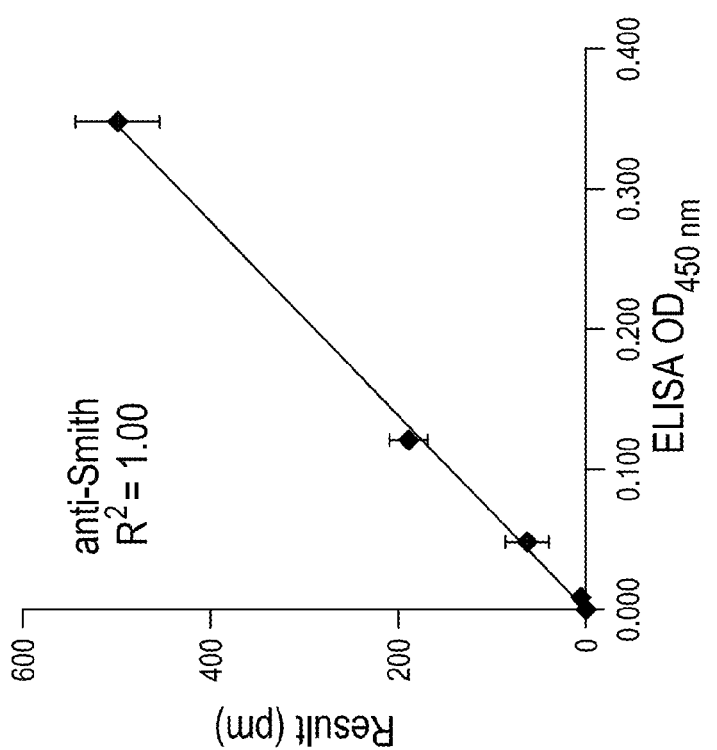

SEQUENCE LISTING

```
<160> NUMBER OF SEQ ID NOS: 14

<210> SEQ ID NO 1
<211> LENGTH: 22
<212> TYPE: RNA
<213> ORGANISM: Homo sapiens

<400> SEQUENCE: 1
uagcagcacg uaaauauugg cg                                                  22

<210> SEQ ID NO 2
<211> LENGTH: 22
<212> TYPE: RNA
<213> ORGANISM: Homo sapiens

<400> SEQUENCE: 2
uagcuuauca gacugauguu ga                                                  22

<210> SEQ ID NO 3
<211> LENGTH: 22
<212> TYPE: RNA
<213> ORGANISM: Homo sapiens

<400> SEQUENCE: 3
uggcucaguu cagcaggaac ag                                                  22

<210> SEQ ID NO 4
<211> LENGTH: 22
<212> TYPE: RNA
<213> ORGANISM: Homo sapiens

<400> SEQUENCE: 4
uucaaguaau ccaggauagg cu                                                  22

<210> SEQ ID NO 5
<211> LENGTH: 22
<212> TYPE: DNA
<213> ORGANISM: Artificial Sequence
<220> FEATURE:
<223> OTHER INFORMATION: Synthetic oligo

<400> SEQUENCE: 5
```

-continued

```
atcgtcgtgc atttataacc gc                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic oligo

<400> SEQUENCE: 6
atcgaatagt ctgactacaa ct                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic oligo

<400> SEQUENCE: 7
ctgttcctgc tgaactgagc ca                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligo

<400> SEQUENCE: 8
aagttcatta ggtcctatcc ga                                              22

<210> SEQ ID NO 9
<211> LENGTH: 10
<212> TYPE: RNA
<213> ORGANISM: Artificial Sequence
<220> FEATURE:
<223> OTHER INFORMATION: Synthetic oligo

<400> SEQUENCE: 9
aaaggugcgu                                                            10

<210> SEQ ID NO 10
<211> LENGTH: 20
<212> TYPE: RNA
<213> ORGANISM: Artificial Sequence
<220> FEATURE:
<223> OTHER INFORMATION: Synthetic oligo

<400> SEQUENCE: 10
aaaggugcgu uuauagaucu                                                 20

<210> SEQ ID NO 11
<211> LENGTH: 40
<212> TYPE: RNA
<213> ORGANISM: Artificial Sequence
<220> FEATURE:
<223> OTHER INFORMATION: Synthetic oligo

<400> SEQUENCE: 11
aaaggugcgu uuauagaucu agacuagguu gcagcaacua                           40

<210> SEQ ID NO 12
<211> LENGTH: 40
<212> TYPE: DNA
<213> ORGANISM: Artificial Sequence
```

```
<220> FEATURE:
<223> OTHER INFORMATION: Synthetic oligo

<400> SEQUENCE: 12
tagttgctgc aacctagtct agatctataa acgcaccttt                       40

<210> SEQ ID NO 13
<211> LENGTH: 54
<212> TYPE: DNA
<213> ORGANISM: Artificial Sequence
<220> FEATURE:
<223> OTHER INFORMATION: Synthetic oligo

<400> SEQUENCE: 13
ctgttcctgc tgaactgagc caaaaaaaaa aactgttcct gctgaactga gcca       54

<210> SEQ ID NO 14
<211> LENGTH: 22
<212> TYPE: DNA
<213> ORGANISM: Artificial Sequence
<220> FEATURE:
<223> OTHER INFORMATION: Synthetic oligo

<400> SEQUENCE: 14
ctgttcctgc tgaactgagc ca                                          22
```

OPTICAL ANALYTE DETECTION SYSTEMS AND METHODS OF USE

CROSS-REFERENCE TO RELATED APPLICATIONS

This application claims the benefit under 35 U.S.C. § 119(e) of U.S. Provisional Application No. 61/410,595 filed Nov. 5, 2010 and U.S. Provisional Application No. 61/452,796 filed Mar. 15, 2011, the entireties of which are hereby incorporated by reference.

STATEMENT REGARDING FEDERALLY SPONSORED R&D

This invention was made with United States Government support under Grant No. 1-DP2-OD002190-awarded by the National Institutes of Health (NIH) Director's New Innovator Award Program. The United States Government has certain rights in the invention.

REFERENCE TO SEQUENCE LISTING

The present application is being filed along with a Sequence Listing in electronic format. The Sequence Listing is provided as a file entitled GNLYT002WO.TXT, created Nov. 3, 2011, which is 2.77 KB in size. The information in the electronic format of the Sequence Listing is incorporated herein by reference in its entirety.

FIELD

Various embodiments provided herein are applicable to the fields of optics and analyte detection.

BACKGROUND

The ability to perform multiple simultaneous biomarker measurements in complex samples with high sensitivity presents a large challenge to disease diagnostics and biological studies. Technologies such as polymerase chain reaction (PCR), reverse transcriptase-PCR (RT-PCR), and cDNA microarrays have been used for comparative and quantitative global DNA and mRNA expression studies. Two-dimensional polyacrylamide gel electrophoresis (2D-PAGE) and immunoassays, such as the enzyme-linked immunosorbent assay (ELISA), have been used to analyze protein components from complex mixtures. However, these technologies have several limitations and suffer from low dynamic range, low sensitivity, low specificity, labor intensiveness, lack of scalability or multiplex capability, inability to analyze large analytes, and/or inability to detect binding events in real-time. Moreover, many existing technology platforms, such as microarrays, are equilibrium based detection applications that are incapable of real-time binding detection, which is important for eliminating signal bias of non-specific binding. Another detection platform, Surface Plasmon Resonance (SPR) sensors, has been used to measure binding-induced changes in the local refractive index of the sensors, but is not amenable to large scale multiplexing or operation in complex media or clinical samples. These drawbacks have limited the widespread applicability of current detection platforms in diverse analytical settings.

SUMMARY

Various embodiments are drawn to systems and methods for analyte detection featuring one or more of the following: high dynamic range, high detection sensitivity and specificity, scalability and multiplex capacity, ability to analyze large analytes, and ability to detect or measure multiple binding events in real-time with reduced cross-talk from non-specific binding events. Furthermore, the systems and methods of various embodiments may involve low sample volume in the microliter range, only a relatively small amount of hands-on time, and provide rapid time to results, which are reproducible. Unlike existing analyte detection platforms, the systems of various embodiments are not impaired in wide-range applicability by having capacity for only some beneficial detection properties at the expense of others. Various embodiments of the systems and methods provided herein can potentially overcome the technical drawbacks that have hampered current detection platforms from being useful across a wide spectrum of contexts.

Several embodiments are drawn to a system for detecting a nucleic acid molecule of interest in a sample including an optical sensor; a nucleic acid capture probe attached to a surface of the optical sensor, wherein the capture probe is capable of hybridizing to the nucleic acid molecule of interest to form a duplex; and an antibody capable of specifically binding to the duplex of the capture probe and nucleic acid molecule of interest, wherein said optical sensor has an optical property that is altered when said antibody is bound to said duplex such that said optical sensor is configured to sense said antibody combined with said duplex.

Various embodiments relate to a system for detecting a nucleic acid molecule of interest in a sample including an optical sensor configured to resonate at a resonant wavelength; a light source capable of providing light at said resonant wavelength for the optical sensor; a nucleic acid capture probe attached to a surface of the optical sensor, wherein the capture probe is capable of hybridizing to the nucleic acid molecule of interest to form a duplex; an antibody capable of specifically binding to the duplex of the capture probe and nucleic acid molecule of interest; and a detector, wherein said optical sensor has an optical property that is altered when said antibody is bound to said duplex such that said optical sensor is configured to sense said antibody combined with said duplex and the detector is capable of detecting the optical property that is altered. The light source may comprise in various embodiments a laser such as a tunable laser or broad band light source such as a superluminescent laser diode (SLED).

Some embodiments are directed to a system for detecting an analyte of interest in a sample including an optical ring resonator, a capture probe attached to a surface of the optical ring resonator, wherein the capture probe is capable of binding to the analyte to form a complex, and an antibody capable of binding to the analyte or complex, wherein said optical ring resonator has an optical property that is altered by said antibody bound to said complex or analyte, when the analyte is bound to the capture probe, such that said optical ring resonator is configured to sense said antibody combined with said analyte or complex.

In several aspects of embodiments provided herein, the nucleic acid molecule of interest comprises deoxyribonucleic acid (DNA) or ribonucleic acid (RNA). In further aspects, the capture probe comprises a DNA oligonucleotide. In some aspects, the DNA oligonucleotide is complementary to the nucleic acid of interest or analyte of interest. In some aspects, the DNA oligonucleotide comprises a modified DNA nucleotide, such as a locked nucleic acid (LNA) or universal base. In some aspects of the aforementioned embodiments, the capture probe comprises an RNA oligonucleotide. In various aspects, the RNA oligonucleotide is complementary to the nucleic acid of interest or analyte of interest. In several aspects, the RNA oligonucleotide comprises a modified RNA nucleotide, such as a locked nucleic acid (LNA) or universal base.

In various aspects of embodiments provided herein, the antibody binds to a sequence-independent DNA:RNA duplex and does not bind to the nucleic acid molecule of interest or analyte of interest prior to the formation of the duplex. In one aspect, the antibody is S9.6.

In one aspect of embodiments provided herein directed to a system for detecting an analyte of interest, the analyte is a polypeptide. In some aspects, the capture probe is an antibody that specifically binds to the polypeptide.

In some aspects of any of the embodiments provided herein, the capture probe is covalently coupled to the surface of the optical sensor or optical ring resonator.

In another aspect of any of the embodiments provided herein, the optical sensor or optical ring resonator comprises a waveguide structure. In various aspects, the optical sensor or optical ring resonator has an output portion configured to output an optical signal. In some aspects, said optical sensor or optical ring resonator has a first optical state when said capture probe binds to the analyte of interest forming said complex and said antibody binds said complex, and wherein the optical sensor or optical ring resonator has a second state when said antibody does not bind to said complex, the optical output yielding different outputs when said optical sensor or optical ring resonator in said first and second optical states. In another aspect, the optical sensor or optical ring resonator comprises an input and an output portion each comprising portions of a waveguide. In several aspects, the optical sensor or optical ring resonator comprises an input waveguide and an output waveguide having optical coupling region therebetween configured to increase coupling of a wavelength component from said input waveguide to said output waveguide when said capture probe binds to the analyte of interest forming said complex and said antibody binds to said complex.

In certain aspects of any of the aforementioned embodiments, said optical sensor or optical ring resonator is integrated on an integrated optical chip comprising optical waveguides.

In various aspects of embodiments provided herein including an optical sensor, the optical sensor comprises a resonator. In several aspects, the resonator has a resonant wavelength that shifts when said capture probe binds to the analyte of interest forming said complex and said antibody binds to said complex. In various aspects, the optical sensor comprises a waveguide structure. Additionally in several aspects, the optical sensor comprises a resonator formed from a closed loop or ring resonator, such as a racetrack resonator. In some aspects, said closed-loop resonator comprises a waveguide structure.

In certain aspects of any of the embodiments provided herein, the antibody increases the sensitivity of the optical sensor or optical ring resonator in detecting the nucleic acid molecule of interest or analyte of interest when the antibody binds to the duplex or complex.

In several aspects of any of the embodiments provided herein, the antibody amplifies the optical property that is altered when the antibody binds to the duplex or complex.

Several embodiments relate to a method for detecting a nucleic acid molecule of interest in a sample including providing an optical sensor comprising a nucleic acid capture probe attached to a surface of the optical sensor, wherein the capture probe is capable of hybridizing to the nucleic acid molecule of interest to form a duplex; applying a sample for which the presence or absence of the nucleic acid molecule of interest is to be determined to the optical sensor under conditions in which the nucleic acid molecule of interest, when present, and the capture probe sequence-specifically hybridize to form a duplex; providing an antibody that specifically binds a duplex of nucleic acid molecules, wherein binding between the antibody and the duplex of the capture probe and nucleic acid molecule of interest alters an optical property of the optical sensor; and determining the presence or absence of the nucleic acid molecule of interest by detecting the altered optical property of the optical sensor.

In one aspect, the nucleic acid molecule of interest comprises ribonucleic acid (RNA). In another aspect, the optical sensor comprises a ring resonator. In various aspects, said ring resonator comprises a waveguide structure.

Various embodiments are drawn to a method for detecting an analyte of interest in a sample including providing an optical ring resonator comprising a capture probe attached to a surface of the optical ring resonator, wherein the capture probe is capable of binding to the analyte of interest to form a complex; applying a sample for which the presence or absence of the analyte of interest is to be determined to the optical ring resonator under conditions in which the analyte of interest, when present, and the capture probe bind to form a complex; providing an antibody that specifically binds to the complex or analyte, wherein binding between the antibody and the complex or the analyte, when the analyte is bound to the capture probe, alters an optical property of the optical ring resonator; and determining the presence or absence of the analyte of interest by detecting the altered optical property of the optical ring resonator.

In one aspect, the analyte of interest comprises ribonucleic acid (RNA). In another aspect, the analyte of interest is a polypeptide. In some aspects, the capture probe is an antibody that specifically binds to the polypeptide. In an additional aspect, the optical ring resonator comprises a waveguide structure.

Certain embodiments are drawn to a system for detecting a polypeptide of interest in a sample including an optical sensor; a first antibody that specifically binds to the polypeptide of interest, wherein the first antibody is attached to a surface of the optical sensor; a second antibody that specifically binds to the polypeptide of interest; and a particle attached to the second antibody or a particle capable of binding the second antibody, wherein said optical sensor has an optical property that is altered when said second antibody is bound to said polypeptide of interest, when said polypeptide of interest is bound to the first antibody, such that said optical sensor is configured to sense said second antibody combined with said polypeptide bound to said first antibody, and the particle is adapted to amplify the optical property that is altered.

Several embodiments relate to a system for detecting a polypeptide of interest in a sample including an optical sensor configured to resonate at a resonant wavelength; a light source capable of providing light at said resonant wavelength for the optical sensor; a first antibody that specifically binds to the polypeptide of interest, wherein the first antibody is attached to a surface of the optical sensor; a second antibody that specifically binds to the polypeptide of interest; and a particle attached to the second antibody or a particle capable of binding the second antibody; and a detector, wherein said optical sensor has an optical property that is altered when said second antibody binds to said polypeptide bound to said first antibody such that said optical sensor is configured to sense said second antibody combined with said polypeptide bound to the first antibody; the particle is adapted to amplify the optical property that is altered; and the detector is capable of detecting the optical property that is altered. The light source may comprise in various embodiments a laser such as a tunable laser or broad band light source such as a superluminescent laser diode (SLED).

Various embodiments are drawn to a system for detecting an analyte of interest in a sample including an optical sensor; a capture probe attached to a surface of the optical sensor, wherein the capture probe is capable of binding to the analyte; an antibody capable of specifically binding to the analyte or a complex formed between the analyte and the capture probe; and a particle attached to the antibody or capable of binding to the antibody, wherein said optical sensor has an optical property that is altered by said antibody bound to said complex or analyte, when the analyte is bound to the capture probe, such that said optical sensor is configured to sense said antibody combined with said analyte or complex, and the particle is adapted to amplify the optical property that is altered.

In certain aspects of any one of the preceding systems including a particle, the particle comprises a bead, polypeptide, nanoparticle, semiconductor crystal, titanium-oxide crystal, or quantum dot. In additional aspects, the particle comprises an average diameter of at least 1 nm. In further aspects, the bead comprises silicon, polystyrene, agarose, sepharose, metal, or metal-oxide. In another aspect, the particle comprises a polypeptide of at least 200 Daltons (Da). In various aspects, the polypeptide comprises myc, FLAG, GST, MBP, GFP, or beta-gal. In a further aspect, the polypeptide comprises Protein A, Protein G, or a combination of Protein A and Protein G, and is capable of binding to the antibody. In yet another aspect, the polypeptide comprises streptavidin and the antibody comprises biotin.

In certain aspects of the embodiments provided herein drawn to a system for detecting an analyte of interest in a sample including a particle attached to the antibody or capable of binding to the antibody, the analyte is a polypeptide. In several aspects, the capture probe is an antibody that specifically binds to the polypeptide. In another aspect, the capture probe comprises an aptamer that specifically binds to the polypeptide. In a further aspect, the capture probe comprises a protein that binds to the polypeptide.

In various aspects of the embodiments provided herein drawn to a system for detecting an analyte of interest in a sample including a particle attached to the antibody or capable of binding to the antibody, the analyte is a nucleic acid. In some aspects, the nucleic acid comprises ribonucleic acid (RNA). In various aspects, the capture probe comprises a DNA oligonucleotide. In several aspects, the DNA oligonucleotide is complementary to the nucleic acid. In various aspects, the DNA oligonucleotide comprises a modified DNA nucleotide, such as a locked nucleic acid (LNA) or universal base.

In other aspects, the capture probe comprises an RNA oligonucleotide. In some aspects, the RNA oligonucleotide is complementary to the nucleic acid. In various aspects, the RNA oligonucleotide comprises a modified RNA nucleotide, such as a locked nucleic acid (LNA) or universal base.

In various aspects of the embodiments herein drawn to systems including a particle attached to an antibody or capable of binding to an antibody, the capture probe is covalently coupled to the surface of the optical sensor.

In various aspects of the embodiments herein drawn to systems including a particle attached to an antibody or capable of binding to an antibody, the optical sensor comprises a waveguide structure. In other aspects, the optical sensor has an output portion configured to output an optical signal. In some aspects, said optical sensor has a first optical state when said capture probe binds to the analyte of interest forming said complex and said antibody binds said complex, and wherein the optical sensor has a second state when said antibody does not bind to said complex, the optical output yielding different outputs when said optical sensor in said first and second optical states.

In a further aspect, the optical sensor comprises an input and an output portion each comprising portions of a waveguide. In several aspects, the optical sensor comprises an input waveguide and an output waveguide having optical coupling region therebetween configured to increase coupling of a wavelength component from said input waveguide to said output waveguide when said capture probe binds to the analyte of interest forming said complex and said antibody binds to said complex.

In various aspects of the embodiments herein drawn to systems including a particle attached to an antibody or capable of binding to an antibody, said optical sensor is integrated on an integrated optical chip comprising optical waveguides. In further aspects, the optical sensor comprises a resonator. In some aspects, said resonator has a resonant wavelength that shifts when said capture probe binds to the analyte of interest forming said complex and said antibody binds to said complex. In another aspect, the optical sensor comprises a waveguide structure. In various aspects, the optical sensor comprises a ring resonator. In some aspects, said ring resonator comprises a waveguide structure.

Various embodiments are directed to a method for detecting a polypeptide of interest in a sample including providing an optical sensor comprising a first antibody attached to a surface of the optical sensor, wherein the first antibody specifically binds to the polypeptide of interest; applying a sample for which the presence or absence of the polypeptide of interest is to be determined to the optical sensor, under conditions in which the polypeptide of interest, when present, and the first antibody bind; providing a second antibody that specifically binds the polypeptide of interest, wherein binding between the second antibody and the polypeptide of interest, when bound to the first antibody, alters an optical property of the optical sensor; providing a particle attached to the second antibody or a particle capable of binding the second antibody, wherein the particle amplifies the optical property that is altered; and determining the presence or absence of the polypeptide of interest by detecting the altered optical property of the optical sensor.

In one aspect, the optical sensor comprises a ring resonator. In several aspects, said ring resonator comprises a waveguide structure.

Certain embodiments relate to a method for detecting an analyte of interest in a sample including providing an optical sensor comprising a capture probe attached to a surface of the optical sensor, wherein the capture probe is capable of binding to the analyte of interest to form a complex; applying a sample for which the presence or absence of the analyte of interest is to be determined to the optical sensor, under conditions in which the analyte of interest, when present, and the capture probe bind to form a complex; providing an antibody that specifically binds to the complex or analyte, wherein binding between the antibody and the complex or the analyte, when the analyte is bound to the capture probe, alters an optical property of the optical sensor; providing a particle attached to the antibody or a particle capable of binding the antibody, wherein the particle amplifies the optical property that is altered; and determining the presence or absence of the analyte of interest by detecting the altered optical property of the optical sensor.

In one aspect, the analyte of interest comprises ribonucleic acid (RNA). In another aspect, the optical sensor comprises a ring resonator. In some aspects, said ring resonator comprises a waveguide structure.

In various embodiments described herein, the particle comprises metal. In particular, the particle may comprise gold. The particle may comprises silver. In some embodiments the particle comprise dielectric. The particle may comprise a polymer. The particle may comprise a core that is coated. In some embodiments, the coating provides optical properties (e.g., high refractive index) and/or may assist in application of a capture probe. The particle may be magnetic. In some embodiments, the particle comprises a magnetic core and may have an overlayer or coating. Magnetic properties may be useful in processing the particles. Accordingly, the particle can comprise a gold bead, a silver bead, a dielectric bead, a polymer bead, a magnetic bead or a bead with a magnetic core. The bead may include a core and coating.

Several embodiments are drawn to detecting and/or measuring the concentration of an analyte of interest in a sample using the systems described above, which can provide for real-time multiplex detection and measurement of low abundance biomolecules with high sensitivity and specificity. It is possible to detect and/or measure binding-induced shifts in the resonance wavelength resulting from individual binding events in real-time with the systems of several embodiments. In some embodiments, such binding events detectable in real-time include a "primary" binding event between an analyte of interest (with or without a pre-bound particle) and a capture probe, a "secondary" binding event between an antibody (with or without a pre-bound particle) and the analyte of interest already bound to the capture probe, a "secondary" binding event between an antibody (with or without a pre-bound particle) and a duplex or complex formed between the analyte and capture probe, a "secondary" binding event between a particle and the analyte of interest already bound to the capture probe (e.g. wherein the capture probe comprises an antigen and the analyte of interest is an antibody against the antigen), or a "tertiary" binding event between a particle and antibody already bound to the optical sensor via a "secondary" binding event. In some aspects, a plurality of the same type of particle, such as a universal particle, can be used in a "tertiary" binding event. In certain aspects, the plurality of the same type of particle can be used in a multiplex format.

Various embodiments are directed to a system for detecting an analyte of interest in a sample, wherein the system includes a substrate, an optical sensor disposed on said substrate, said optical sensor including at least one waveguide, a first ring resonator, and a second ring resonator, wherein said at least one waveguide and said first and second ring resonators in optical communication with each other such that light propagating in the at least one waveguide can propagate to said first and second ring resonators. The optical sensor, for example, one or more of the at least one waveguide, the first ring resonator, and the second ring resonator may have a capture probe, for example, to capture an analyte of interest.

In some embodiments, the first ring resonator and the second ring resonator are cascaded. In some embodiments, the first ring resonator and the second ring resonator have substantially the same optical path length and resonant wavelengths.

In some embodiments, neither the first ring resonator is between the at least one waveguide and the second ring resonator nor the second ring resonator is between the at least one waveguide and the first ring resonator. In some embodiments, the first ring resonator and the second ring resonator have different sizes and resonant wavelengths. In some embodiments, the first ring resonator and the second ring resonator have different capture probes for capturing different analytes.

In some embodiments, the system further includes a waveguide structure that is not a ring resonator disposed between the first and second ring resonators. In some embodiments, the first ring resonator and the second ring resonator form part of a Vernier resonator configuration. In some embodiments, the first ring resonator and second ring resonator have different sizes and resonant wavelengths.

In various embodiments as described herein, beads or other particles may be used to provide an amplifying effect on the signal. Other techniques such as those described herein may also be used to provide amplifying effects.

Various embodiments are directed to a system for detecting an analyte of interest in a sample, wherein the system includes a light source; a waveguide structure having a capture probe configured to bind with the analyte of interest, said waveguide structure having an input for receiving light from the light source such that light from the light source is guided in the waveguide structure; at least one particle that is disposed in sufficient proximity to the waveguide structure when said analyte of interest binds with the capture probe such that at least a portion of said light guided within said light guide is scattered out of the light guide; and a detector for detecting at least a portion of said light propagating within the waveguide structure that is scattered out of the waveguide structure by the at least one particle.

In some embodiments, the waveguide structure comprises a ring resonator.

In some embodiments, the light source comprises a tunable laser.

In some embodiments, the light source comprises a superluminescent diode.

In some embodiments, the detector comprises a detector array.

In some embodiments, the system further includes scanning optics for receiving light from said light source and directing said light to said waveguide structure. In some embodiments, said scanning optics are disposed in a light path between said waveguide structure and said detector such that said scanning optics receive light scattered by said particles and directs said light to said detector.

Without being bound by theory, resonance wavelengths on the optical sensor of several embodiments are sensitive to the local refractive index. Biomolecular binding events that increase the refractive index at the sensor surface of various embodiments can be observed as an increase in the resonant wavelengths of the optical sensor. Similar to a sandwich assay format in which an antigen is first bound by a substrate-immobilized primary capture agent and then recognized by a secondary capture agent, the systems of several embodiments include a capture probe (analogous to a sandwich assay primary capture agent) and an antibody (analogous to a sandwich assay secondary capture agent).

BRIEF DESCRIPTION OF THE DRAWINGS

FIG. 2 schematically illustrates the range of wavelengths that may be input into the optical sensor and the resultant spectral output of the optical sensor. A decrease in the optical output at the resonance frequency of the ring resonator is visible in the output spectrum shown.

FIG. 7A is a cross-section through a waveguide such as a silicon strip waveguide having a silicon dioxide layer thereon.

FIG. 7B is a cross-section through a waveguide such as a silicon rib waveguide having a silicon dioxide layer thereon.

FIGS. 16-1 to 16-4 are graphs showing simultaneous amplification of miRNA targets in terms of relative wavelength shift over time. Only those channels containing complementary capture probes and target miRNAs elicit an S9.6 response, allowing multiplexed miRNA analysis.

FIG. 17 shows an overlay of the signal responses achieved for each concentration of target miRNA: miR-21 (FIG. 17A), miR-24-1 (FIG. 17B), miR-16 (FIG. 17C), and miR-26a (FIG. 17D). Concentrations utilized were 40 nM, 10 nM, 2.56 nM, 640 pM, 160 pM, 40 pM, 10 pM, and a blank (with the exception of miR-16, which did not contain the 40 pM and 10 pM calibration points).

FIG. 22A is a graph showing real-time response of protein G-conjugated polystyrene beads binding to an array of antibody-functionalized microring resonators. The discrete jumps in relative resonance wavelength shift can be attributed to individual binding events of either single beads or bead aggregates. FIG. 22B is a scanning electron microscopy (SEM) image stitched from four high resolution images, which allows enumeration of beads bound to a given microring. Only beads directly contacting the ring within the evanescent field are counted. FIG. 22C is a plot of resonance wavelength shifts versus number of bound beads, which illustrates a linear trend providing evidence that individual, biomolecularly directed bead binding events can be observed using a microring resonator.

FIGS. 26A-D are graphs showing correlation between the optical ring detection system and ELISA for the detection of the auto-antibodies to Jo-1 (FIG. 26A), SSA and SSB (FIG. 26B), Smith (FIG. 26C), and Scl-70 (FIG. 26D).

DETAILED DESCRIPTION

Figure 1:
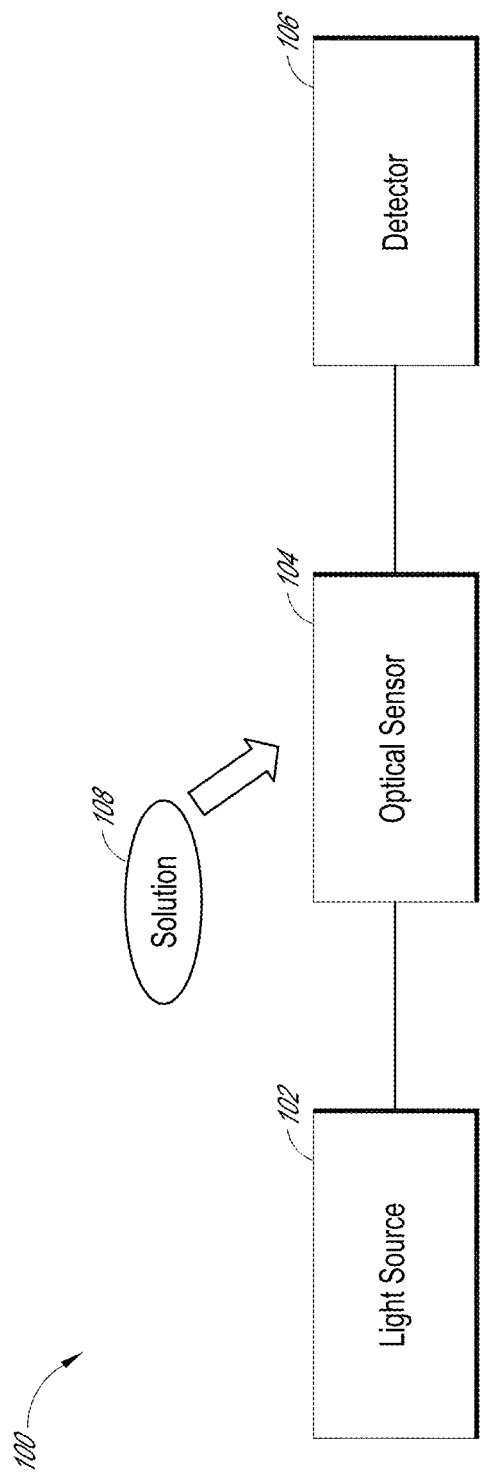
FIG. 1 is a schematic block diagram of a system for detecting an analyte comprising a light source that may include a light source (e.g. a tunable light source or a broad band light source), an optical sensor, and an optical detector.

In contrast to existing analyte detection technologies, various systems of several embodiments provided herein feature one or more of the following: high detection sensitivity and specificity, scalability and multiplex capacity, ability to analyze large analytes, and ability to detect or measure multiple individual analyte binding events in real-time. Furthermore, the systems and methods of various embodiments involve low sample volume in the microliter range and only a relatively small amount of hands-on time, and provide rapid time to results, which are reproducible. Eliminating the drawbacks of current technologies, the systems and methods of various embodiments are a major technological breakthrough in analyte detection, surpassing the existing detection platforms for widespread applicability in diverse analytical settings.

Optical sensors, such as silicon photonic microring resonators, have high spectral sensitivity towards surface binding events between an analyte of interest and an optical sensor modified with a probe for capturing the analyte of interest (i.e. a capture probe). The systems of several embodiments are based on refractive index-based sensing schemes in which the mass of bound analytes, potentially in combination with other factors such as capture probe affinity and surface density, contributes to the observed signal and measurement sensitivity.

Analytes, such as proteins, that are simultaneously low in abundance and have a lower molecular weight are often very difficult to detect. Several embodiments relate to employing a more massive antibody to amplify the signal arising from the initial primary binding event between the analyte and capture probe. Based on the present discovery that a remarkable femtomolar ($10^{-15}$) range of detection sensitivity can be achieved, various embodiments relate to employing a particle to further amplify the signal arising from the primary binding event and/or the signal arising from the secondary binding event of the "secondary" antibody. In certain embodiments, it is possible to improve both the sensitivity and/or the specificity of analyte detection assays, allowing for quantitative sensing in complex sample matrices.

One important class of analytes, microRNAs (miRNAs), are expressed at low levels in many organisms but nevertheless have important cellular roles and are associated with several diseases. miRNAs have become important biomarkers for a variety of diseases and conditions, but existing technologies lack the sensitivity to adequately detect or measure them due to their low abundance.

The systems of several embodiments herein can improve the sensitivity of detecting miRNA analytes in a rapid, multiplexed, and high-throughput detection format in real-time. The systems of several embodiments herein can detect microRNA at concentrations as low as 10 pM (350 attomoles) with a rapid time-to-result. The simplicity and widespread applicability of various of these embodiments make them an useful tool for high-throughput, multiplexed miRNA analysis, as well as a range of other RNA based detection applications.

It will be understood that as used herein, the singular forms "a," "an", and "the" include plural referents unless indicated to the contrary. Also, it will be understood that the term "detecting" an analyte as used herein also includes measuring the amount or concentration of an analyte because the systems and methods of various embodiments can provide both qualitative and quantitative detection, which can include measurement of a small number or even individual binding events in real-time.

Optical Sensing

Analyte detection can be accomplished using an optically based system 100 such as shown schematically in FIG. 1. The system 100 includes a light source 102, an optical sensor 104, and an optical detector 106. In various embodiments, the light source 102 outputs a range of wavelengths. For example, the light source 102 may be a relatively narrow-band light source that outputs light having a narrow bandwidth wherein the wavelength of the light source is swept over a region many times the bandwidth of the light source. This light source 102 may, for example, be a laser. This laser may be a tunable laser such that the wavelength of the laser output is varied. In some embodiments the laser is a diode laser having an external cavity. This laser need not be limited to any particular kind and may, for example, be a fiber laser, a solid state laser, a semiconductor laser or other type of laser or laser system. The laser itself may have a wavelength that is adjustable and that can be scanned or swept. Alternatively, additional optical components can be used to provide different wavelengths. In some embodiments, the light source outputs light having a wavelength for which the waveguide structure is sufficiently optically transmissive. In some embodiments, the waveguide structure is within a sample medium such as an aqueous medium and the light source outputs light having a wavelength for which the medium is substantially optically transmissive such that resonance can be reached in the optical resonator. Additionally, in some embodiments, the light source output has a wavelength in a range where the analyte (e.g., molecules) of interest do not have a non-linear refractive index. Likewise, in various embodiments, the light source 102 may be a coherent light source and output light having a relatively long coherence length. However, in various embodiments, the light source 102 may be a coherent light source that outputs light having a short coherence length. For example, in certain embodiments, a broadband light source such as a super-luminescent light emitting diode (SLED) may be used. In such cases, the wavelength need not be swept.

The light source 102 provides light to the optical sensor 104. The light source 102 may be controlled by control electronics. These electronics may, for example, control the wavelength of the light source, and in particular, cause the light source 102 to sweep the wavelength of the optical output thereof. In some embodiments, a portion of the light emitted from the light source 102 is sampled to determine, for example, the emission wavelength of the light source.

In some embodiments, the optical sensor 104 comprises a transducer that alters the optical input based on the presence and/or concentration of the analyte to be detected. The optical sensor 104 may be a waveguide structure. The optical sensor 104 may be an integrated optical device and may be included on a chip. The optical sensor 104 may comprise semiconductor material such as silicon. The optical sensor 104 may be an interferometric structure (e.g., an interferometer) and produce an output signal as a result of optical interference. The optical sensor 104 may be included in an array of optical sensors 104.

The optical detector 106 detects the optical output of the sensor 104. In various embodiments, the optical detector 106 comprises a transducer that converts an optical input into an electrical output. This electrical output may be processed by processing electronics to analyze the output of the sensor 104. The optical detector 106 may comprise a photodiode detector. Other types of detectors 106 may be employed. Collection optics in an optical path between the sensor 104 and the detector 106 may facilitate collection of the optical output of the sensor 104 and direct this output to the detector 106. Additional optics such as mirrors, beam-splitters, or other components may also be included in the optical path from the sensor 104 to the detector 106.

In various embodiments, the optical sensor 104 is disposed on a chip while the light source 102 and/or the optical detector 106 are separate from the chip. The light source 102 and optical detector 106 may, for example, be part of an apparatus comprising free space optics that interrogates the optical sensors 106 on the chip, as will be discussed in more detail below.

In various embodiments, a solution 108 such as an analyte solution is flowed past the optical sensor 104. The detector 106 detects modulation in an optical signal from the optical sensor 104 when an analyte of interest is detected.

Ring resonators offer highly sensitive optical sensors that can be prepared so as to detect analytes. The operation of a ring resonator is shown in connection with FIG. 2. In this configuration, the optical sensor 104 comprises an input/output waveguide 202 having an input 204 and an output 206 and a ring resonator 208 disposed in proximity to a portion of the input/output waveguide 202 that is arranged between the input 204 and the output 206. The close proximity facilitates optical coupling between the input/output waveguide 202 and the ring resonator 208, which is also a waveguide. In this example, the input/output waveguide 202 is linear and the ring resonator 208 is circular such that light propagating in the input/output waveguide 202 from the input 204 to the output 206 is coupled into the ring resonator 208 and circulates therein. Other shapes for the input/output waveguide 202 and ring resonator 208 are also possible.

Figure 2:
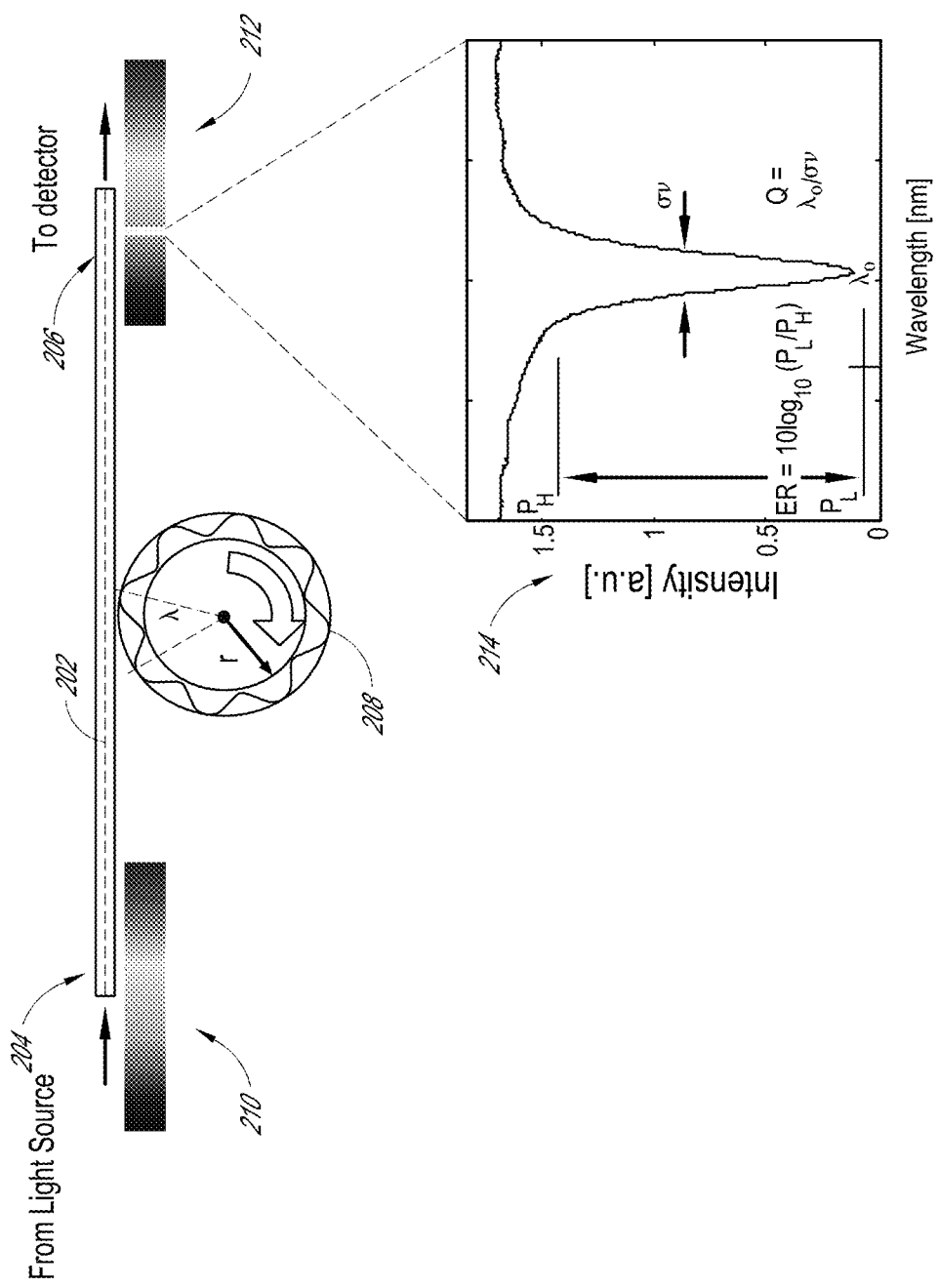
FIG. 2 shows a schematic diagram of an optical sensor comprising a waveguide and a ring resonator.

FIG. 2 shows an input spectrum 210 to represent that the light injected into the waveguide input 204 includes a range of wavelengths, for example, from a narrow band light source having a narrow band peak that is swept over time (or from a broadband light source such as a super-luminescent diode). Similarly, an output spectrum 212 is shown at the waveguide output 206. A portion of this output spectrum 212 is expanded into a plot of intensity versus wavelength 214 and shows a dip or notch in the spectral distribution at the resonance wavelength, $\lambda_0$, of the ring resonator 208.

Without subscribing to any particular scientific theory, light "resonates" in the ring resonator when the number of wavelengths around the ring (e.g. circumference) is exactly an integer. In this example, for instance, at particular wavelengths, light circulating in the ring resonator 208 is at an optical resonance when $$m\lambda = 2\pi r n \qquad \text{Eq. 1}$$

where m is an integer, $\lambda$ is the wavelength of light, r is the ring radius, and n is the refractive index. In this resonance condition, light circulating in the ring interferes with light propagating within the linear waveguide 202 such that optical intensity at the waveguide output 206 is reduced. Accordingly, this resonance will be measured as an attenuation in the light intensity transmitted down the linear waveguide 202 past the ring resonator 208 as the wavelength is swept by the light source in a manner such as shown in the plot 214 of FIG. 2.

Notably, the plot 214 in FIG. 2 shows the dip or notch having a width, $\delta\upsilon$ as measured at full width half maximum (FWHM) and an associated cavity Q or quality factor, $Q = \lambda_0/\delta\upsilon$. The ring resonator 208 produces a relatively high cavity Q and associated extinction ratio (ER) that causes the optical sensor 104 to have a heightened sensitivity.

Figure 3:
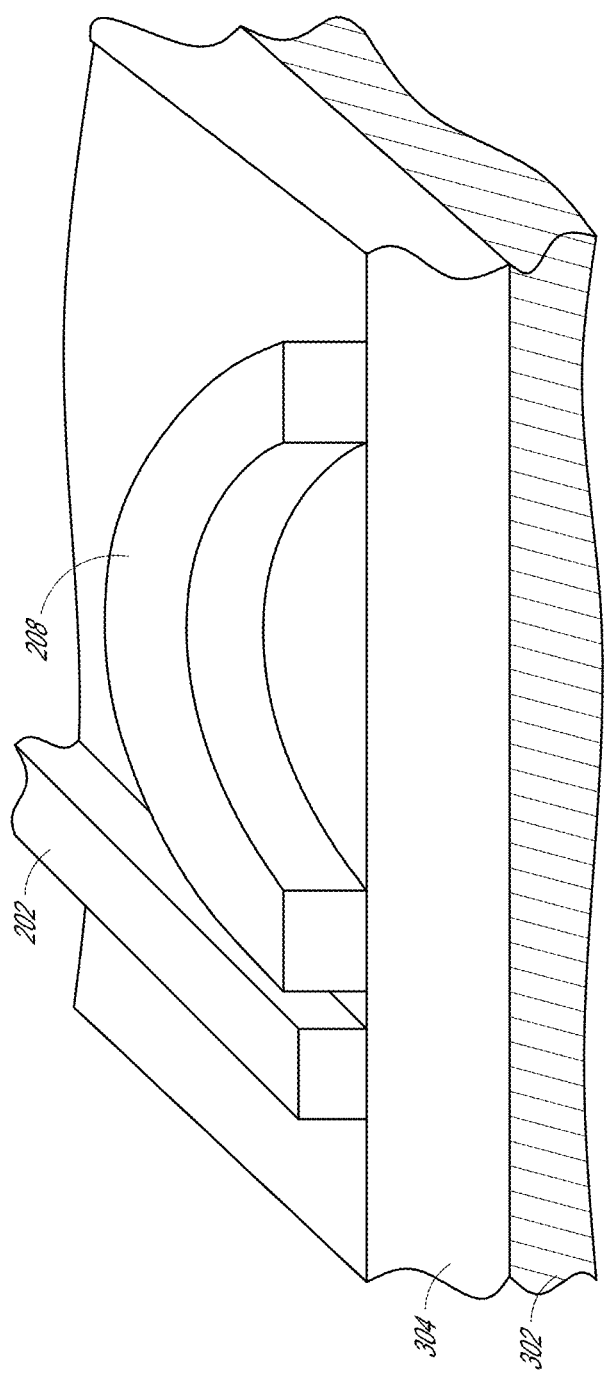
FIG. 3 shows a cut-away view of the optical sensor comprising a waveguide and a ring resonator.

A perspective view of the optical sensor 104 comprising a linear waveguide 202 and a ring resonator 208 is shown in FIG. 3. Both are waveguide structures as is this optical sensor 104. The linear waveguide 202 and the ring resonator 208 are disposed on a substrate 302 with a lower cladding layer 304 therebetween. Other configurations are possible, for example, other layers may be added (or removed) or patterned differently. This portion of the substrate 302 having the linear waveguide 202 and ring resonator 208 formed thereon may be part of a larger integrated optical chip.

Figure 4:
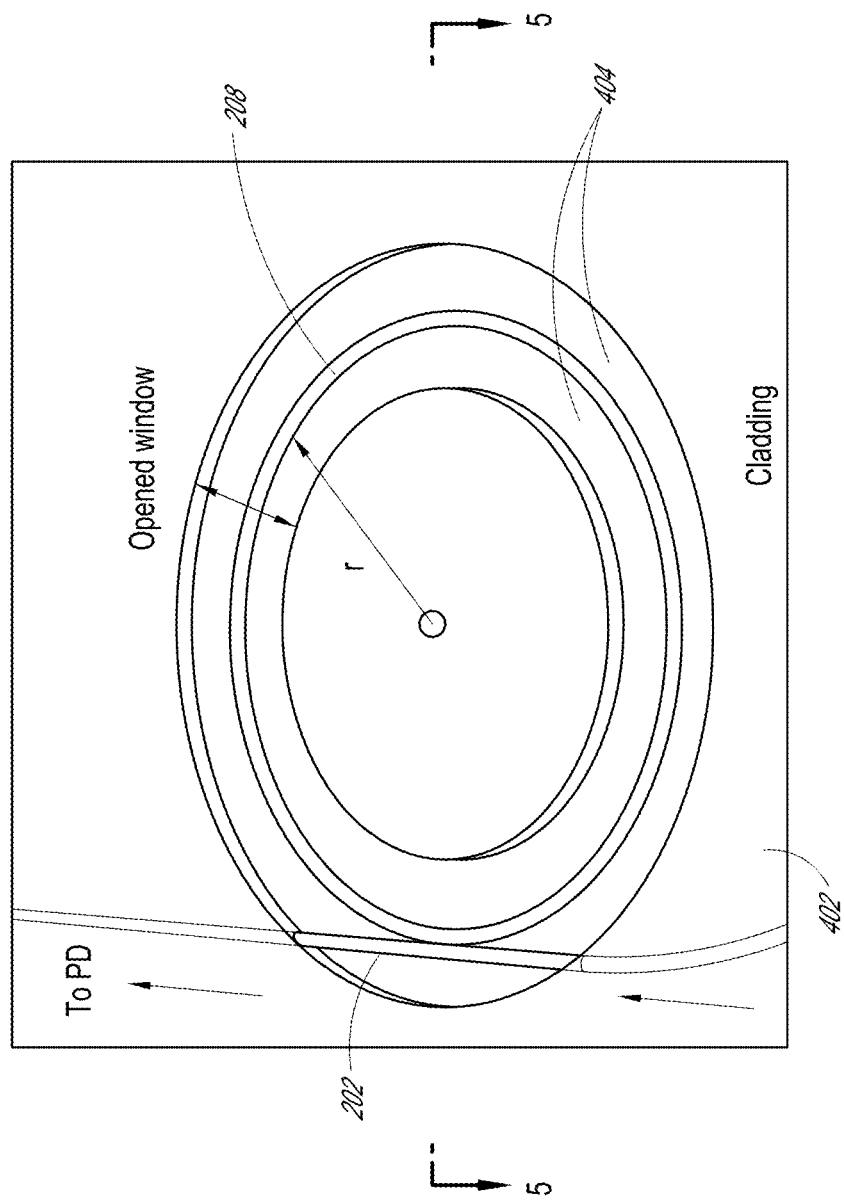
FIG. 4 is a perspective view an optical sensor such as shown in FIG. 3.

A drawing of an example biosensor waveguide structure comprising a linear waveguide 202 and a ring resonator 208 is also shown in FIG. 4. An upper cladding 402 is disposed over most of the area shown. However, a window 404 (here annular in shape) is included in the upper cladding 402 and provides exposure to portions of the linear waveguide 202 and the ring resonator 208. An analyte solution can thereby be flowed across the linear waveguide 202 and ring resonator 208 and permitted to interact therewith. The upper cladding 402 limits the exposure of the integrated waveguide structure to the analyte solution.

Figure 5:
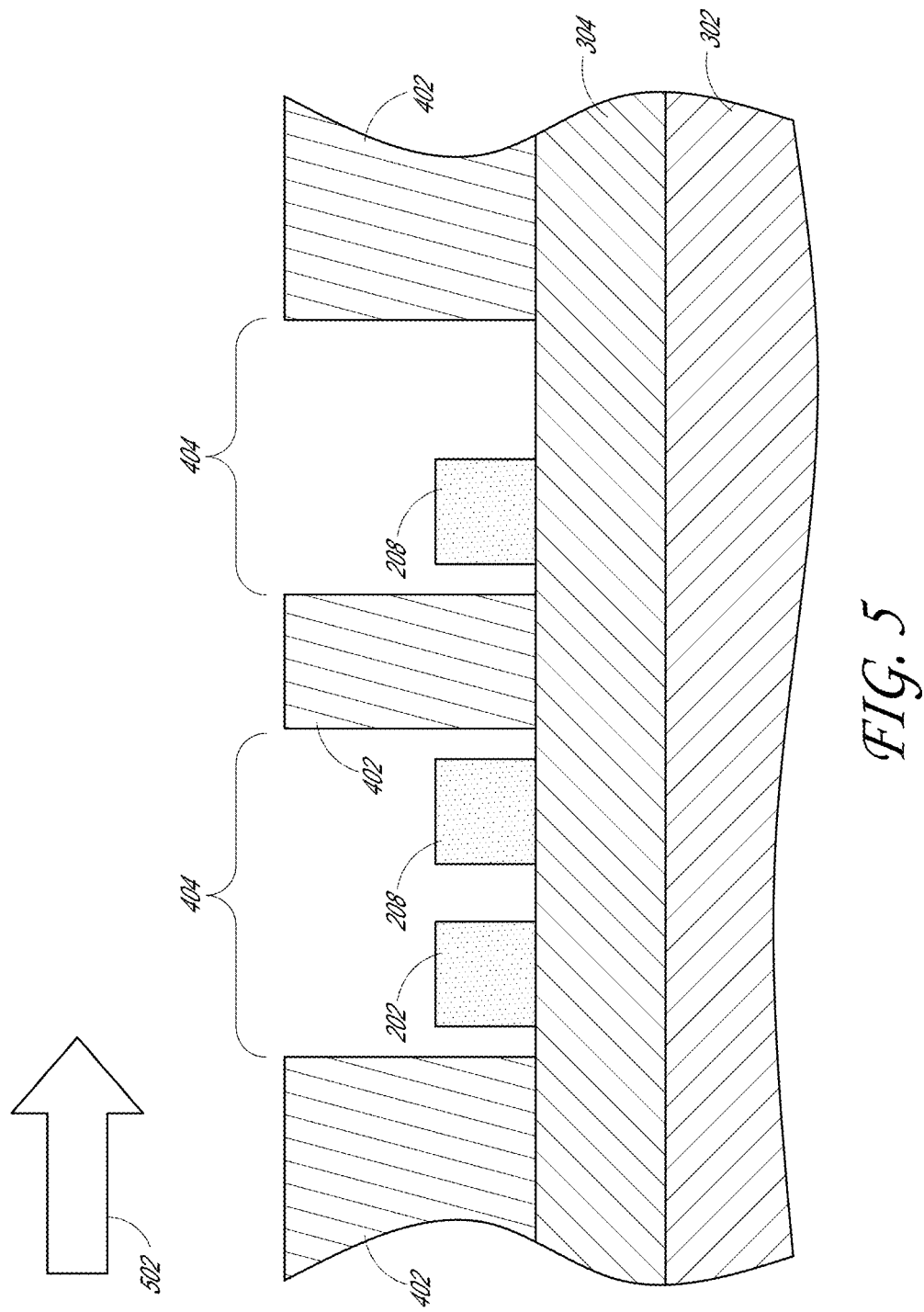
FIG. 5 is a cross-section through the waveguide and ring resonator shown in FIG. 4 along the line 5-5.

A cross-section through the line 5-5 shown in FIG. 4 is presented in FIG. 5. The cross-section shows the linear waveguide 202 and the ring resonator 208 disposed over the lower cladding 304 and substrate 302. The upper cladding 402 is also illustrated. As discussed above, openings or windows 404 in the upper cladding 402 provide access for the analyte solution to the linear waveguide 202 and ring resonator 208. A flow channel 502 (shown schematically by an arrow) for the analyte solution is also illustrated.

Figure 6:
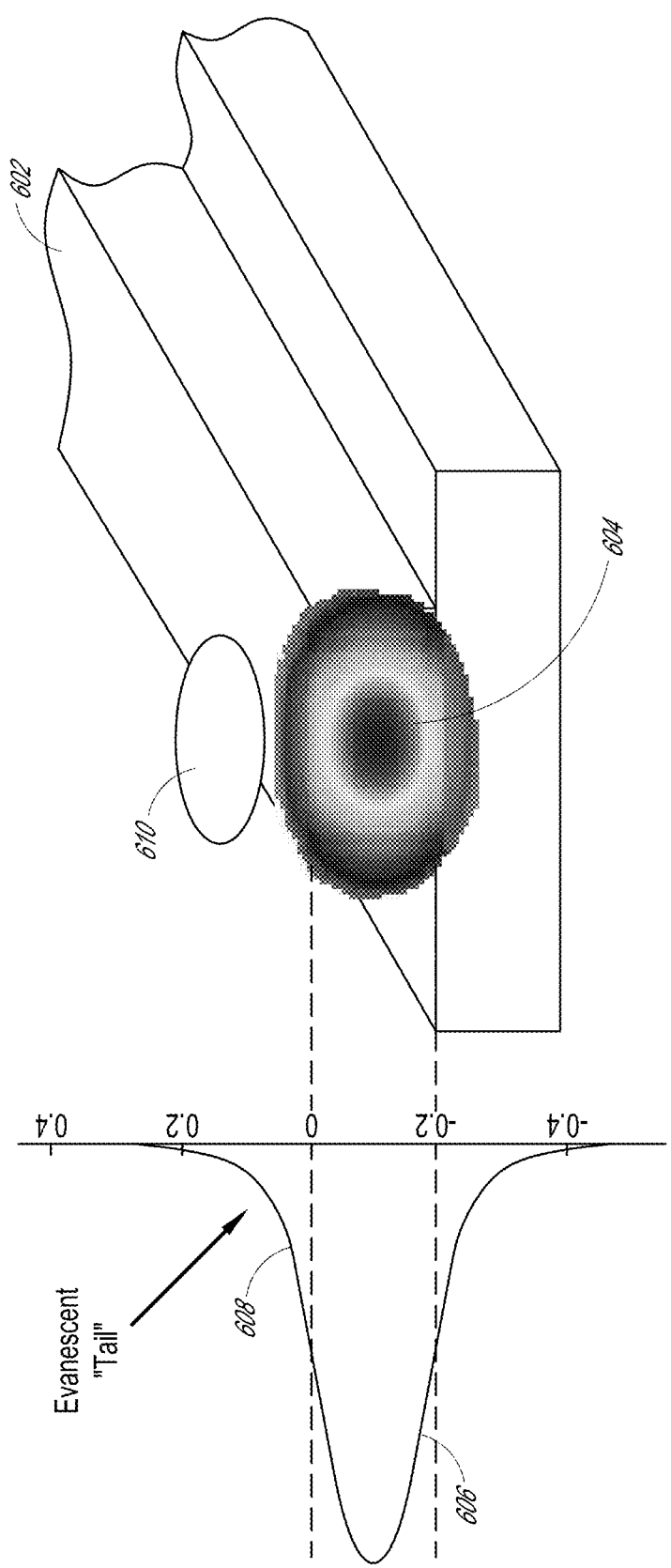
FIG. 6 is a cut-away view of a waveguide schematically showing an intensity distribution having an evanescent tail extending outside the waveguide where an element such as a molecule or particle may be located so as to affect the index of refraction of the waveguide.

As is well known, light propagates within waveguides via total internal reflection. The waveguide supports modes that yield a spatially varying intensity pattern across the waveguide. A cross-section of a waveguide 602 shown in FIG. 6 illustrates an example intensity distribution 604. A plot 606 of the intensity distribution at different heights is provided adjacent the waveguide structure 602. As illustrated, a portion 608 of the electric field and optical energy referred to as the evanescent "tail" lies outside the bounds of the waveguide 602. The length of this field 608, as measured from the 1/e point, is between 50 and 150 nm, e.g. about 100 nm in some cases. An object 610 located close to the waveguide 602, for example, within this evanescent field length affects the waveguide. In particular, objects 610 within this close proximity to the waveguide 602 affect the index of refraction of the waveguide. The index of refraction, n, can thus be different when such an object 610 is closely adhered to the waveguide 602 or not. In various embodiments, for example, the presence of an object 610 increases the refractive index of the waveguide 602. In this manner, the optical sensor 104 may be perturbed by the presence of an object 610 in the vicinity of the waveguide structure 602 thereby enabling detection. In various embodiments, the size of the particle is about the length (e.g. 1/e distance) of the evanescent field to enhance interaction therebetween.

In the case of the ring resonator 208, an increase in the refractive index, n, increases the optical path length traveled by light circulating about the ring. Longer wavelengths can resonate in the resonator 208 and, hence, the resonance frequency is shifted to a lower frequency. The shift in the resonant wavelengths of the resonator 208 can therefore be monitored to determine if an object 610 has located itself within close proximity to the optical sensor 104 (e.g., the ring resonator 208 and/or a region of the linear waveguide 202 closest to the ring resonator). A binding event, wherein an object 610 binds to the surface of the optical sensor 104 can thus be detected by obtaining the spectral output 212 from the waveguide output 206 and identifying dips in intensity (or peaks in attenuation) therein and the shift of these dips in intensity.

In various embodiments, the waveguide 602, e.g., the linear waveguide 202 and/or the ring resonator 208 comprise silicon. In some embodiments, the surface of the waveguide 602 may be natively passivated with silicon dioxide. As a result, standard siloxane chemistry may be an effective method for introducing various reactive moieties to the waveguide 602, which are then subsequently used to covalently immobilize biomolecules via a range of standard bioconjugate reactions.

Moreover, the linear waveguide 202, ring resonator 208, and/or additional on-chip optics may be easily fabricated on relatively cheap silicon-on-insulator (SOI) wafers using well established semiconductor fabrication methods, which are extremely scalable, cost effective, and highly reproducible. Additionally, these devices may be easily fabricated and complications due to vibration are reduced when compared to "freestanding" cavities. In one example embodiment, 8" SOI wafers may each contain about 40,000 individually addressable ring resonators 208. One advantage of using silicon-based technology is that various embodiments may operate in the Si transparency window of around 1.55 µm, a common optical telecommunications wavelength, meaning that lasers and detectors are readily available in the commercial marketplace as plug-and-play components.

FIGS. 7A and 7B show cross-sectional views of two example waveguides 602, each having a thin layer 702 such as of silicon dioxide on the top of the waveguides 602. In various embodiments, the thickness of thin layer 702 is substantially less than the length of the evanescent field 608, so that, for example, some of the evanescent field reaches the binding site, although thicker or thinner layers are possible. As discussed above, in some cases, this thin layer 702 facilitates deposition of a binding probe layer on the surface of the waveguide sensor 104. This binding probe layer may bind with analytes to be detected. Such a binding event would cause the index of refraction of the waveguide resonator 208 to increase and the resonance frequency thereof to shift in a manner that is detectable by the optical detector 106.

The waveguides 602 in FIGS. 7A and 7B are often referred to as strip and rib waveguides. Other types of waveguides, such as for example, strip-loaded waveguides can be used. Lower cladding 304 lies beneath the waveguides 602. As discussed above, in some embodiments, the waveguides 602 are formed from a silicon-on-insulator chip, wherein the silicon is patterned to form the waveguides 602 and the insulator beneath provides the lower cladding 304. In many of these embodiments, the silicon-on-insulator chip further includes a silicon substrate. Details on the fabrication of silicon biosensor chips can be found in Washburn, A. L., L. C. Gunn, and R. C. Bailey, Analytical Chemistry, 2009, 81(22): p. 9499-9506, and in Bailey, R. C., Washburn, A. L., Qavi, A. J., Iqbal, M., Gleeson, M., Tybor, F., Gunn, L. C. Proceedings of SPIE—The International Society for Optical Engineering, 2009, the disclosures of which are hereby incorporated by reference in their entirety.

Figure 8A:
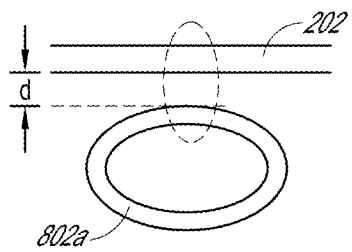
FIGS. 8A and 8B are schematic top views of optical sensors comprising oval-shaped ring resonators.
Figure 8B:
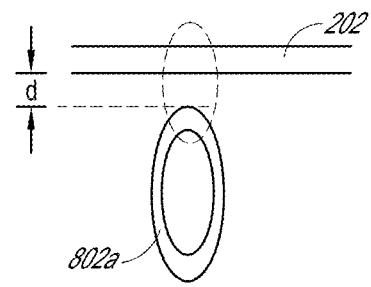

Although circularly-shaped ring resonators have been discussed above, the ring resonator 208 may have other shapes. FIGS. 8A through 8E show various examples of ring resonators 208. Oval or elliptically-shaped ring resonators 802 are illustrated in FIGS. 8A and 8B. In FIG. 8A, the elliptically-shaped resonator 802A has a major axis parallel with the linear waveguide 202. In FIG. 8B, the elliptically-shaped resonator 802B has a minor axis parallel with the linear waveguide 202. The oval or elliptically-shaped resonator 802 can be oriented differently as well.

Figure 8C:
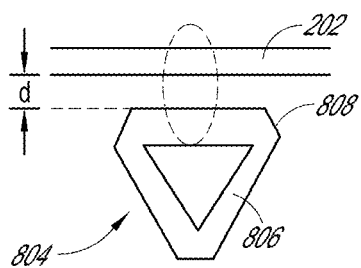
FIG. 8C is a schematic top view of an optical sensor comprising a triangular-shaped ring resonator.

A triangularly-shaped ring resonator 804 is shown in FIG. 8C. The triangularly-shaped ring resonator 804 has three linear segments 806. Three mirrors 808 are also included at the junction between the linear segments 806. Additional segments 806 and mirrors 808 may be added to create different shapes.

Figure 8D:
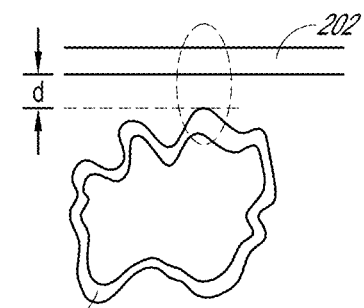
FIG. 8D is a schematic top view of an optical sensor comprising a ring resonator having an irregular shape.

FIG. 8D illustrates a ring resonator 810 having an arbitrary shape. The shape of the resonator can be varied as desired.

In each of FIGS. 8A-8D, the ring resonators 802A, 802B, 804, 810 are shown in proximity to the linear waveguide 202 so as to provide optical coupling therebetween. In some cases for example, the distance, d, separating the linear waveguide 202 and the ring resonator 802A, 802B, 804, 810, is about the size of the evanescent field in the linear waveguide and the evanescent field in the ring resonator at the location where the two waveguide structures are closest. Larger or smaller values may be possible in other cases. Transfer of optical energy is provided via overlap of the evanescent fields.

Figure 8E:
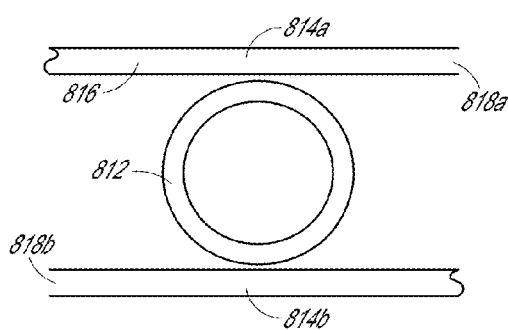
FIG. 8E is a schematic top view of an optical sensor comprising a pair of waveguides having a ring resonator therebetween. This configuration may be referred to as a drop configuration.

FIG. 8E shows a different configuration, which may be referred to as a drop configuration, wherein a ring resonator 812 is disposed between first and second waveguides 814a and 814b. Light (e.g. a wavelength component) may be directed into an input 816 of the first waveguide 814a and depending on the state of the ring resonator 812, may be directed to either an output 818a of the first waveguide 814a or an output 818b of the second waveguide 814b. For example, for resonant wavelengths, the light may be output from the second waveguide 814b instead of the first waveguide 814a. The optical detector 106 may thus monitor shifts in intensity peaks to determine the presence of an analyte of interest detected by the optical sensor 104.

Figure 8F:
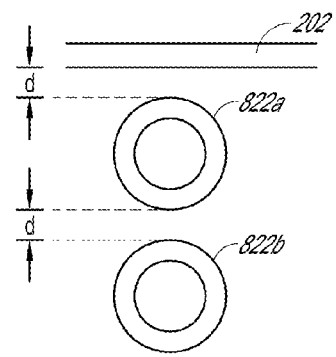
FIG. 8F is a schematic top view of an optical sensor comprising a waveguide and two cascaded ring resonators.

Various embodiments may incorporate more than one ring resonator. FIG. 8F shows an example configuration wherein a first ring resonator 822a and a second ring resonator 822b are employed. In the embodiment shown in FIG. 8F, the first ring resonator 822a and a second ring resonator 822b are cascaded or arranged in a series and in sufficiently close proximity to interact with each other. The first and second ring resonators 822a, 822b are disposed with respect to a linear input/output waveguide 202 such that the first ring resonator 822a is between the input/output waveguide 202 and the second ring resonator 822b. The first ring resonator 822a is a distance d from the linear input/output waveguide 202 so as to be optically coupled together. The second ring resonator 822b is the same distance d from first ring resonator 822a, also so as to be optically coupled together. Light may be coupled from the input/output waveguide 202 into the first ring resonator 822a as in FIGS. 8A-8D, and then into the second ring resonator 822b. In various embodiments, the perimeter of the first ring resonator 822a is equal to the perimeter of the second ring resonator 822b. In some embodiments, a cascade effect is produced when light having a wavelength matching a resonance wavelength of both the first and second ring resonators 822a and 822b is coupled from the input/output waveguide 202 into the first ring resonator 822a and then into the second ring resonator 822b. The optical transmission spectrum, graphed in output plot 214, will include a dip or notch at the resonant wavelength(s). In some embodiments, the cascaded resonators may decrease the width of the dip or notch in the transmission spectrum and provide the output plot 214 with a more "box-like" or "flat" center and possibly steeper falloff in comparison to having the first ring resonator 822a without the second ring resonator 822b. Cascade effects in coupled ring resonators are discussed further in Little, B. E., Chu, S. T., Haus, H. A., Foresi, J., and Laine, J.-P., *Microring Resonator Channel Dropping Filters*, J. Lightwave Technology, 15, 998 (1997), the disclosure of which is hereby incorporated by reference in its entirety.

Although two resonators are shown in FIG. 8F, more ring resonators may be added. Additionally, the ring resonators may be positioned differently with respect to each other as well with respect to the input/output waveguide 202. The resonators may also have different sizes and/or shapes. A drop configuration such as shown in FIG. 8E may also be used instead of having a single input/output waveguide 202. Combinations of these different features are also possible.

Figure 8G:
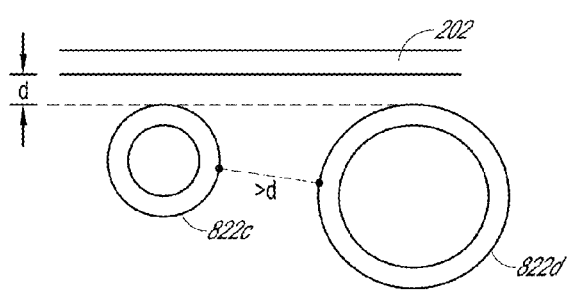
FIG. 8G is a schematic top view of an optical sensor comprising a waveguide and two ring resonators of different size disposed substantially parallel to the waveguide.

FIG. 8G shows an example configuration of an embodiment wherein multiple ring resonators are aligned along the length of and adjacent to the input/output waveguide 202. The first ring resonator 822c is disposed a distance d from the input/output waveguide 202. The second ring resonator 822d is also disposed a distance d from the waveguide 202. Unlike FIG. 8F, the first ring resonator 822c is not disposed between the input/output waveguide 202 and second ring resonator 822d. Similarly, the second ring resonator 822d is not disposed between the input/output waveguide 202 and first ring resonator 822c. Both ring resonators 822c and 822d are disposed in proximity to the input/output waveguide 202, such that light can be coupled from the input/output waveguide to both the ring resonators 822c and 822d without needing to pass through the other ring resonator first. Both ring resonators 822c and 822d are on the same side of the waveguide 202. The first ring resonator 822c is disposed a distance greater than d from the second ring resonator 822d. In various embodiments, this distance greater than d is longer than the evanescent field length 608 such that light is not coupled directly from first ring resonator 822c into second ring resonator 822d, and vice versa. In various embodiments, the perimeter of the first ring resonator 822c is unequal to the perimeter of the second ring resonator 822d. Accordingly, the first ring resonator 822c has a different resonant wavelength(s) than the second ring resonator 822d.

This example configuration may be used in conjunction with a broad spectrum light source, such as a super-luminescent light emitting diode (SLED) or an erbium amplifier running broadband, to simultaneously detect multiple analytes by interrogating the first ring resonator 822c and the second ring resonator 822d simultaneously. The broad spectrum light source emits light that travels through waveguide 202. The first ring resonator 822c may be associated with a first resonant wavelength and a first analyte. The second ring resonator 822d may be associated with second resonant wavelength and a second analyte. The presence of the first analyte may cause a shift in a notch in the transmission spectrum output plot 214 at the first resonant wavelength when bound to the first ring resonator 822c, while the presence of the second analyte may cause a shift in a notch in the absorption spectrum output plot 214 at the second different resonant wavelength when bound to the second ring resonator 822d. Other configurations can be used. For example, a tunable laser or other tunable light source may be used instead of a broadband light source and the wavelength of the output of the tunable laser can be swept. Similarly, the first and second notches in the transmission spectrums of the first and second ring resonators 822c, 822d can be monitored to detect the presence of the first and second analytes respectively.

Although two resonators are shown in FIG. 8G, more ring resonators may be added. Additionally, the ring resonators may be positioned differently with respect to each other as well as with respect to the input/output waveguide 202. For example, the ring resonators may be on opposite sides of the input/output waveguide 202. As discussed above, the resonators may also have different sizes and/or shapes. A drop configuration such as shown in FIG. 8E may also be used instead of having a single input/output waveguide. Combinations of these different features are also possible.

Figure 8H:
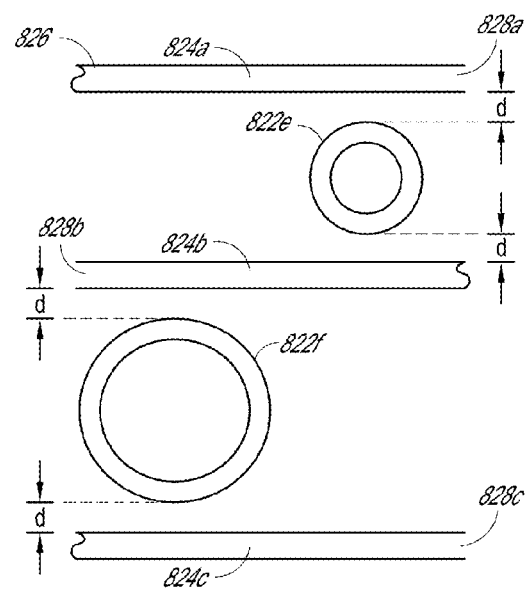
FIG. 8H is a schematic top view of an optical sensor comprising two ring resonators of different size alternated between three substantially parallel linear waveguides.

FIG. 8H depicts an example optical sensor 104 comprising a plurality of ring resonators and a plurality of waveguides that are not ring resonators arranged such that at least one of the ring resonators is between two of the non-ring resonator waveguide structures and at least one of the non-ring resonator waveguide structures is disposed between two of the ring resonators. A first ring resonator 822e is disposed between a first input/output non-ring resonator waveguide 824a and a second "intermediate" non-ring resonator waveguide 824b (both shown as linear waveguides in FIG. 8H). The first ring resonator 822e is disposed a distance d from first waveguide 824a and a distance d from second intermediate waveguide 824b. The optical sensor further comprises a second ring resonator 822f disposed between the second intermediate waveguide 824b and a third "input/output" non-ring resonator waveguide 824c (shown as a linear waveguide in FIG. 8H). The second ring resonator 822f is disposed a distance d from second waveguide 824b and a distance d from third input/output waveguide 824c. In some embodiments, the first and second ring resonators 822e, 822f are offset with respect to each other (e.g., along the length of the waveguides 824a, 824b, 824c).

In various embodiments, light may be directed into an input 826 of the first input/output waveguide 824a, and, depending on the state of the first ring resonator 822e and the wavelength of light, may be directed to either an output 828a of the first waveguide 824a, or may be directed into second waveguide 824b. For example, for the resonant wavelengths of the first ring resonator 822e, the light may be coupled into the second waveguide 824b instead of being output from the first waveguide 824a at output 828a. Light coupled into the second waveguide 824b from the first ring resonator 822e is directed to either an output 828b of the second waveguide 824b or into the third waveguide 824c, depending on the state of the third ring resonator 822f. For example, for the resonant wavelengths of the third ring resonator 822f, the light may be coupled into the third waveguide 824c and then output at output 828c. In the case where the light source that directs light into the first input/output waveguide 826 comprises a broadband light source such as a super-luminescent diode that outputs a broadband spectrum, the light referred to above may be a wavelength component of the broader spectrum.

In various embodiments, the perimeter of the first ring resonator 822e is unequal to the perimeter of the second ring resonator 822f, such that the Free Spectral Range (FSR) of the first ring resonator 822e is slightly different from the FSR of the second ring resonator 822f. In various embodiments, this configuration can produce Vernier effects. Light directed into the input 826 can pass through both the first ring resonator 822e and the second ring resonator 822f if it is of a resonant wavelength common to both the first ring resonator 822e and the second ring resonator 822f. Two resonators with slightly different FSRs have a large combined FSR, as their common resonant wavelengths are highly separated in the wavelength spectrum. Accordingly, the passbands transmitted from input 826 to output 828c by this configuration are relatively far apart in the wavelength spectrum as these passbands coincide with the common resonant wavelengths of first ring resonator 822e and second ring resonator 822f. Additionally, embodiments of this configuration may have relatively narrow passband bandwidths. Optical Vernier effects are also discussed in Schwelb, O., *The Vernier Principle in Photonics,* 2011, the disclosure of which is hereby incorporated by reference in its entirety.

Other configurations can be used. A tunable laser or other tunable light source may be used as the input source and the wavelength of the output of the tunable laser can be swept. Alternatively, a broadband light source such as a superluminescent diode may be used.

More ring resonators may be added. Additionally, the ring resonators may be positioned differently with respect to each other as well as with respect to the input/output waveguide 202. Likewise, more non-ring resonator waveguides may be added. As discussed above, the resonators may also have different sizes and/or shapes. In some embodiments, the third output 828c or last non-ring resonator waveguide 824c may be excluded. Combinations of these different features are also possible.

Still other designs than those shown in FIGS. 8F-8H may be employed. Multiple resonators and/or waveguides may be placed in any desired geometric arrangement. Additionally, spacing between resonators and/or waveguides may be varied as desired. Different features from FIG. 8A-8H can be combined in different ways. Still other configurations are possible Other geometries may possibly be used for the resonator, such as, for example, microsphere, microdisk, and microtoroid structures. See, e.g., Vahala, *Nature* 2003, 424, 839-846; and in Vollmer & Arnold, *Nature Methods* 2008, 5, 591-596, the disclosures of which are hereby incorporated by reference in their entirety.

Also, although linear waveguides 202 are shown in FIGS. 8A-8G as providing access to the ring resonators 208 such as those shown by 802a, 802b, 804, 810, 812, 822a, 822c, and 822d, these waveguides need not be restricted to plain linear geometry. In some examples, for instance, these waveguides 202 may be curved or otherwise shaped differently.

Various embodiments of ring resonators and possibly other geometries repeatedly circulate light around, for example, their perimeter, dramatically increasing the optical path length. Furthermore, interference between photons circulating in the structure and those traversing the adjacent waveguide create a resonant cavity of extraordinarily narrow spectral linewidth resulting in a high-Q device. The resulting resonance wavelengths are quite sensitive to changes in the local refractive index. As discussed herein, this sensitivity enables the sensors to detect small masses.

In various embodiments as described herein, beads and other particles may be used to provide an amplifying effect on the signal. Other techniques such as those described herein may also be used to provide amplifying effects.

Figure 9:
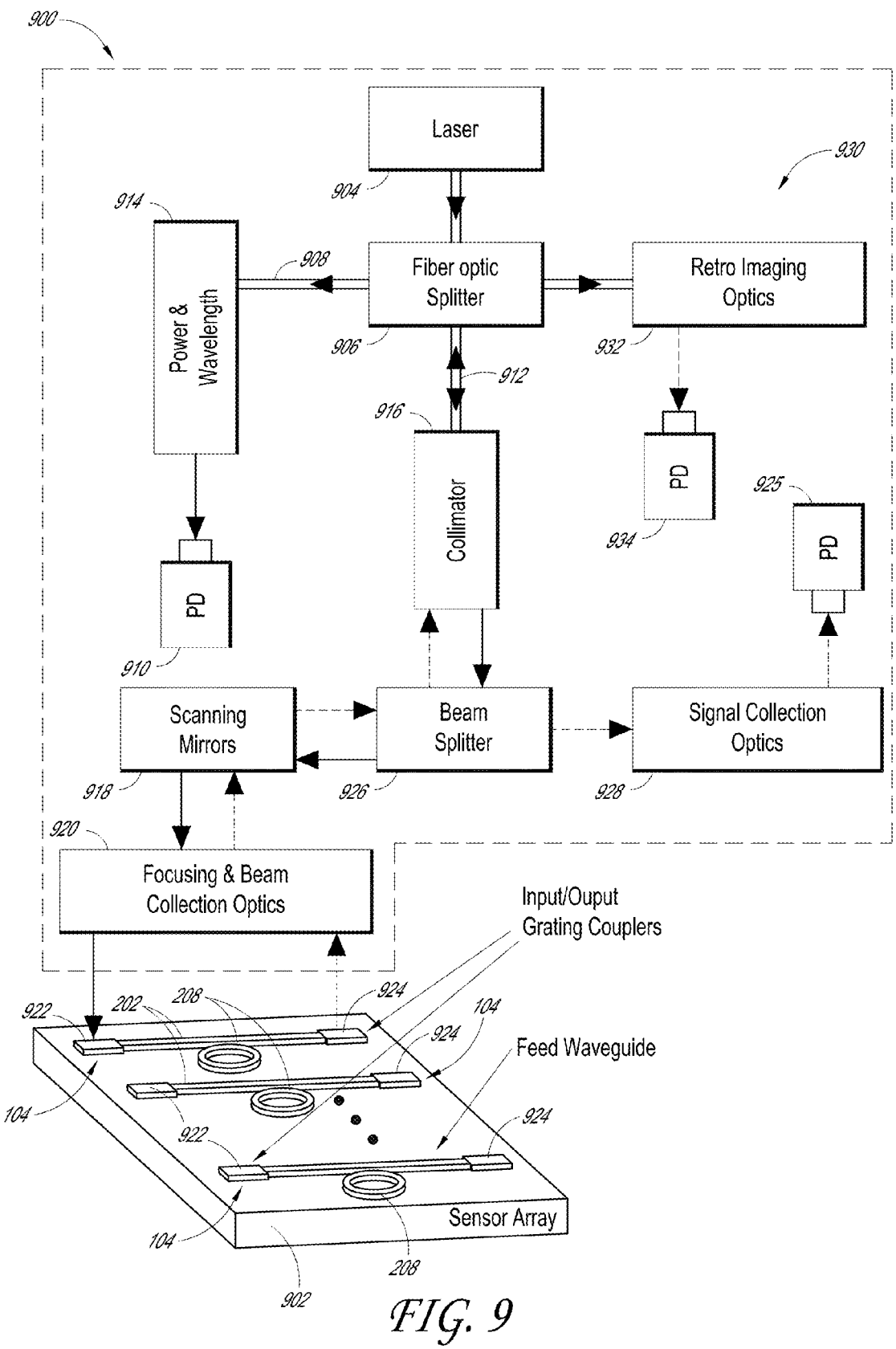
FIG. 9 schematically illustrates a plurality of optical sensors on a chip and an apparatus that provides light to the chip and detects light output from the chip.

One embodiment of an apparatus 900 for interrogating the optical sensors 104 on a chip 902 is schematically illustrated in FIG. 9. The apparatus 900 includes a laser light source 904, which may comprise a tunable laser. The apparatus 900 further comprises a splitter 906 that directs light from the laser 904 along a first path 908 to a photodetector 910 for calibration and along a second path 912 toward the chip 902. A static Fabry-Perot cavity or other wavelength resolving device 914 may be included in the first path 908 to the photodetector 910 such that the photodetector 910 can measure the relative power for different wavelengths of the light output by the laser 904 and presumably provided to the optical sensors 104. The wavelength resolving device 914 may establish a reference wavelength that is known to be output from the light source at a specific time. By additionally knowing the rate at which the wavelengths are swept, the wavelength output by the light source at different times is can be determined. Beam shaping optics, such as a collimator 916, may be included in the second optical path 912 to adjust the shape of the beam as desired. This beam is directed to scanning mirrors 918 such that the beam may be scanned across the chip 902. Focusing optics 920 are included to focus the beam onto the chip 902.

The chip 902 includes input couplers 922 configured to couple the beam propagating in free space into the waveguides 202 on the chip. These input couplers 922 may comprise for example waveguide gratings that use diffraction to couple the light beam propagating down toward the chip 902 into optical modes that propagate along the waveguides 922 on the chip. As shown, the chip 902 includes a plurality of optical sensors 104 each comprising linear waveguides 202 and ring resonators 208. The chip 902 additionally includes output couplers 924 that may also comprise waveguide gratings. These grating couplers 924 similarly use diffraction to couple light propagating in optical modes within the waveguides 202 out into free space. Accordingly, light may be injected into the linear waveguides 202 via an input coupler 922 and extracted therefrom via an output coupler 924. As described above, the ring resonators 208 may modulate this light, for example, shifting a wavelength feature such as the spectral valley at the resonance wavelength of the ring resonator, depending on whether an object 610 is in proximity of the resonator.

Light from the output couplers 924 is collected by collection optics. The focusing optics 920 can double as the collection optics. Alternatively, separate collection optics may used.

The optical detector 106 (comprising a photodetector 925 in FIG. 9) may be included in the apparatus 900 to detect the light collected from the chip 902. In some embodiments such as illustrated in FIG. 9, light from the output coupler 924 travels to the photodetector 925 via the collection optics 920, the scanning mirrors 918 as well as a beam-splitter 926 and signal collection optics 928. The scanning mirrors 918 can be scanned so as to direct light collected from different output couplers 924 and hence different optical sensors 104 at different locations on the chip 902.

The apparatus 900 may further comprise an imaging system 930 comprising imaging optics 932 and an image sensor 934. In some embodiments, this image sensor 934 may comprise a single detector that forms an image by recording the detected signal as the scanning mirrors 918 scan the chip. In some embodiments, this image sensor 934 may comprise a detector array such as a CCD or CMOS detector array. Light from the chip 902 is collected by the collection optics and propagates to the imaging system 930 via the scanning mirrors 918, the beam-splitter 926 (that directs a portion of the light from the output coupler 924 to the detector 106), the collimation optics 916, and the splitter 906 (that also directs light from the laser 904 to the chip). The imaging optics 930 may be used to image the chip 902 and facilitate identification of which optical sensor 104 is being interrogated at a given time. Other configurations are possible.

Figure 10:
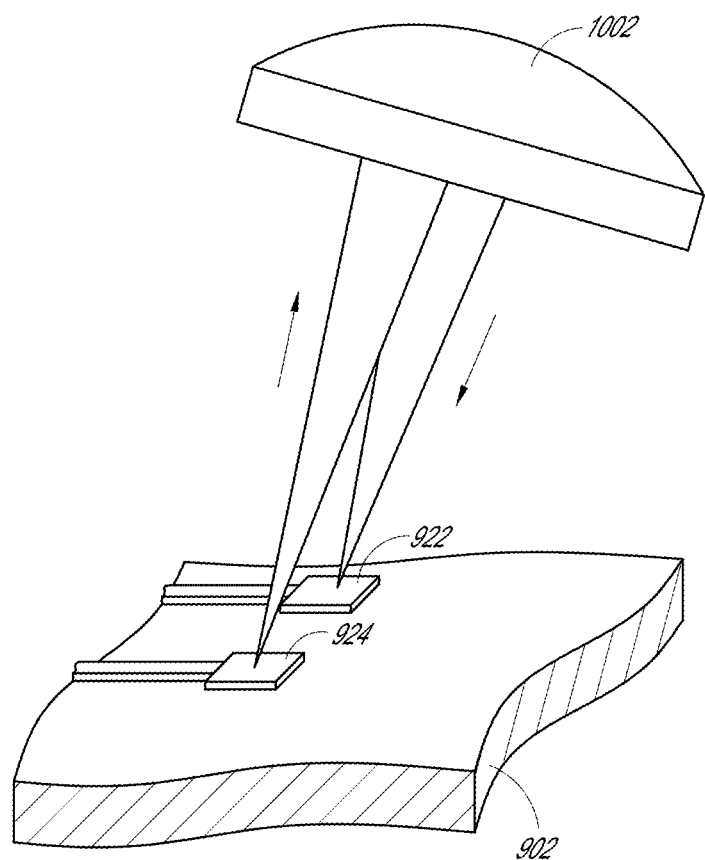
FIG. 10 is a perspective view of light coupled into a waveguide on a chip using a grating coupler and light coupled out of a waveguide on a chip using a grating coupler, for example, to provide input to and collect output from an optical sensor on the chip.

FIG. 10 shows an example of an objective lens 1002 that operates as the focusing and beam collection optics 920. As illustrated, light is directed into the input coupling element 922 and returned from the output coupling element 924. As illustrated, some embodiments that use grating couplers 922 and 924, which couple free space light into the on-chip optical elements, eliminate the need for any physical connection between the interrogation apparatus 900 and the chip 902.

Apparatus 900 for interrogating the chip 902 are illustrated in PCT Publication WO 2010/062627 titled Biosensors Based on Optical Probing and Sensing", which entered the national stage as U.S. application Ser. No. 13/126,164 and which published as U.S. Patent Publication No. 2012/0092650 on Apr. 19, 2012, each of which are incorporated herein by reference in their entirety.

The system may vary. For example, instead of using a swept light source, such as a tunable laser, a broadband light source such as a super-luminescent diode may be employed.

Figure 11:
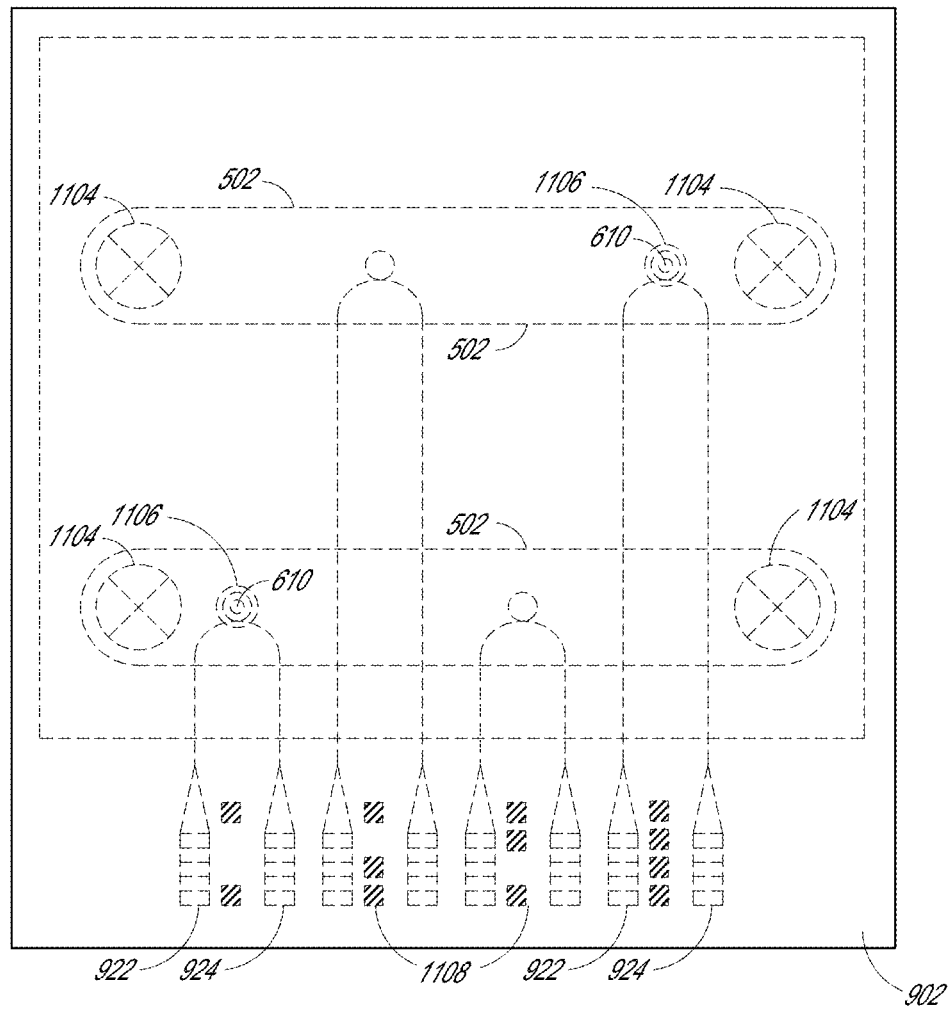
FIG. 11 is a top view schematically illustrating a chip having input and output couplers connected to waveguide optical sensors comprising ring resonators. The chip further includes flow channels for flowing solution across the waveguide optical sensors and in particular the ring resonators. Input ports provide access to the flow channels. The chip further comprises identification markers to facilitate identification of the different optical sensors.

An example chip 902 is schematically illustrated in FIG. 11. The chip 902 includes input and output couplers 922, 924, ring resonators 208 and the respective waveguides 202 optically coupled thereto. The chip 902 further includes flow channels 502 configured to direct flow of solution 108 across the optical sensors 104, e.g., the ring resonators 208 and proximal portions of the waveguides 202 optically coupled thereto. Ports 1104 for accessing the flow channels 502 are also included to flow the solution 108 into and out of the flow channels 502.

FIG. 11 shows some 1106 of the optical sensors 104 as having an object 610 from the solution 108 coupled to the ring resonators 208. As discussed above, these optical sensors 1106 will have an optical output indicating this event, such as a shift in the spectral feature at the resonance wavelength of the ring resonator 208.

The chip 902 further includes identification markers 1108 for separately identifying the different optical sensors 104. In some example embodiments, identification of the optical sensors 104 is accomplished using the imaging system 930 shown in FIG. 9, which images and/or collects light from the identification markers 1108. In some embodiments, the identification markers 1108 have unique signatures. Additionally, in some embodiments, the identification markers 1108 are diffractive optical elements. In some embodiments, grating couplers 922 and 924 may be placed in a distinct pattern that allows the unique identification of each optical sensor 104. Accordingly, in such embodiments, separate identification markers 1108 need not be included. Other techniques can also be used for identifying the sensors.

One example embodiment of a biosensor chip 902 may be manufactured as follows. Microring resonator arrays can be fabricated on 8" silicon-on-insulator wafers having, e.g., a top-layer of silicon, from which about 600 individual chips 902 are diced. Each chip 902 has sixty-four ring resonators 208 having 30 µm diameters on a 6×6 mm footprint. Next to each ring resonator 208 is a linear waveguide 202 that has an input diffraction grating coupler 922 and an output diffractive grating coupler 924 at either end, allowing the optical cavity spectrum of each ring resonator 208 to be determined independently.

In various embodiments, the surface of each chip 902 is uniformly coated with a commercially-available perfluoro (alkenyl vinyl ether) copolymer cladding material with windows 404 opened over selected individual sensor elements via photolithography and reactive ion etching. This cladding material can serve three purposes: 1) to confine biomolecule attachment to the active sensing areas of the chip 902, 2) to reduce the non-specific binding of biomolecules across the surface of the entire chip 902, which might otherwise deplete low abundance targets, and 3) to occlude some ring resonators 208 (those not revealed in the etching step) such that these resonators are not exposed to the solution 108, enabling these resonators to be used as controls, for example, for thermal drift.

Sensitivity metrics may be used to compare different types of optical biosensors. For example, using saline solution standards the bulk refractive index sensitivity of an embodiment of this platform was measured to be $7.6 \times 10^{-7}$ refractive index units (RIUs). Using a controllable polyelectrolyte multilayer growth scheme, the 1/e evanescent field decay length for one embodiment of a high index contrast ring resonators 208 was determined to be 63 nm. Additional discussion can be found in (a) Iqbal, M; Gleeson, M A; Spaugh, B; Tybor, F; Gunn, W G; Hochberg, M; Baehr-Jones, T; Bailey, R C; Gunn, L C, Label-Free Biosensor Arrays based on Silicon Ring Resonators and High-Speed Optical Scanning Instrumentation. *IEEE J. Sel. Top. Quantum Electron* 2010, 16, 654-661 as well as Luchansky, M S; Washburn, A L; Martin, T A; Iqbal, M; Gunn, L C; Bailey, R C. Characterization of the evanescent field profile and bound mass sensitivity of a label-free silicon photonic microring resonator biosensing platform. *Biosens. Bioelectron.* 2010, doi:10.1016/j.bios.2010.1007.1010, the disclosures of which are hereby incorporated by reference in its entirety. Using a modified radioimmunoas say the surface sensitivity of some sensors 104 was determined to be ~1 pg/mm$^2$.

An example apparatus 900 for interrogating the chip 902 having an array of biosensors 104 may include laser 904 comprising a tunable, external cavity diode laser operating with a center wavelength of 1560 nm. A beam from the laser 904 is focused onto a single input grating coupler 922 and rapidly swept through a suitable spectral bandwidth. The light coupled into the input grating coupler 922 is output by the corresponding output grating coupler 924 and is measured. Resonances are measured as wavelengths at which the intensity of light coupled out of the output coupler manifest a notch feature. The different ring resonators 208 in the array may be serially interrogated. However, high tuning rate (e.g., kHz) lasers 904 and fast scan mirrors 918 may allow resonance wavelengths and shifts in wavelength to be determined in near real time with up to 250 ms temporal resolution. In this embodiment, up to 32 optical sensors 104 can be monitored simultaneously during an experiment. Any number of the sensors 104 may be left covered by the fluoropolymer cladding and thus may not be exposed to the solution 108 and serve as controls for thermal drift. On-chip and real-time drift compensation can increase sensitivity as temperature dependent refractive index modulations can obscure biomolecular binding events. On-chip referencing is an effective method of compensating for this source of noise. Additional discussion is included in Iqbal, M; Gleeson, M A; Spaugh, B; Tybor, F; Gunn, W G; Hochberg, M; Baehr-Jones, T; Bailey, R C; Gunn, L C, Label-Free Biosensor Arrays based on Silicon Ring Resonators and High-Speed Optical Scanning Instrumentation. *IEEE J. Sel. Top. Quantum Electron* 2010, 16, 654-66, the disclosure of which is hereby referenced in its entirety.

Additional details regarding sensors and apparatus for interrogating such sensors are included in U.S. Patent Publication 2011/0045472 titled "Monitoring Enzymatic Process" as well as PCT Publication WO 2010/062627 titled "Biosensors Based on Optical Probing and Sensing", which entered the national stage as U.S. application Ser. No. 13/126,164 and which published as U.S. Patent Publication No. 2012/0092650 on Apr. 19, 2012. Each of these documents is incorporated herein by reference in their entirety.

A wide range of variations, however, are possible. For example, In some embodiments, a ring resonator 208 may be spectrally interrogated by means of a broadband light source, such as a superluminescent light emitting diode (SLED) or erbium amplifier running broadband, that produces light having a range of wavelengths all at once, e.g. injecting light across the input spectrum 210 into waveguide input 204. Likewise, a spectral analyzer (e.g., comprising a spectrometer) may be used to collect light from waveguide output 206 and analyze output spectrum 212.

Analytes of Interest

The term "analyte" as used herein refers to the substance to be detected that may be present in a test sample. Analytes of interest include, but are not limited to polypeptides, nucleic acids, carbohydrates, and antibodies. As used herein with respect to analytes of interest, "nucleic acids" refer to deoxyribonucleic acid (DNA, such as cDNA or genomic DNA) or ribonucleic acid (RNA). As used herein with respect to analytes of interest, "polypeptides" refer to peptides of any amino acid length, which is inclusive of any kind of protein, such as peptide hormones, enzymes and antibodies.

In several embodiments, an analyte of interest is considered a biomarker. The term biomarker commonly refers to a biomolecule useful for diagnosing or determining the presence, absence, status, stage, or risk of developing a particular disease or condition. Generally, biomarkers are differentially present in samples taken from at least two groups of subjects that differ in health status and can be present at an elevated or decreased level in samples of a first group as compared to samples of a second group.

In various embodiments, an analyte of interest comprises a ribonucleic acid (RNA). Examples of RNA analytes of interest include, but are not limited to, messenger RNAs (mRNAs), mRNA splice variants, antisense RNAs, transfer RNAs (tRNAs), ribosomal RNAs (rRNAs), small nuclear RNAs (snRNAs), small nucleolar RNAs (snoRNAs), small interfering RNAs (siRNAs), tiny non-coding RNAs (tncRNAs), repeat-associated small interfering RNAs (rasiRNAs), and microRNAs (miRNAs), and precursor forms of such RNAs.

miRNAs are also known as microRNAs, Mirs, miRs, mirs, and mature miRNAs, and generally refer either to double-stranded intermediate molecules around 17 to about 25 nucleotides in length, or to single-stranded miRNAs, which may comprise a bulged structure upon hybridization with a partially complementary target nucleic acid molecule.

MicroRNAs (miRNAs) are small non-coding RNA molecules encoded in the genomes of plants and animals. In certain instances, highly conserved, endogenously expressed miRNAs regulate the expression of genes by binding to the 3'-untranslated regions (3'-UTR) of specific mRNAs. More than 1000 different miRNAs have been identified in plants and animals. Certain mature miRNAs appear to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670). Examples of precursor forms of miRNAs include, but are not limited to, primary miRNA transcripts (also known as pri-pre-miRNAs, pri-mirs, pri-miRs and pri-miRNAs, which range from around 70 nucleotides to about 450 nucleotides in length and often taking the form of a hairpin structure); and pre-miRNAs (also known as pre-mirs, pre-miRs and foldback miRNA precursors, which range from around 50 nucleotides to around 110 nucleotides in length).

Without being bound by theory, the current model of miRNA processing involves primary miRNA transcripts being processed by a nuclear enzyme in the RNase III family known as Drosha, into approximately 70 nucleotide-long pre-miRNAs which are subsequently processed by the Dicer RNase into mature miRNAs, approximately 21-25 nucleotides in length. It is believed that, in processing pri-miRNA into the pre-miRNA, the Drosha enzyme cuts pri-miRNA at the base of the mature miRNA, leaving a 2-nt 3' overhang (Ambros et al., RNA, 2003, 9, 277-279; Bartel and Bartel, Plant Physiol., 2003, 132, 709-717; Shi, Trends Genet., 2003, 19, 9-12; Lee, et al., EMBO J., 2002, 21(17), 4663-4670; Lee, et al., Nature, 2003, 425, 415-419). The 3' two-nucleotide overhang structure, a signature of RNaseIII cleavage, has been identified as a specificity determinant in targeting and maintaining small RNAs in the RNA interference pathway (Murchison, et al., Curr. Opin. Cell. Biol., 2004, 16, 223-9). Both the primary RNA transcripts (pri-miRNAs) and foldback miRNA precursors (pre-miRNAs) are believed to be single-stranded RNA molecules with at least partial double-stranded character, often containing smaller, local internal hairpin structures.

As used herein, a "sample" or "test sample" can include, but is not limited to, biological material obtained from an organism or from components of an organism. The test sample may be of any biological tissue or fluid, for example. In some embodiments, the test sample can be a clinical sample derived from a patient. Examples of test samples include, but are not limited to sputum, cerebrospinal fluid, blood, blood fractions such as serum and plasma, blood cells, tissue, biopsy samples, urine, peritoneal fluid, pleural fluid, amniotic fluid, vaginal swab, skin, lymph fluid, synovial fluid, feces, tears, organs, or tumors. A test sample can also include recombinant cells, cell components, cells grown in vitro, and cell culture constituents including, for example, conditioned medium resulting from the growth of cells in cell culture medium.

Capture Probes

In several embodiments, capture probes are attached to a surface of an optical sensor, such as an optical ring resonator. As used herein, a "capture probe" is any molecule that can be used to bind to an analyte of interest.

Without being bound by theory, the resonance wavelengths on the optical sensor are sensitive to the local refractive index. Biomolecular binding events that increase the refractive index at the sensor surface can be observed as an increase in the resonance wavelength of the optical sensor. Accordingly, binding of an analyte of interest to a capture probe attached to a surface of an optical sensor represents a "primary" binding event that can be detected and/or measured in terms of an increase in the resonance wavelength of the optical sensor of various embodiments.

Suitable examples of capture probes include, but are not limited to, nucleic acids (e.g. deoxyribonucleic acids and ribonucleic acids), polypeptides (e.g. proteins and enzymes), antibodies, antigens, and lectins. As will be appreciated by one of ordinary skill in the art, any molecule that can specifically associate with an analyte of interest can be used as a capture probe. In certain embodiments, the analyte of interest and capture probe represent a binding pair, which can include but is not limited to antibody/antigen (e.g., nucleic acid or polypeptide), receptor/ligand, polypeptide/nucleic acid, nucleic acid/nucleic acid, enzyme/substrate, carbohydrate/lectin, or polypeptide/polypeptide. It will also be understood that binding pairs of analytes of interest and capture probes described above can be reversed in several embodiments (e.g. in one embodiment an antibody that specifically binds to an antigen can be the analyte of interest and the antigen can be the capture probe, whereas in another embodiment the antibody can be the capture probe and the antigen can be the analyte of interest).

The following classes of molecules can be used as capture probes in various embodiments. It will be understood that such classes of molecules are examples only and are not intended to be exhaustive or limiting.

1. Nucleic Acid Capture Probes

In some embodiments, the capture probe attached to a surface of an optical sensor can comprise a nucleic acid and is referred to as a nucleic acid capture probe. As used herein with respect to capture probes, "nucleic acid" refers to deoxyribonucleic acid (DNA) or ribonucleic acid (RNA) and known analogs, derivatives, or mimetics thereof. A nucleic acid capture probe can be oligomeric and include oligonucleotides, oligonucleosides, oligonucleotide analogs, oligonucleotide mimetics and chimeric combinations of these. A nucleic acid capture probe can be single-stranded, double-stranded, circular, branched, or hairpin and can contain structural elements such as internal or terminal bulges or loops.

In some embodiments, a nucleic acid capture probe can have a length of at least, or at least about 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleobases, or the nucleic acid capture probe can have a length within any range bounded by two of the above-mentioned lengths.

In several embodiments, a nucleic acid capture probe and a nucleic acid analyte of interest bind to form a duplex. Such binding may occur through hybridization. As used herein, "hybridization" means the pairing of complementary strands of a nucleic acid capture probe and a nucleic acid analyte of interest. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of a nucleic acid capture probe and nucleic acid analyte of interest.

In some embodiments, a nucleic acid capture probe and nucleic acid molecule of interest can hybridize under "stringent conditions," which refer to conditions under which a nucleic acid capture probe will hybridize to a nucleic acid molecule of interest, but to a minimal number of other sequences. A person of ordinary skill in the art will appreciate that stringent conditions are sequence-dependent and will vary in different circumstances. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

"Complementarity," as used herein, refers to the capacity for precise pairing between two nucleobases of a nucleic acid capture probe and nucleic acid analyte of interest. For example, if a nucleobase at a certain position of a capture probe is capable of hydrogen bonding with a nucleobase at a certain position of a nucleic acid analyte of interest, then the position of hydrogen bonding between the capture probe and the nucleic acid analyte of interest is considered to be a complementary position. The capture probe and the analyte of interest are complementary to each other when a sufficient number of complementary positions in each molecule are occupied by nucleobases which can hydrogen bond with each other. Thus, in some embodiments a nucleic acid capture probe and nucleic acid analyte of interest are specifically hybridizable and complementary, which indicate a sufficient degree of precise pairing or complementarity over a sufficient number of nucleobases such that stable and specific binding occurs.

It will be appreciated that the sequence of a nucleic acid capture probe need not be 100% complementary to that of a nucleic acid analyte of interest to be specifically hybridizable. Moreover, a nucleic acid capture probe may hybridize over one or more segments such that intervening or adjacent segments are not involved in the hybridization event (e.g., a loop structure, mismatch or hairpin structure). The nucleic acid capture probes of several embodiments can comprise at least 70%, or at least 75%, or at least 80%, or at least 85%, or at least 90%, or at least 92%, or at least 95%, or at least 97%, or at least 98%, or at least 99% sequence complementarity to a region within the nucleic acid sequence of the analyte of interest. The degree of complementarity to be specifically hybridizable can be selected according to well-known principles of hybridization and in accordance with the intended analytical procedure.

In several embodiments, a nucleic acid capture probe can comprise one or more oligonucleotide mimetics. The term "mimetic" includes oligomeric nucleic acids wherein the furanose ring or the furanose ring and the internucleotide linkage are replaced with non-naturally occurring groups.

In certain embodiments, a nucleic acid capture probe comprises a peptide nucleic acid (PNA) oligonucleotide mimetic (Nielsen et al., Science, 1991, 254, 1497-1500). PNAs have favorable hybridization properties, high biological stability and are electrostatically neutral molecules. In PNA oligonucleotide mimetics, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA oligomeric compounds include U.S. Pat. Nos. 5,539,082; 5,714,331 and 5,719,262. PNA compounds can be obtained commercially from Applied Biosystems (Foster City, Calif., USA). Numerous modifications to the basic PNA backbone are known in the art and can be used in several embodiments.

Another class of oligonucleotide mimetic that can be used for nucleic acid capture probes in several embodiments is linked morpholino units (morpholino nucleic acid) having heterocyclic bases attached to the morpholino ring. A number of linking groups have been reported that link the morpholino monomeric units in a morpholino nucleic acid. Morpholino-based oligomeric compounds are non-ionic mimetics of oligonucleotides which are less likely to form undesired interactions with cellular proteins (Dwaine A. Braasch and David R. Corey, Biochemistry, 2002, 41(14), 4503-4510). The morpholino class of oligomeric compounds has been prepared with a variety of different linking groups joining the monomeric subunits.

A further class of oligonucleotide mimetic that can be used for nucleic acid capture probes in several embodiments is cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes.

In several embodiments, a nucleic acid capture probe can comprise a locked nucleic acid (LNA), which can increase the sensitivity and specificity of conventional oligonucleotides, such as DNA oligonucleotides, for hybridization to short target sequences such as mature miRNAs, stem-loop precursor miRNAs, pre-miRNAs, siRNAs or other non-coding RNAs as well as miRNA binding sites in their cognate mRNA targets, mRNAs, mRNA splice variants, RNA-edited mRNAs, antisense RNAs and small nucleolar RNAs (snRNA).

Locked nucleic acid (LNA) capture probes are nucleoside or nucleotide analogues that include at least one LNA monomer (e.g., an LNA nucleoside or LNA nucleotide). LNA monomers are described in, for example, WO 99/14226, U.S. Pat. No. 6,043,060, U.S. Pat. No. 6,268,490, WO 01/07455, WO 01/00641, WO 98/39352, WO 00/56746, WO 00/56748 and WO 00/66604. LNAs have bicyclic sugar moieties "in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630).

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

In several embodiments, a nucleic acid capture probe can include a non-native, degenerate, or universal base such as inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine, or the like. In some embodiments, a nucleic acid capture probe can include isocytosine and/or isoguanine in order to reduce non-specific hybridization as generally described in U.S. Pat. No. 5,681,702.

In several embodiments, a nucleic acid capture probe can comprise an "aptamer" to bind to a nucleic acid or polypeptide analyte of interest. Aptamers are described in U.S. Pat. Nos. 5,270,163; 5,475,096; 5,567,588; 5,595,877; 5,637,459; 5,683,867; and 5,705,337; which are herein incorporated by reference in their entireties. Aptamers can bind to various molecular targets such as small molecules, proteins, and nucleic acids.

2. Polypeptide Capture Probes

In several embodiments, a capture probe attached to a surface of an optical sensor can comprise a polypeptide, which is inclusive of known polypeptide analogs. Examples of polypeptide analogs include molecules that comprise a non-naturally occurring amino acid, side chain modification, backbone modification, N-terminal modification, and/or C-terminal modification known in the art. For example, a polypeptide capture probe can comprise a D-amino acid, a non-naturally occurring L-amino acid, such as L-(1-naphthyl)-alanine, L-(2-naphthyl)-alanine, L-cyclohexylalanine, and/or L-2-aminoisobutyric acid.

In several embodiments, a polypeptide capture probe can comprise an antigen to which an antibody analyte of interest is capable of binding. In various aspects, a capture probe can comprise a polypeptide antigen capable of binding to an antibody of interest that is a known biomarker for a particular disease or condition. It will be appreciated that a capture probe of the systems provided herein can comprise any antigen associated with any disease or condition for which a subject's antibody against the antigen is considered a biomarker. As a non-limiting example, a capture probe can comprise a viral antigen capable of binding to an antibody specific against the viral antigen. Presence of such an antibody, as detected by the systems provided herein, would indicate that the subject has been infected by the virus and mounted a specific immune response to it. In certain embodiments, a capture probe can comprise an auto-antigen associated with an autoimmune disorder or an antigen associated with an allergy, which capture probe is capable of binding to an antibody, such as an auto-antibody, of interest. Presence of such an antibody, as detected by the systems provided herein, would indicate that the subject has or is at risk of having the associated autoimmune disorder or allergy.

3. Lectin Capture Probes

In various embodiments wherein the analyte of interest is a carbohydrate, suitable capture probes can include lectins. Lectins are proteins that bind to saccharides and differ in the types of carbohydrate structures they recognize. Several known lectins that can be used in capture probes of various embodiments include those that have been isolated from plants including *Conavalia ensiformis, Anguilla anguilla, Triticum vulgaris, Datura stramoniuim, Galanthus nivalis, Maackia amurensis, Arachis hypogaea, Sambucus nigra, Erythrina cristagalli, Lens culinaris, Glycine may, Phaseolus vulgaris, Allomyrina dichotoma, Dolichos biflorus, Lotus tetragonolobus, Ulex europaeus,* and *Ricinus communis*. Additional lectins that can be used in capture probes of several embodiments include any of the animal, bacterial, or fungal lectins known in the art. Several bacterial and fungal lectins have considerably high affinity (micromolar Kd) towards carbohydrates compared to plant or animal lectins.

4. Antibody Capture Probes

In some embodiments, a system for detecting the presence of an analyte of interest includes a capture probe comprising an antibody attached to a surface of an optical sensor. In several embodiments, a capture probe comprising an antibody, referred to herein as an "antibody capture probe," is capable of specifically binding a polypeptide analyte of interest. As used herein, the term "antibody" includes, but is not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above.

The antibodies of several embodiments provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147: 60-69 (1991); U.S. Pat. Nos. 4,474,893; 4,714,681; 4,925,648; 5,573,920; 5,601,819; Kostelny et al., J. Immunol. 148:1547-1553 (1992); each of which is incorporated herein by reference in its entirety.

Several embodiments are drawn to systems for detecting an analyte of interest that is a known biomarker for a particular disease or condition. In some aspects, the biomarker analyte of interest is a miRNA, overexpressed or underexpressed mRNA, or polypeptide associated with a particular disease or condition. Presence of such a biomarker, as detected by the systems provided herein, would indicate that the subject has the disease or condition associated with the biomarker.

Attachment of Capture Probes to Optical Sensor Surface

In several embodiments, the capture probes are attached to a surface of an optical sensor by a linkage, which may comprise any moiety, functionalization, or modification of the binding surface and/or capture probes that facilitates the attachment of the capture probes to the surface of the optical sensor. The linkage between the capture probes and the surface of the optical sensor can comprise one or more chemical bonds; one or more non-covalent chemical bonds such as Van der Waals forces, hydrogen bonding, electrostatic interaction, hydrophobic interaction, or hydrophilic interaction; and/or chemical linkers that provide such bonds.

In certain embodiments, the optical sensor surface can have a protective or passivating layer to reduce or minimize attachment of molecules other than the capture probes. For example, the optical sensor surface can be protected or passivated to reduce attachment of analyte molecules that could otherwise cause false a positive signal or loss of signal. Examples of suitable protective or passivating layers include, but are not limited to polymers, such as polyethylene glycol (PEG); proteins that block nonspecific binding, such as serum albumin and casein; surfactants, such as betaines; carrier nucleic acids, such as salmon sperm DNA; and silicon dioxide.

In several embodiments, the capture probes can be attached to a surface of the optical sensor through the use of reactive functional groups on the capture probes and the surface. For example, a capture probe can be attached to a surface of an optical sensor without a linker by derivatizing the surface with a functional group and contacting the derivatized surface with capture probes.

The functional groups can be functional chemical moieties. For example, the surface of the optical sensor can be derivatized such that a chemical functional group on the surface can react with a chemical functional group on the capture probe resulting in attachment. Examples of functional groups include, but are not limited to, amino, hydroxyl, carboxyl, carboxylate, aldehyde, ester, ether (e.g. thio-ether), amide, amine, nitrile, vinyl, sulfide, sulfonyl, siloxanes, phosphoryl, oxo, thiol, or similar chemically reactive functional groups. Additional moieties that can be used as functional groups to attach capture probes to a surface of an optical sensor include, but are not limited to, maleimide, N-hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene, biotin and avidin.

In several embodiments, a capture probe can be attached to the surface of the optical sensor through a linker, which is often referred to as a crosslinker. Any suitable crosslinker known in the art can be used to attach capture probes to a surface of the optical sensor. Non-limiting examples of crosslinkers suitable for use in several embodiments include alkyl groups (including substituted alkyl groups and alkyl groups containing heteroatom moieties), esters, amide, amine, epoxy groups, ethylene glycol, and derivatives. A crosslinker may also comprise a sulfone group, forming a sulfonamide. In some embodiments, a sulfhydryl linker can be used, such as SPDP, maleimides, α-haloacetyls, and pyridyl disulfides (see for example the 1994 Pierce Chemical Company catalog, technical section on cross-linkers, pages 155-200, incorporated herein by reference) which can be used to attach cysteine containing polypeptides to the surface of an optical sensor. An amino group on the capture probe can be used for attachment to an amino group on the surface of an optical sensor. For example, bifunctional groups, including homobifunctional and heterobifunctional linkers commercially available from Pierce Chemical Company, can be used in several embodiments.

In some embodiments, a capture probe can be attached to a surface of an optical sensor via a linker by derivatizing the surface with a functional group, attaching the derivatized surface to one functional end of a linker, and attaching a capture probe to the other end of the linker. Methods of attaching the capture probe to the functionalized surface of an optical sensor or crosslinker include reactions that form linkage such as thioether bonds, disulfide bonds, amide bonds, carbamate bonds, urea linkages, ester bonds, carbonate bonds, ether bonds, hydrazone linkages, Schiff-base linkages, and non-covalent linkages such as ionic or hydrophobic interactions. It will be appreciated that such reactions will depend on the type of reactive functional groups on the optical sensor, or linker, and capture probe.

In some embodiments, a surface of an optical sensor can be coated with a thin layer of glass, such as silica (SiOx where x=1-2), using a linking agent such as a substituted silane, e.g., 3-mercaptopropyl-trimethoxy silane to link the optical sensor to the glass. The glass-coated optical sensor may then be further treated with a linker, e.g., an amine such as 3-aminopropyl-trimethoxysilane, which will function to link the glass-coated optical sensor to the capture probe. Examples of suitable linkers in various embodiments include N-(3-aminopropyl)-3-mercapto-benzamide, 3-aminopropyl-trimethoxysilane, 3-mercaptopropyl-trimethoxysilane, 3-maleimidopropyl-trimethoxysilane, and 3-hydrazidopropyl-trimethoxysilane.

In some embodiments, the capture probe to attach to a surface of an optical sensor is a nucleic acid capture probe. Any known chemically reactive functional group for nucleic acid attachment to a surface can be used including, but not limited to, aldehyde, epoxy, hydrazide, vinyl sulfone, succinimidyl ester, carbodiimide, maleimide, dithio, iodoacetyl, isocyanate, isothiocyanate, aziridine.

In certain embodiments, a nucleic acid capture probe can be attached to a surface of an optical sensor with the S-4FB crosslinker commercially available from Solulink. The S-4FB linker reacts with primary amines on biomolecules and converts them to 4-formylbenzamide (4FB) linker molecules. 4FB-modified molecules form stable hydrazone bonds when reacted with a (3-N-((6-(N'-Isopropylidene-hydrazino)-nicotinamide)propyltriethyoxysilane) (HyNicSilane, Solulink) modified optical sensor surface.

Density of Capture Probes on an Optical Sensor Surface

In several embodiments, a surface of an optical sensor can have a plurality of the same or different capture probes attached thereto. The dynamic range of analyte detection can be tuned over several orders of magnitude by varying the surface density of the capture probes on the surface. In such embodiments, the plurality of capture probes can increase scalability and allow for multiplex analyte detection. In some aspects, a plurality of the same capture probe provides an ability to detect multiple copies of a given analyte of interest. In other aspects, a plurality of different capture probes are attached to a surface of an optical sensor, thereby permitting multiplex detection of several different analytes of interest. In some embodiments for detecting miRNA analytes of interest, an optical sensor can be functionalized with capture probes for multiple miRNAs. A sample containing the miRNAs of interest can be introduced to such an optical sensor and all of the miRNAs can be detected in parallel.

Capture probe density on a surface of an optical sensor can be controlled, for example, by adjusting the extent of surface derivatization with a chemically reactive functional moiety. For example, capture probe density can be controlled by varying the stoichiometries of a surface reactive functional group, such as siloxane, in the presence of an inert species. It has been demonstrated that the density of binding sites on a silicon dioxide surface can be controlled down to <10-7 of a monolayer. Wayment, J. R.; Harris, J. M. Controlling Binding Site Densities on Glass Surfaces. Anal. Chem. 2006, 78, 7841-7849.

In several embodiments, the capture probes can be attached to a surface of an optical sensor at a density of greater than about 0.001 per square micrometer, greater than about 0.01 per square micrometer, greater than about 0.1 per square micrometer, greater than about 1 per square micrometer, greater than about 10 per square micrometer, greater than about 100 per square micrometer, greater than about 1000 per square micrometer, greater than about 10,000 per square micrometer, greater than about 100,000 per square micrometer, greater than about 1,000,000 per square micrometer, greater than about 10,000,000 per square micrometer, greater than about 100,000,000 per square micrometer, greater than 1,000,000,000 per square micrometer, greater than 10,000,000,000 per square micrometer, greater than 100,000,000,000 per square micrometer, greater than 1,000,000,000,000 per square micrometer or any number in between any of the aforementioned densities. In several embodiments, a surface of an optical sensor can have a range of capture probes spanning from a single capture probe to a number of capture probes that fully saturates all the available binding sites on the surface.

Antibodies

Similar to a sandwich assay format in which an antigen is first bound by a substrate-immobilized primary capture agent and then recognized by a secondary capture agent, the systems of several embodiments provided herein comprise a capture probe (analogous to a sandwich assay primary capture agent) and an antibody (analogous to a sandwich assay secondary capture agent). It is possible to detect and/or measure binding-induced shifts in the resonance wavelength of individual binding events with the systems of various embodiments, including binding of an antibody to the optical sensor. Without being bound by theory, binding of an antibody to the optical sensor can induce a change in local refractive index, thereby inducing a detectable and/or measurable shift in the resonance wavelength on the optical sensor.

In several embodiments, a system for detecting and/or measuring an analyte of interest includes an antibody capable of binding to the analyte of interest or a complex or duplex formed between a capture probe attached to a surface of an optical sensor and the analyte of interest. It will be understood that in several embodiments the antibody capable of binding to a complex or duplex formed between a capture probe and analyte of interest can bind to a portion of the analyte of interest that is not bound to the capture probe in formation of the complex or duplex such that the antibody does not directly bind and/or physically contact the capture probe. Thus, the binding of a capture probe/analyte complex by the antibody can be accomplished by the antibody contacting and binding only the analyte portion of the capture probe/analyte complex. In various aspects, an antibody can bind to an epitope on an analyte of interest distinct from the epitope or binding site on the analyte of interest involved in binding to the capture probe. In some aspects, the antibody capable of binding to a complex or duplex formed between a capture probe and analyte of interest binds to the analyte of interest without inhibiting or interfering with the binding between the analyte of interest and the capture probe.

An example of a binding event that increases the refractive index at the optical sensor surface and can be observed as an increase in the resonance wavelength of the optical sensor is an antibody-analyte complex binding to a capture probe attached to a surface of an optical sensor (a "primary" binding event). Yet another detectable and/or measurable binding event is an antibody binding to an analyte of interest which is already bound to a capture probe attached to a surface of an optical sensor (a "secondary" binding event). A further detectable and/or measurable binding event is an antibody binding to a duplex or complex formed between an analyte of interest and a capture probe attached to a surface of an optical sensor (a "secondary" binding event).

It will be understood by a person of ordinary skill in the art that in several aspects, an antibody can bind to the analyte of interest either prior to or after binding between the analyte of interest and capture probe. Thus, in some embodiments a binding-induced shift in the resonance wavelength can be detected and/or measured for (1) an antibody-analyte complex binding to a capture probe attached to a surface on an optical sensor, (2) an antibody binding to the analyte already bound to the capture probe attached to a surface on an optical sensor, or (3) an antibody binding to the duplex or complex formed between the analyte and capture probe attached to a surface on an optical sensor. It will also be apparent to a person of ordinary skill in the art that in some aspects, an antibody is not capable of binding to the capture probe alone or analyte of interest alone, but is capable of binding to the complex or duplex formed between the capture probe and analyte of interest.

Accordingly, certain embodiments drawn to a system for detecting an analyte of interest includes both (1) a capture probe comprising an antibody attached to a surface of an optical sensor and (2) an antibody capable of binding to the analyte of interest either prior to or after binding between the analyte of interest and capture probe. In additional embodiments, a system for detecting an analyte of interest includes (1) a capture probe comprising a nucleic acid attached to a surface of an optical sensor wherein the capture probe is capable of binding to an analyte of interest, and (2) an antibody that is not capable of binding to the capture probe alone or analyte of interest alone, but is capable of binding to the complex or duplex formed between the capture probe and analyte of interest.

In certain embodiments, the system includes an antibody that specifically binds to an oligonucleotide duplex, such as a DNA:RNA duplex, DNA:DNA duplex, or RNA:RNA duplex, formed between a capture probe and analyte of interest, but does not bind to the nucleic acid capture probe or analyte of interest prior to their binding. As used herein, the term "duplex" refers to a double-stranded molecule, which can be formed by hybridization of single-stranded nucleic acids.

Anti-DNA:RNA antibodies can detect miRNA analytes of interest while significantly reducing assay complexity. Both monoclonal and polyclonal antibodies against RNA:RNA and DNA:RNA homoduplexes have been previously developed and utilized in hybridization based assays for the detection of numerous nucleic acid targets such as viral nucleic acids and E. coli small RNA. Casebolt, D. B. and C. B. Stephensen, Journal of Clinical Microbiology, 1992. 30(3): p. 608-12; Fliss, I., et al., Appl Microbiol Biotechnol, 1995. 43(4): p. 717-24; Lafer, E. M., et al., J Biol Chem, 1986. 261(14): p. 6438-43; Riley, R. L., D. J. Addis, and R. P. Taylor, J Immunol, 1980. 124(1): p. 1-7; Stollar, B. D., FASEB J, 1994. 8(3): p. 337-42 and Stollar, B. D. and A. Rashtchian, Anal Biochem, 1987. 161(2): p. 387-94; which are all incorporated by reference in their entireties.

In particular embodiments, a system for detecting an analyte of interest includes an antibody that specifically binds to a DNA:RNA duplex. One non-limiting example of such an antibody that can be used in several embodiments is that specifically binds to a DNA:RNA duplex is S9.6, a monoclonal antibody that specifically binds to RNA-DNA hybrids as described in Boguslawski et al., J. Immunological Methods, 89 (1986) 123-130, which is herein incorporated by reference in its entirety.

In several embodiments, the monoclonal antibody S9.6 is used to detect a miRNA analyte of interest. S9.6 is obtained from the hybridoma mouse cell line HB-8730, which exhibits sequence independent high binding affinity and specificity to RNA:DNA heteroduplexes. Hu, Z., et al., Nucl. Acids Res., 2006. 34(7): e.52; Székvölgyi, L., et al., Proceedings of the National Academy of Sciences, 2007. 104(38): p. 14964-14969; and Kinney, J. S., et al., Journal of Clinical Microbiology, 1989. 27(1): p. 6-12 and Boguslawski, S. J., et al., Journal of Immunological Methods, 1986. 89(1): p. 123-130, which are all incorporated by reference in their entireties. The HB-8730 mouse hybridoma cell line can be obtained from the American Type Culture Collection (ATCC).

Particles

While systems comprising an antibody configured in a sandwich assay format can detect and/or measure "primary" or "secondary" binding events, several embodiments are drawn to systems comprising a particle adapted to amplify a detectable and/or measurable optical property that is altered (e.g. resonance wavelength) upon a binding event on an optical sensor. Such embodiments are based on the present discovery that a "secondary" or "tertiary" binding event of particles to an optical sensor can increase the sensitivity of detection (i.e. lower the detection limit) by several-fold. For example, a particle can increase the sensitivity of detection from approximately the low pM to the high fM range, compared to a "secondary" binding event. In certain embodiments, systems can comprise a particle adapted to provide a "primary" binding event detectable signal. For example, a particle can be bound to an analyte of interest and a complex formed between them can then be bound to a capture probe attached to a surface of an optical sensor.

Several embodiments relate to a system for detecting an analyte of interest including a particle attached to an antibody, which is capable of specifically binding to the analyte or a duplex or complex formed between the analyte and capture probe, or capable of binding to the antibody. The particle is adapted to amplify a detectable and/or measurable optical property that is altered upon a binding event on an optical sensor. In one aspect, a particle can bind to an antibody that is already bound to an optical sensor, whether via binding to an analyte which is bound to a capture probe attached to a surface of the optical sensor or binding to a duplex or complex formed between the analyte of interest and a capture probe. Such a binding of the particle in this fashion can be considered a "tertiary" binding event, while the prior binding of the antibody to the optical sensor is a "secondary" binding event and the binding of the analyte of interest to the capture probe is a "primary" binding event.

In various embodiments, a particle can associated with a molecule (e.g. by conjugation) that has affinity for the analyte of interest. For example, and not by limitation, a particle can be associated with a silane molecule having affinity to a polypeptide analyte of interest; a particle can be associated with a phosphate-containing molecule having affinity to a nucleic acid analyte of interest; a particle can be associated with a salt having affinity to a carbohydrate analyte of interest; or a particle can be associated with a organic molecule having affinity to a lipid.

It will be understood that in several aspects, a particle can be associated with a molecule that has affinity for the analyte of interest in the same way that capture probes described above can bind to an analyte of interest. For example, the analyte of interest and molecule associated with a particle can represent a binding pair, which can include but is not limited to antibody/antigen (nucleic acid or polypeptide), receptor/ligand, polypeptide/nucleic acid, nucleic acid/ nucleic acid, enzyme/substrate, carbohydrate/lectin, or polypeptide/polypeptide. It will also be understood that binding pairs of analytes of interest and molecules associated with particles described above can be reversed in several embodiments. Any of the functional groups and linkers described above with respect to attaching capture probes to an optical sensor surface can be used to conjugate particles to molecules that have affinity to an analyte of interest. In certain embodiments, an antibody can be conjugated to a particle, such as a COOH-functionalized polystyrene bead, via a n-hydroxysuccinimide ester (NHS) linkage, a DNA molecule can be conjugated to a particle, such as a streptavidin coated glass microsphere via biotin-streptavidin binding, a carbohydrate molecule can be conjugated to a particle, such as a gold nanoparticle, via a thiol linkage, a polypeptide molecule can be conjugated to a particle, such as a titanium dioxide nanoparticle, via an isocyanate silane linkage, and a polypeptide molecule can be conjugated to a particle, such as a magnetic nanoparticle or microsphere, via 1-ethyl-3-(3-dimethylaminopropyl)carbodiimide (EDC). It will also be understood that in various embodiments a molecule that has affinity for the analyte of interest can be associated with a particle by passive absorption.

It will be appreciated that a particle can comprise any material, shape, physical state, and/or size sufficient to amplify a detectable and/or measurable optical property that is altered upon a binding event on an optical sensor. Without being bound by theory, in some embodiments a particle comprises any material, shape, physical state, and/or size sufficient to increase the refractive index at the sensor surface, which can be observed as an increase in the resonance wavelength of the optical sensor. Any particle that has sufficient mass or other physical property, such as electron density, to increase the refractive index at the sensor surface can be used. In some embodiments, a particle can be amorphous or spherical, cubic, star-shaped, and the like. The particles provided herein can comprise solids, liquids, or gasses. In several embodiments, a particle can comprise crystalline, polycrystalline, polymer, glass, biopolymer, or a composite of these materials.

In some embodiments, a particle adapted to amplify a detectable and/or measurable optical property that is altered upon a binding event on an optical sensor has a dimension along any axis, such as an average diameter, of at least about 0.1 nanometers (nm), 0.5 nm, 1 nm, 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 600 nm, 700 nm, 800 nm, 900 nm, 1,000 nm, 2,000 nm, 3,000 nm, 4,000 nm, 5,000 nm, greater than 5,000 nm, any number in between the aforementioned dimensions, or any range between two of the aforementioned dimensions. In several embodiments, a particle has a dimension along any axis, such as an average diameter, of about 1 nm to 1,000 nm. In several embodiments, a particle has a dimension along any axis, such as an average diameter, of about 50 nm to 200 nm.

In some embodiments, a particle comprises a polypeptide of at least 200 Daltons, (Da), 300 Da, 400 Da, 500 Da, 600 Da, 700 Da, 800 Da, 900 Da, 1 kilo Dalton (kDa), 5 kDa, 10 kDa, 15 kDa, 20 kDa, 25 kDa, 50 kDa, 75 kDa, 100 kDa, 200 kDa, 300 kDa, 400 kDa, 500 kDa, 600 kDa, 700 kDa, 800 kDa, 900 kDa, 1,000 kDa, 2,000 kDa, 3,000 kDa, 4,000 kDa, 5,000 kDa, 6,000 kDa, 7,000 kDa, 8,000 kDa, 9,000 kDa, 10,000 kDa, greater than 10,000 kDa, or any size or range between any two of the aforementioned sizes.

In some embodiments, a particle comprises any known polypeptide commonly used in molecular biology as recombinant expression or purification tags including, but not limited to histidine (His), maltose binding protein (MBP), FLAG, Trx, myc, streptavidin, biotin, human influenza virus hemagluttinin (HA), vesicular stomatitis virus glycoprotein (VSV-G), glycoprotein-D precursor of Herpes simplex virus (HSV), V5, AU1, glutathione-S-transferase (GST), the calmodulin binding domain of the calmodulin binding protein, Protein A, and Protein G. Non-limiting examples of specific protocols for selecting, making and using an appropriate tag are described in, e.g., Epitope Tagging, pp. 17.90-17.93 (Sambrook and Russell, eds., Molecular Cloning A Laboratory Manual, Vol. 3, 3rd ed. 2001), which is herein incorporated by reference in its entirety.

In several embodiments, a particle comprises a nanoparticle, nanosphere, microcapsule, nanocapsule, microsphere, microparticle, bead, colloid, aggregate, flocculate, insoluble salt, emulsion, crystal, detergent, surfactant, dendrimer, copolymer, block polymer, nucleic acid, carbohydrate, lipid, liposome, or insoluble complex. It is contemplated that these types of particles can have any size in the picometer, nanometer, micrometer, or millimeter range along any dimensional axis. As used herein, the term "nanoparticle" refers to any particle having a greatest dimension (e.g., diameter) that is less than about 2500 nm. In some embodiments, the nanoparticle is a solid or a semi-solid. In some embodiments, the nanoparticle is generally centrosymmetric. In some embodiments, the nanoparticle contains a generally uniform dispersion of solid components.

Nanoparticles can have a characteristic dimension of less than about 1 micrometer, where the characteristic dimension of a particle is the diameter of a perfect sphere having the same volume as the particle. For example, the nanoparticle may have a characteristic dimension that is less than 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm, or 20 nm, or any number in between the aforementioned sizes. In some embodiments, the nanoparticle can have a characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm, or any number in between the aforementioned sizes. In other embodiments, the nanoparticle can have a characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

In various embodiments, a particle comprises one or more materials including, but not limited to, polymers such as polystyrene, silicone rubber, latex, polycarbonate, polyurethanes, polypropylenes, polymethylmethacrylate, polyvinyl chloride, polyesters, polyethers, and polyethylene. Additional examples of suitable polymers include, but are not limited to the following: polyethylene glycol (PEG); poly(lactic acid-co-glycolic acid) (PLGA); copolymers of PLGA and PEG; copolymers of poly(lactide-co-glycolide) and PEG; polyglycolic acid (PGA); copolymers of PGA and PEG; poly-L-lactic acid (PLLA); copolymers of PLLA and PEG; poly-D-lactic acid (PDLA); copolymers of PDLA and PEG; poly-D,L-lactic acid (PDLLA); copolymers of PDLLA and PEG; poly(ortho ester); copolymers of poly(ortho ester) and PEG; poly(caprolactone); copolymers of poly(caprolactone) and PEG; polylysine; copolymers of polylysine and PEG; polyethylene imine; copolymers of polyethylene imine and PEG; polyhydroxyacids; polyanhydrides; polyhydroxyalkanoates, poly(L-lactide-co-L-lysine); poly(serine ester); poly(4-hydroxy-L-proline ester); poly-α-(4-aminobutyl)-L-glycolic acid; derivatives thereof; combinations thereof; and copolymers thereof.

Further examples of polymeric and non-polymeric materials that can be used in particles of several embodiments include, but are not limited to, poly(lactide), poly(hydroxybutyrate), poly(beta-amino) esters and/or copolymers thereof. Alternatively, the particles can comprise other materials, including but not limited to, poly(dienes) such as poly(butadiene) and the like; poly(alkenes) such as polyethylene, polypropylene and the like; poly(acrylics) such as poly(acrylic acid) and the like; poly(methacrylics) such as poly(methyl methacrylate), poly(hydroxyethyl methacrylate), and the like; poly(vinyl ethers); poly(vinyl alcohols); poly(vinyl ketones); poly(vinyl halides) such as poly(vinyl chloride) and the like; poly(vinyl nitriles), poly(vinyl esters) such as poly(vinyl acetate) and the like; poly(vinyl pyridines) such as poly(2-vinyl pyridine), poly(5-methyl-2-vinyl pyridine) and the like; poly(styrenes); poly(carbonates); poly(esters); poly(orthoesters); poly(esteramides); poly(anhydrides); poly(urethanes); poly(amides); cellulose ethers such as methyl cellulose, hydroxyethyl cellulose, hydroxypropyl methyl cellulose and the like; cellulose esters such as cellulose acetate, cellulose acetate phthalate, cellulose acetate butyrate; and polysaccharides. These materials may be used alone, as physical mixtures (blends), or as copolymers.

In several embodiments, a particle comprises a semiconductor nanocrystal. A semiconductor nanocrystal is a nanocrystal of Group II-VI and/or Group III-V semiconductor compounds. Examples of semiconductor nanocyrstals include, but are not limited to Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof.

In several embodiments, a particle comprises a metal particle, such as an Au, Ag, Pd, Pt, Cu, Ni, Co, Fe (e.g. iron sulfide), Mn, Ru, Rh, Os, or Ir particle. In various embodiments, a particle comprises a metal oxide particle. Examples of suitable metal oxide particles include zinc oxide, titanium (di)oxide, iron oxide, silver oxide, copper oxide, aluminum oxide, or silicon (di)oxide particles. In certain embodiments, a particle comprises a magnetic particle, such as a magnetic bead, nanoparticle, microparticle, and the like.

In several embodiments, a particle comprises a liposome. Liposomes are unilamellar or multilamellar vesicles which have a membrane formed from a lipophilic material and an aqueous interior. The aqueous interior portion contains the composition to be delivered. Phospholipids used for liposome formation include, but are not limited to, natural phospholipids such as egg yolk lecithin (phosphatidyl choline), soybean lecithin, lysolecithin, sphingomyelin, phosphatidic acid, phosphatidyl serine, phosphatidyl glycerol, phosphatidyl inositol, phosphatidyl ethanolamine, diphosphatidyl glycerol. Liposome preparation is described, for example, in U.S. Pat. Nos. 7,208,174, 7,108,863, 5,192,549, 6,958,241, and in Ann. Rev. Biophys. Bioeng., 9, 467 (1980), "Liposomes" (Ed. by M. J. Ostro, Marcel Dekker, Inc.) the entire contents of which are incorporated herein by reference.

When phospholipids and many other amphipathic lipids are dispersed gently in an aqueous medium they swell, hydrate and spontaneously form multilamellar concentric bilayer vesicles with layers of aqueous media separating the lipid bilayers. These systems commonly are referred to as multilamellar liposomes or multilamellar vesicles (MLV) and usually have diameters of from 0.2 µm to 5 µm. Sonication of MLV results in the formation of small unilamellar vesicles (SUV) with diameters usually in the range of 20 to 100 nm, containing an aqueous solution in the core. Multivesicular liposomes (MVL) differ from multilamellar liposomes in the random, non-concentric arrangement of chambers within the liposome. Amphipathic lipids can form a variety of structures other than liposomes when dispersed in water, depending on the molar ratio of lipid to water, but at low ratios the liposome is the preferred structure.

The physical characteristics of liposomes generally depend on pH and ionic strength. They characteristically show low permeability to ionic and polar substances, but at certain temperatures can undergo a gel-liquid crystalline phase (or main phase) transition dependent upon the physical properties of the lipids used in their manufacture which markedly alters their permeability. The phase transition involves a change from a closely packed, ordered structure, known as the gel state, to a loosely packed, less-ordered structure, known as the liquid crystalline state.

Various types of lipids differing in chain length, saturation, and head group have been used in liposomal formulations for years, including the unilamellar, multilamellar, and multivesicular liposomes mentioned above.

There are at least three types of liposomes. The term "multivesicular liposomes (MVL)" generally refers to man-made, microscopic lipid vesicles comprising lipid membranes enclosing multiple non-concentric aqueous chambers. In contrast, "multilamellar liposomes or vesicles (MLV)" have multiple "onion-skin" concentric membranes, in between which are shell-like concentric aqueous compartments. Multilamellar liposomes and multivesicular liposomes characteristically have mean diameters in the micrometer range, usually from 0.5 to 25 µm. The term "unilamellar liposomes or vesicles (ULV)" generally refers to liposomal structures having a single aqueous chamber, usually with a mean diameter range from about 20 to 500 nm.

Multilamellar and unilamellar liposomes can be made by several relatively simple methods. A number of techniques for producing ULV and MLV are described in the art (for example in U.S. Pat. No. 4,522,803 to Lenk; U.S. Pat. No. 4,310,506 to Baldeschweiler; U.S. Pat. No. 4,235,871 to Papahadjopoulos; U.S. Pat. No. 4,224,179 to Schneider, U.S. Pat. No. 4,078,052 to Papahadjopoulos; U.S. Pat. No. 4,394,372 to Taylor U.S. Pat. No. 4,308,166 to Marchetti; U.S. Pat. No. 4,485,054 to Mezei; and U.S. Pat. No. 4,508,703 to Redziniak).

By contrast, production of multivesicular liposomes generally requires several process steps. Briefly, a common method for making MVL is as follows: The first step is making a "water-in-oil" emulsion by dissolving at least one amphipathic lipid and at least one neutral lipid in one or more volatile organic solvents for the lipid component, adding to the lipid component an immiscible first aqueous component and a biologically active substance to be encapsulated, and optionally adding, to either or both the lipid component and the first aqueous component, an acid or other excipient for modulating the release rate of the encapsulated biologically active substances from the MVL. The mixture is emulsified, and then mixed with a second-immiscible aqueous component to form a second emulsion. The second emulsion is mixed either mechanically, by ultrasonic energy, nozzle atomization, and the like, or by combinations thereof, to form solvent spherules suspended in the second aqueous component. The solvent spherules contain multiple aqueous droplets with the substance to be encapsulated dissolved in them (see Kim et al., Biochem. Biophys. Acta, 728:339-348, 1983). For a comprehensive review of various methods of ULV and MLV preparation, refer to Szoka, et al. Ann. Rev. Biophys. Bioeng. 9:465-508, 1980.

Making multivesicular liposomes can involve inclusion of at least one amphipathic lipid and one neutral lipid in the lipid component. The amphipathic lipids can be zwitterionic, anionic, or cationic lipids. Examples of zwitterionic amphipathic lipids are phosphatidylcholines, phosphatidylethanolamines, sphingomyelins etc. Examples of anionic amphipathic lipids are phosphatidylglycerols, phosphatidylserines, phosphatidylinositols, phosphatidic acids, etc. Examples of cationic amphipathic lipids are diacyl trimethylammonium-propane and ethyl phosphatidylcholine. Examples of neutral lipids include diglycerides, such as diolein, dipalmitolein, and mixed caprylin-caprin diglycerides; triglycerides, such as triolein, tripalmitolein, trilinolein, tricaprylin, and trilaurin; vegetable oils, such as soybean oil; animal fats, such as lard and beef fat; squalene; tocopherol; and combinations thereof. Additionally, cholesterol or plant sterols can be used in making multivesicular liposomes.

The liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

In various embodiments, liposomes can be composed of phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions can be formed from dimyristoyl phosphatidylglycerol, while anionic fusogenic liposomes can be formed from dioleoyl phosphatidylethanolamine (DOPE). Another type of liposomal composition can be formed from phosphatidylcholine (PC) such as, for example, soybean PC, and egg PC. Another type can be formed from mixtures of phospholipid and/or phosphatidylcholine and/or cholesterol.

Examples of phospholipids suitable for use in several embodiments include but are not limited to DOPC or DC18:1 PC=1,2-dioleoyl-sn-glycero-3-phosphocholine; DLPC or DC12:0 PC=1,2-dilauroyl-sn-glycero-3-phosphocholine; DMPC or DC14:0 PC=1,2-dimyristoyl-sn-glycero-3-phosphocholine; DPPC or DC16:0PC=1,2-dipalmitoyl-sn-glycero-3-phosphocholine; DSPC or DC18:0PC=1,2-distearoyl-sn-glycero-3-phosphocholine; DAPC or DC20:0PC=1,2-diarachidoyl-sn-glycero-3-phosphocholine; DBPC or DC22:0 PC=1,2-dibehenoyl-sn-glycero-3-phosphocholine; DC16:1PC=1,2-dipalmitoleoyl-sn-glycero-3-phosphocholine; DC20:1PC=1,2-dieicosenoyl-sn-glycero-3-phosphocholine DC22:1PC=1,2-dierucoyl-sn-glycero-3-phosphocholine; DPPG=1,2-dipalmitoyl-sn-glycero-3-phosphoglycerol; DOPG=1,2-dioleoyl-sn-glycero-3-phosphoglycerol.

Furthermore, liposomes of various embodiments can be of various sizes. For example, the average diameter of a liposome in various embodiments can be about 300 nm, about 295 nm, about 290 nm, about 285 nm, about 280 nm, about 275 nm, about 270 nm, about 265 nm, about 260 nm, about 255 nm, about 250 nm, about 245 nm, about 240 nm, about 235 nm, about 230 nm, about 225 nm, about 220 nm, about 215 nm, about 210 nm, about 205 nm, about 200 nm, about 195 nm, about 190 nm, about 185 nm, about 180 nm, about 175 nm, about 170 nm, about 165 nm, about 160 nm, about 155 nm, about 150 nm, about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 15 nm, about 10 nm, or about 5 nm. In certain embodiments, a liposome has a diameter of about 50 nm to 200 nm.

In several embodiments, a particle comprises a surfactant. Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the 'head') provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. Popular members of the anionic surfactant class are the alkyl sulfates and the soaps. Also contemplated as examples of anionic surfactants that can be used in several embodiments include stearic acid and sodium behenoyl actylate.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides. The use of surfactants in drug products, formulations and in emulsions has been reviewed (Rieger, in "Pharmaceutical Dosage Forms," Marcel Dekker, Inc., New York, N.Y., 1988, p. 285). Preferably such surfactants are nonionic and may be in the form of silicones or organic nonionic surfactants.

Suitable silicone surfactants include but are not limited to polyorganosiloxane polymers that have amphiphilic properties, for example contain hydrophilic radicals and lipophilic radicals. These silicone surfactants may be liquids or solids at room temperature. Examples of silicone surfactants that can be used in various embodiments include, but are not limited to: dimethicone copolyols, alkyl dimethicone copolyols, and emulsifying silicone elastomers. Emulsifying silicone elastomers are elastomers that have one or more hydrophilic groups such as hydroxyl, oxyethylene, and the like bonded thereto so as to confer hydrophilic properties to the elastomer. Suitable organic nonionic surfactants may include alkoxylated alcohols or ethers formed by the reaction of an alcohol with a polyalkyleneoxide containing repeating units of alkylene oxide. Preferably, the alcohol is a fatty alcohol having 6 to 30 carbon atoms. Examples of organic nonionic surfactants that can be used in various embodiments include, but are not limited to: steareth 2-100, beheneth 5-30, ceteareth 2-100, ceteareth-25, ceteth 1-45, and the like, which are formed by polyethyleneoxide with the corresponding stearyl/behenyl/cetyl alcohol (wherein the number as used herein designates the number of repeating units of ethylene oxide in the polyethyleneoxide). Other alkoxylated alcohols include esters formed by reaction of polymeric alkylene glycols with glyceryl fatty acid, such as PEG glyceryl oleates, PEG glyceryl stearate; or PEG polyhydroxyalkanotes such as PEG dipolyhydroxystearate wherein the number of repeating ethylene glycol units ranges from 3 to 1000. Nonionic surfactants formed by the reaction of a carboxylic acid with an alkylene oxide or with a polymeric ether are also suitable examples. Monomeric, homopolymeric, or block copolymeric ethers, alkoxylated sorbitan, alkoxylated sorbitan derivatives can also be used as nonionic surfactants in various embodiments.

Figure 30A:
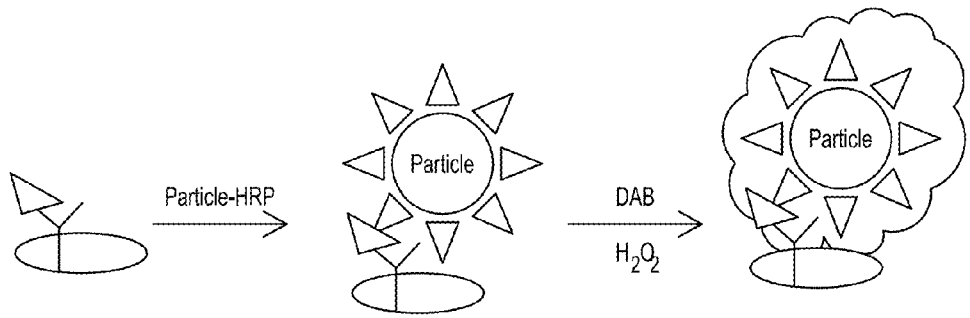
FIG. 30A is a schematic showing a process of binding a particle attached to horse radish peroxidase (HRP) to an analyte of interest, which is already bound to an antibody capture probe, and precipitating the substrate 3,3'-diaminodibenzidine (DAB) onto the microring.

In several embodiments, a particle can be associated with a molecule that has catalytic activity. Addition of a substrate of the molecule having catalytic activity can further amplify a detectable and/or measurable optical property that is altered (e.g. resonance wavelength) upon a binding event on an optical sensor. For example, a particle can be conjugated to horse radish peroxidase (HRP), which can be used to precipitate a substrate, such as 3,3'-diaminodibenzidine (DAB) onto the optical sensor, further amplifying a detectable signal (see e.g. FIG. 30A).

The particles of various embodiments can comprise a core having any of the materials described above or composites thereof, and a surrounding coat having any of the materials described above or composites thereof. For example, a particle can comprise a magnetic core and a clear coat and/or a coat having a high index dielectric, such as polystyrene. In certain embodiments, a particle can comprise a core having any of the materials described above or composites thereof and a coat surrounding the core having a metal oxide material, such as titanium dioxide, and/or magnetic material.

Methods of Detecting and/or Measuring the Concentration of Analytes

Several embodiments are drawn to detecting and/or measuring the concentration of an analyte of interest in a sample using the systems described above, which can provide for real-time multiplex detection and measurement of low abundance biomolecules with high sensitivity and specificity. It is possible to detect and/or measure binding-induced shifts in the resonance wavelength of individual binding events in real-time with the systems of several embodiments. In several embodiments, "primary," "secondary," and "tertiary" binding events can be applied to an optical sensor and detected and/or measured using various molecule-to-molecule binding assays. In various embodiments, binding events can be detected in real time and/or in multiplex format. In several embodiments, analytes of interest can be detected and/or measured at least at the femtomolar (fM) ($1\times10^{-15}$ M) sensitivity range. In various embodiments, an analyte of interest can be present in the sample at least in the femtomolar concentration range or in the picogram per milliliter (pg/mL) range and detected or measured using the systems described above.

Figure 30B:
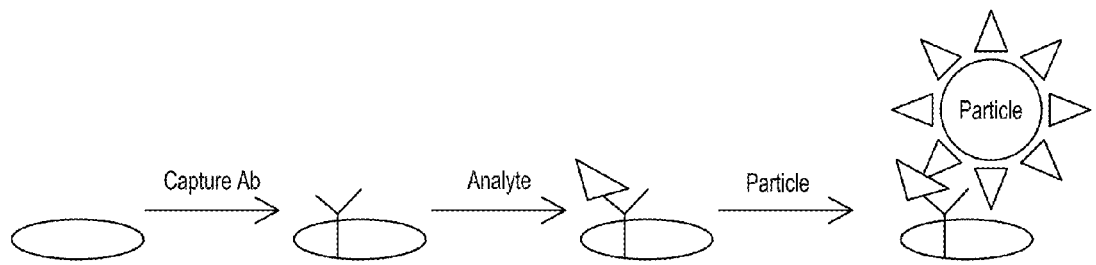
FIG. 30B is a schematic showing a process of attaching an antibody capture probe to a microring, binding an analyte to the antibody capture probe, and binding a particle to the analyte.
Figure 30C:
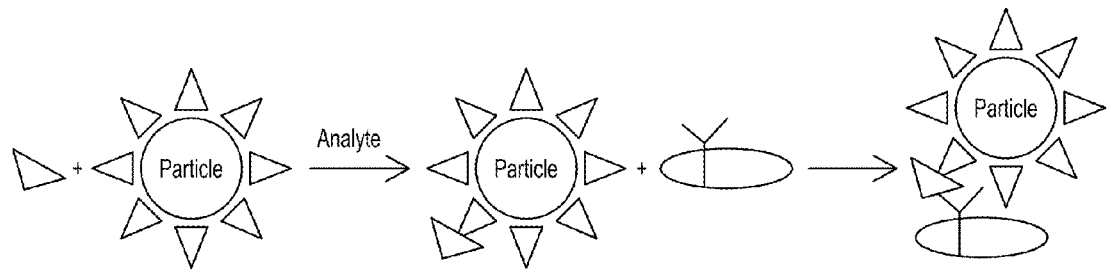
FIG. 30C is a schematic showing a process of pre-mixing an analyte with a particle to form a complex and binding the complex to an antibody capture probe attached to a microring.
Figure 30D:
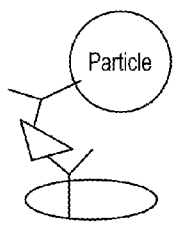
FIG. 30D is a schematic illustrating binding between an antibody attached to a particle and an analyte bound to an antibody capture probe on a microring.

In some embodiments, such binding events detectable in real-time include a "primary" binding event between an analyte of interest (with or without a pre-bound particle) and a capture probe (see e.g. FIGS. 30B and 30C), a "secondary" binding event between an antibody (with or without a pre-bound particle) and the analyte of interest already bound to the capture probe (see e.g. FIG. 30D), a "secondary" binding event between an antibody (with or without a pre-bound particle) and a duplex or complex formed between the analyte and capture probe, a "secondary" binding event between a particle and the analyte of interest already bound to the capture probe (e.g. wherein the capture probe comprises an antigen and the analyte of interest is an antibody against the antigen), or a "tertiary" binding event between a particle and antibody already bound to the optical sensor via a "secondary" binding event. Without being bound by theory, in several embodiments these events induce changes in local refractive index of the optical sensor, thereby inducing a detectable and/or measurable shift in the resonance wavelength on the optical sensor.

Accordingly, several embodiments are drawn to methods of detecting an analyte of interest in a sample comprising providing an optical sensor (e.g. optical ring resonator) comprising a capture probe attached to a surface of the optical sensor (e.g. optical ring resonator), wherein the capture probe is capable of binding to the analyte of interest to form a complex; applying a sample for which the presence or absence of the analyte of interest is to be determined to the optical sensor (e.g. optical ring resonator) under conditions in which the analyte of interest, when present, and the capture probe bind to form a complex; providing an antibody that specifically binds to the complex or analyte, wherein binding between the antibody and the complex or the analyte, when the analyte is bound to the capture probe, alters an optical property of the optical sensor (e.g. optical ring resonator); and determining the presence or absence of the analyte of interest by detecting the altered optical property of the optical sensor (e.g. optical ring resonator). In some aspects, the concentration of the analyte of interest in the sample is measured. Detecting and/or measuring the concentration of an analyte of interest in a sample can be performed in real-time and/or in multiplex with other analytes of interest or samples.

Certain embodiments relate to methods of detecting an antibody of interest, such as an antibody biomarker, including providing an optical sensor (e.g. optical ring resonator) comprising a capture probe attached to a surface of the optical sensor (e.g. optical ring resonator), wherein the capture probe comprises an antigen that is capable of binding to the antibody of interest to form a complex; applying a sample for which the presence or absence of the antibody of interest is to be determined to the optical sensor (e.g. optical ring resonator) under conditions in which the antibody of interest, when present, and the capture probe bind to form a complex; providing a detection antibody that binds to the antibody of interest, wherein binding between the detection antibody and antibody of interest, when the antibody of interest is bound to the capture probe, alters an optical property of the optical sensor (e.g. optical ring resonator); and determining the presence or absence of the antibody of interest by detecting the altered optical property of the optical sensor (e.g. optical ring resonator). For example, the antibody of interest can be a human subject's auto-antibody against an auto-antigen associated with an autoimmune disorder and the detection antibody can be an anti-human IgG, IgA, or IgM antibody. As another example, the antibody of interest can be a human subject's antibody against an antigen associated with an allergy and the detection antibody can be an anti-human IgE antibody. In some aspects, the concentration of the antibody of interest in the sample is measured. Detecting and/or measuring the concentration of an antibody of interest in a sample can be done in real-time and/or in multiplex with other analytes of interest or samples.

Where the analyte of interest is a nucleic acid molecule, several embodiments relate to methods of detecting a nucleic acid molecule of interest in a sample comprising: providing an optical sensor comprising a nucleic acid capture probe attached to a surface of the optical sensor, wherein the capture probe is capable of hybridizing to the nucleic acid molecule of interest to form a duplex; applying a sample for which the presence or absence of the nucleic acid molecule of interest is to be determined to the optical sensor under conditions in which the nucleic acid molecule of interest, when present, and the capture probe sequence-specifically hybridize to form a duplex; providing an antibody that specifically binds a duplex of nucleic acid molecules, wherein binding between the antibody and the duplex of the capture probe and nucleic acid molecule of interest alters an optical property of the optical sensor; and determining the presence or absence of the nucleic acid molecule of interest by detecting the altered optical property of the optical sensor. In some aspects, the concentration of the nucleic acid molecule of interest in the sample is measured. Detecting and/or measuring the concentration of a nucleic acid molecule of interest in a sample can be done in real-time and/or in multiplex with other analytes of interest or samples.

In some aspects, the nucleic acid molecule of interest is microRNA (miRNA). Despite their roles in cellular processes, miRNAs pose a unique set of challenges for their analysis. Short sequence lengths, low abundance, and high sequence similarity all contribute to make miRNA quantitation difficult using traditional nucleic acid quantitation techniques such as Northern blotting, reverse transcriptase polymerase chain reaction (RT-PCR), and microarray based detection. Northern blotting, the field standard for miRNA analysis, is a labor and time intensive process limited by low throughput and large sample volume requirements. Streit, S., et al., Nat Protoc, 2009. 4(1): p. 37-43. In contrast, RT-PCR can utilize small sample volumes, but is not well suited for quantitative miRNA analysis due to short primers, which often reduce the efficiency of the polymerase reaction and introduce signal bias. miRNA analysis is further complicated by the complex nature of miRNA-mRNA regulatory networks, as a single miRNA can regulate multiple mRNA targets, or jointly regulate the same mRNA with other miRNAs.

Accordingly, in some embodiments, a miRNA of interest can be detected by providing an optical sensor comprising a nucleic acid capture probe (e.g. an oligonucleotide comprising DNA and/or LNA) attached to a surface of the optical sensor, wherein the capture probe is capable of hybridizing to the miRNA of interest to form a duplex; applying a sample for which the presence or absence of the miRNA of interest is to be determined to the optical sensor under conditions in which the miRNA of interest, when present, and the capture probe sequence-specifically hybridize to form a duplex; providing an antibody that specifically binds a duplex of nucleic acid molecules (e.g. antibody S9.6), wherein binding between the antibody and the duplex of the capture probe and miRNA of interest alters an optical property of the optical sensor; and determining the presence or absence of the nucleic acid molecule of interest by detecting the altered optical property of the optical sensor. In some aspects, the concentration of the miRNA of interest in the sample is measured. Detecting and/or measuring the concentration of a miRNA of interest in a sample can be done in real-time and/or in multiplex with other analytes of interest or samples.

Amplification of an altered optical property of the optical sensor can be desirable and accomplished by using a particle described above in a detectable "secondary" or "tertiary" binding event as described above. Use of such particles to amplify an optical detection signal can be useful in detecting or measuring a low abundance analyte of interest in a sample. In several embodiments, a particle can be used to detect and/or measure an analyte of interest present in a sample at least at the femtomolar (fM) ($1\times10^{-15}$ M) concentration range or in the picogram per milliliter (pg/mL) range and detected or measured using the systems described above. In various embodiments, a particle can be used to increase the dynamic range of detecting and/or measuring an analyte of interest present in a sample.

Accordingly, several embodiments are directed to methods of detecting an analyte of interest in a sample including: providing an optical sensor comprising a capture probe attached to a surface of the optical sensor, wherein the capture probe is capable of binding to the analyte of interest to form a complex; applying a sample for which the presence or absence of the analyte of interest is to be determined to the optical sensor, under conditions in which the analyte of interest, when present, and the capture probe bind to form a complex; providing an antibody that specifically binds to the complex or analyte, wherein binding between the antibody and the complex or the analyte, when the analyte is bound to the capture probe, alters an optical property of the optical sensor; providing a particle attached to the antibody or a particle capable of binding the antibody, wherein the particle amplifies the optical property that is altered; and determining the presence or absence of the analyte of interest by detecting the altered optical property of the optical sensor. Use of a particle to amplify a detectable binding event can be used in methods to detect any kind of analyte of interest described above, including nucleic acids, polypeptides, and antibodies in a sample. In some aspects, the concentration of the analyte of interest in the sample is measured by methods involving use of a particle to amplify a detectable binding event. Detecting and/or measuring the concentration of an analyte of interest in a sample can be done in real-time and/or in multiplex with other analytes of interest or samples by methods involving use of a particle to amplify a detectable binding event.

In some embodiments, the analyte of interest is an antibody biomarker from a sample obtained from a subject, such as a human patient suspected of having a disease or condition associated with the antibody biomarker. In one aspect, a sample is applied to an optical sensor to allow an antibody biomarker, if present in the sample, to bind to the capture probe attached to a surface on the optical sensor. In such an aspect, the capture probe is an antigen to which the antibody biomarker is capable of binding. Then, either (1) an antibody-specific particle, such as a bead to which Protein A or Protein G is attached (hereinafter referred to as a "Protein A bead" or "Protein G bead"), is provided and can bind to the antibody biomarker bound to the capture probe, (2) a detection antibody (whether or not pre-bound to a particle, including pre-bound to an antibody specific particle such as a Protein A or Protein G bead) is provided and can bind to the antibody biomarker bound to the capture probe, or (3) the detection antibody is provided first and then an antibody-specific particle is provided that can bind to the detection antibody. In any of these aspects, the particle serves to amplify a detectable altered optical property of the optical sensor.

Accordingly, in some embodiments, a particle, such as a Protein A, Protein G, Protein A/G, or Protein L bead, can be provided in a "secondary" binding event to directly bind to the antibody of interest, which already bound in a "primary" binding event to a capture probe. Protein A, G, A/G, and L bind to immunoglobulins. Whereas Protein A, G, and A/G bind to the Fc region of immunoglobulins, Protein L binds through light chain interactions.

In other embodiments, a particle can be pre-bound to the detection antibody (e.g. an anti-human IgG antibody), and then the resulting complex can be provided in a "secondary" binding event to bind to the antibody of interest, which already bound in a "primary" binding event to a capture probe. For example, a Protein A or Protein G bead can be pre-incubated with a sample to allow binding between the particle and the antibody biomarker, if present. Then, the particle-antibody complex can be applied to an optical sensor to allow the complex to bind to the capture probe. This permits detection and measurement of the antibody biomarker to the capture probe in real time.

In further embodiments, a particle, such as a Protein A or Protein G bead, can be provided in a "tertiary" binding event to bind to the detection antibody, which already bound in a "secondary" binding event to the antibody of interest, which previously bound in a "primary" binding event to a capture probe.

In additional embodiments, a particle, such as a Protein A or Protein G bead, can be pre-bound to the antibody of interest, such as a Protein A or Protein G bead, by incubating a sample from a subject with the particle under conditions permitting binding. Then, the antibody of interest bound to particle can be provided in a "primary" binding event with a capture probe.

It will be appreciated that the concentration of the antibody of interest in the sample can be measured in the foregoing methods. Detecting and/or measuring the concentration of an antibody of interest in a sample can be done in real-time and/or in multiplex with other analytes of interest or samples.

In certain embodiments, the analyte of interest is an antibody from a subject, such as a human, suspected of having an autoimmune disorder. An autoimmune disorder may include, but is not limited to, diabetes mellitus, transplantation rejection, multiple sclerosis, premature ovarian failure, scleroderm, Sjogren's disease, lupus (e.g. Systemic Lupus Erythematosis (SLE)), vitiligo, alopecia (baldness), polyglandular failure, Grave's disease, hypothyroidism, polymyositis, pemphigus, Crohn's disease, colitis, autoimmune hepatitis, hypopituitarism, myocarditis, Addison's disease, autoimmune skin diseases, uveitis, pernicious anemia, hypoparathyroidism, and/or rheumatoid arthritis.

Accordingly, an auto-antibody analyte of interest can be detected and/or measured in a sample in various embodiments using capture probes comprising an autoimmune antigen. Examples of autoimmune antigens that can be used as capture probes include, but are not limited to, Jo-1, Smith, SSA, SSB, and Scl-70, RNP, dsDNA, histone/centromere and such capture probes can be used to detect and/or measure auto-antibodies against these antigens in a sample. Table 1 provides further non-limiting examples of autoimmune antigens associated with various autoimmune diseases that can be used as capture probes for detecting and/or measure auto-antibody biomarkers.

TABLE 1

| Autoimmune Disease | Associated Autoantigen(s) |
| --- | --- |
| Multiple Sclerosis | myelin basic protein, proteolipid protein, myelin associated glycoprotein, cyclic nucleotide phosphodiesterase, myelin-associated glycoprotein, myelin-associated oligodendrocytic basic protein, myelin oligodendrocyte glycoprotein, alpha-B-crystalin |
| Guillian Barre Syndrome | peripheral myelin protein I |
| Diabetes Mellitus | tyrosine phosphatase IA2, IA-2β; glutamic acid decarboxylase (65 and 67 kDa forms), carboxypeptidase H, insulin, proinsulin, pre-proinsulin, heat shock proteins, glima 38, islet cell antigen 69 KDa, p52, islet cell glucose transporter GLUT-2 |
| Rheumatoid Arthritis | Immunoglobulin, fibrin, filaggrin, type I, II, III, IV, V, IX, and XI collagens, GP-39, hnRNPs |
| Autoimmune Uveitis | protein (IRBP), rhodopsin, recoverin |
| Primary Biliary Cirrhosis | pyruvate dehydrogenase complexes (2-oxoacid dehydrogenase) |
| Autoimmune Hepatitis | Hepatocyte antigens, cytochrome P450 |
| Pemphigus Vulgaris | Desmoglein-1, -3 |
| Myasthenia Gravis | acetylcholine receptor |
| Autoimmune Gastritis | $H^+/K^+$ ATPase, intrinsic factor |
| Pernicious Anemia | intrinsic factor |
| Polymyositis | histidyl tRNA synthetase, other synthetases, other nuclear antigens |

TABLE 1-continued

| Autoimmune Disease | Associated Autoantigen(s) |
|---|---|
| Autoimmune Thyroiditis | Thyroglobulin, thyroid peroxidase |
| Graves's Disease | Thyroid-stimulating hormone receptor |
| Vitiligo | Tyrosinase, tyrosinase-related protein-2 |
| Systemic Lupus | nuclear antigens: DNA, histones, |
| Celiac Disease | Transglutaminase |

For example, in certain embodiments the antibody biomarker analyte of interest is from a subject, such as a human patient suspected of having an autoimmune disorder. Accordingly, an auto-antibody analyte of interest can be detected and/or measured in a sample in various embodiments using capture probes comprising an autoimmune antigen. Such auto-antibody biomarkers can be pre-bound to a particle, such as a Protein A or Protein G bead, by incubating a sample from a subject with the particle under conditions permitting binding. Then, the auto-antibodies bound to particles can be applied to an optical sensor having capture probes comprising autoimmune antigens. Examples of autoimmune antigens that can be used as capture probes include, but are not limited to, Jo-1, Smith, SSA, SSB, and Scl-70, and those indicated in Table 1, and such capture probes can be used to detect and/or measure auto-antibodies against these antigens in a sample.

In certain aspects, a sample is applied to an optical sensor to allow an antibody biomarker, if present in the sample, to bind to the capture probe attached to a surface on the optical sensor. Then, a particle is provided and can bind to the antibody biomarker bound to the capture probe. In further aspects, a sample is applied to an optical sensor to allow an antibody biomarker, if present in the sample, to bind to the capture probe attached to a surface on the optical sensor. Then, an anti-human secondary antibody is provided and can bind to the antibody biomarker bound to the capture probe. Such anti-human secondary antibody can be pre-bound to a particle, such as a Protein A or Protein G bead. Alternatively, a particle, such as a Protein A or Protein G bead, can be provided after the anti-human secondary antibody has bound to the antibody biomarker, which itself is bound to the capture probe.

In several embodiments, binding events can be observed by deterministic counting methods involving multiple steps. For example, 1° antibody-modified microring resonators can be incubated with the test sample for a defined period. Particle-tagged 2° antibodies can then be added to quickly saturate the bound analyte of interest. In several embodiments, the number of discrete shifts in an altered optical property induced by binding events, such as resonance wavelength, over a defined time period can be detected or measured. Deterministic counting methods can lend themselves to quantitation over a broad dynamic range: the initial slope of antigen binding could be monitored for detection at high concentrations (μm to low-pM), (Washburn, A L; Gunn, L C; Bailey, R C Label-Free Quantitation of a Cancer Biomarker in Complex Media Using Silicon Photonic Microring Resonators. Anal. Chem. 2009, 81, 9499-9506), followed by the use of a 2° antibody for intermediate concentrations (low-nM to mid-pM), (Luchansky, M S; Bailey, R C Silicon Photonic Microring Resonators for Quantitative Cytokine Detection and T-cell Secretion Analysis. Anal. Chem. 2010, 82, 1975-1981), and then a 3° particle could be introduced via a biotin-streptavidin or anti-IgG interaction to extend to down to trace levels (mid-pM to low-fM or lower).

In various embodiments, binding events can be observed by stochastic recording of binding events. For example, particle-tagged 2° antibodies can be introduced directly into the test sample and allowed to associate with the small amount analyte, expedited by high relative antibody concentrations (2° antibody in excess compared to antigen) and 3-D diffusion. After an appropriate time, the shifts in resonance wavelength are recorded. Since the localization of particles at the sensor surface is guided by the interaction between the antigen and capture probe (already on the surface), the shifts in resonance wavelength are expected to be transient with the binding and unbinding events having characteristic average time constants that directly relate back to the interaction kinetics.

Stochastic recording methods offer an advantage in that the temporal signature of binding, as opposed to the magnitude of response, is the quantifiable measure. Accordingly, the signal-to-noise ratio can be increased by simply integrating over a longer time period. Furthermore, given that $\tau_{off}$ is not correlated to concentration, but rather is impacted solely by the dissociation rate constant of the interaction, it may be possible to distinguish between non-specific and specific binding events since non-specific interactions will have shorter residence times than specific binding events. In several embodiments, single biomolecule detection can distinguish between non-specific and specific binding events. In a traditional "bulk" experiment where the ensemble of many binding events is measured, non-specific binding is indistinguishable from specific antigen-capture agent interactions. In a time domain measurement, $\tau_{off}$ is not correlated to concentration, but rather is impacted solely by the dissociation rate constant of the interaction. Non-specific binding events will likely dissociate much faster meaning that individual unbinding events could be grouped into multiple bins by simple Fourier transform analysis. In this way, the contributions of non-specific binding might be simply filtered out as noise. Thus, in several embodiments, trace components can be detected or measured in extraordinarily complex media, such as blood where the dynamic range of protein concentration varies over 12 orders of magnitude.

Multiplex Optical Systems

The systems of several embodiments described herein can be used in multiplex formats and/or in real-time. As used herein, "multiplex" can refer to a plurality of different capture probes on the same surface of an optical sensor, or can refer to multiple optical sensors, wherein each sensor can comprise one or more of the same or different capture probes. In the latter sense, multiple optical sensors can be manipulated together temporally or spatially.

In several embodiments, multiple optical sensors can be manipulated in a multiplex format at the same or different times. For example, multiple optical sensors can be manipulated simultaneously or at different times in a multiplex platform, such as a chip, with respect to providing reagent(s) for any of the primary, secondary, or tertiary binding events described herein. In some aspects, a test sample can be provided to multiple optical sensors in a multiplex platform simultaneously. In further aspects, an antibody that specifically binds to an analyte of interest or a duplex/complex formed between an analyte of interest and a capture probe can be provided to multiple optical sensors in a multiplex platform simultaneously. In additional aspects, a particle described herein can be provided to multiple optical sensors in a multiplex platform simultaneously. In certain aspects, a plurality of the same type of particle, such as a universal particle, can be provided to multiple optical sensors in a multiplex platform simultaneously. Multiple optical sensors can also be manipulated simultaneously in a multiplex platform, such as a chip, with respect to detecting or measuring the analyte of interest in parallel. In various embodiments, several optical sensors can be independently monitored in a multiplex format. For example, a plurality of optical rings, wherein each optical ring has a distinct detectable optical property, can be queried or monitored within the same location, such as in a reaction chamber or site on a chip, by a single waveguide.

In some embodiments, reagent(s) for any of the primary, secondary, or tertiary binding events described herein can be administered at different times to populations of optical sensors in a multiplex platform, such as a chip. In other words, a reagent can be provided to one population of optical sensors at a first time, and the reagent can be provided to another population(s) of optical sensors at different time(s), wherein each population comprises one or more optical sensors. In various embodiments, the analyte of interest can be detected in one population of optical sensors at one time and in another population(s) of optical sensors at different time(s), wherein each population comprises one or more optical sensors.

In various embodiments, multiple optical sensors can be spatially manipulated in a multiplex format. In some aspects, reagent(s) for any of the primary, secondary, or tertiary binding events described herein can be differentially administered to distinct populations of optical sensors in a multiplex platform, such as a chip. In other words, a reagent can be provided to one population but not another population of optical sensors in a multiplex platform, wherein each population comprises one or more optical sensors. In various embodiments, the analyte of interest can be detected or measured in one population but not in another population of optical sensors, wherein each population comprises one or more optical sensors.

The multiplex embodiments described above are particularly advantageous in reducing cross-talk from the individual detection systems in a multiplex platform. For instance, by temporally or spatially manipulating distinct populations of optical sensors in a multiplex platform, the extent of cross-talk from the individual detection systems can be reduced. As used herein, the term "cross-talk" refers to a binding event that provides undesired signal detected or measured at any given optical sensor. Cross-talk includes false positive signals or interfering signals resulting from non-specific interaction or binding of reagents from one detection system and another.

For example, in an immunoassay format in which a detection system comprises an antibody capture probe or secondary antibody that is capable of undesirably cross-reacting with antigens that are not analytes of interest for a given optical sensor, it is possible to reduce cross-talk by temporally or spatially segregating the source of cross-talk.

In several embodiments, cross-talk can be temporally reduced by providing reagent(s) for any of the primary, secondary, or tertiary binding events described herein at different times. For example, multiple test samples can be provided at different times (e.g. staggered or sequentially), such that a cross-reacting antigen present in some test samples but not others cannot result in an undesired signal at a given time. Also, different secondary antibodies can be provided at different times to reduce non-specific binding of a secondary antibody, which is intended for use with one population of optical sensors, to an analyte of interest associated with a different population of optical sensors. In various embodiments, cross-talk can be reduced by detecting or measuring an analyte of interest in different populations of optical sensors at different times.

Alternatively or additionally, cross-talk can be spatially reduced by providing reagent(s) for any of the primary, secondary, or tertiary binding events described herein to distinct populations of optical sensors in a multiplex platform. For instance, samples having cross-reacting antigens or secondary antibodies capable of cross-reacting with an antigen that is not an analyte of interest can be kept separated from distinct populations of optical sensors. In various embodiments, a multiplex platform can include different flowcells or channels for providing reagents to spatially separate populations of optical sensors in order to reduce cross-talk.

The multiplex embodiments described above are particularly suited for real-time analyte detection, especially in embodiments with reduced cross-talk. Such binding events detectable in real-time include, but are not limited to, a "primary" binding event between an analyte of interest (with or without a pre-bound particle) and a capture probe, a "secondary" binding event between an antibody (with or without a pre-bound particle) and the analyte of interest already bound to the capture probe, a "secondary" binding event between an antibody (with or without a pre-bound particle) and a duplex or complex formed between the analyte and capture probe, a "secondary" binding event between a particle and the analyte of interest already bound to the capture probe, and a "tertiary" binding event between a particle and antibody already bound to the optical sensor via a "secondary" binding event.

While various embodiments have been described in some detail for purposes of clarity and understanding, one skilled in the art will appreciate that various changes in form and detail can be made without departing from the true scope of the invention.

EXAMPLES

Having generally described embodiments drawn to systems for detecting an analyte of interest in a sample and methods of using such systems, a further understanding can be obtained by reference to certain specific examples which are provided for purposes of illustration only and are not intended to be limiting.

Example 1—Optical Sensor Detection of miRNA

Fabrication of Silicon Photonic Microring Resonators and Measurement Instrumentation Sensor chips were fabricated as described in Washburn et al., Analytical Chemistry, 2009. 81(22): p. 9499-9506 and Bailey, R. C. et al., Proceedings of SPIE—The International Society for Optical Engineering, 2009, which are herein incorporated by reference in their entireties.

Nucleic Acid Sequences

All synthetic nucleic acids were obtained from Integrated DNA Technologies ("IDT") (Coralville, Iowa). DNA capture probes were HPLC purified prior to use, while synthetic RNA probes were RNase Free HPLC purified. Table 2 shows the sequences of nucleic acid capture probes used in this Example. Sequences of Synthetic Nucleic Acids Bases in underline indicate the substitution of a locked nucleic acid.

TABLE 2

|  | Sequence (5' to 3') |
| --- | --- |
| hsa miR-16 | UAGCAGCACGUAAAUAUUGGCG (SEQ ID NO: 1) |
| hsa miR-21 | UAGCUUAUCAGACUGAUGUUGA (SEQ ID NO: 2) |
| hsa miR-24-1 | UGGCUCAGUUCAGCAGGAACAG (SEQ ID NO: 3) |
| hsa miR-26a | UUCAAGUAAUCCAGGAUAGGCU (SEQ ID NO: 4) |
| DNA Capture Probe for hsa miR-16 | $NH_2-(CH_2)_{12}-$ ATC GTC GTG CATTTATAACCGC (SEQ ID NO: 5) |
| DNA Capture Probe for hsa miR-21 | $NH_2-(CH_2)_{12}-$ ATCGAATAGTCTGACTACAACT (SEQ ID NO: 6) |
| DNA Capture Probe for hsa miR-24-1 | $NH_2-(CH_2)_{12}-$ CTGTTCCTGCTGAACTGAGCCA (SEQ ID NO: 7) |
| DNA Capture Probe for hsa miR-26a | $NH_2-(CH_2)_{12}-$ AAGTTCATTAGGTCCTATCCGA (SEQ ID NO: 8) |
| 10 mer RNA | AAAGGUGCGU (SEQ ID NO: 9) |
| 20 mer RNA | AAAGGUGCGUUUAUAGAUCU (SEQ ID NO: 10) |
| 40 mer RNA | AAAGGUGCGUUUAUAGAUCUAGACUAGGUUGCAGCAACUA (SEQ ID NO: 11) |
| 40 mer DNA Modular Capture Probe | $NH_2-(CH_2)_{12}-$ TAGTTGCTGCAACCTAGTCTAGATCTATAAACGCACCTTT (SEQ ID NO: 12) |
| 54 mer DNA Modular Capture Probe | $NH_2-(CH_2)_{12}-$ CTGTTCCTGCTGAACTGAGCCAAAAAAAAAAA CTGTTCCTGCTGAACTGAGCCA (SEQ ID NO: 13) |
| LNA Capture Probe for hsa miR-24-1 | $NH_2-(CH_2)_{12}-$ CTGTTC CTGCTGAACTGAGCCA (SEQ ID NO: 14) |

Modification of ssDNA Capture Probes

DNA capture probes were resuspended in PBS, pH 7.4 upon arrival from IDT. The probes were buffer exchanged with a new PBS, pH 7.4 solution three times utilizing a Vivaspin® 500 Spin column (MWCO 5000, Sartorius) at 10,000 rpm for 6 min to remove any residual ammonium acetate that would interfere would the subsequent modifications. A solution of succinimidyl-4-formyl benzoate (S-4FB, Solulink) in N,N-dimethylformamide (Fisher) was added in 4-molar excess to the DNA capture probe, and allowed to react overnight. The DNA solution was buffer exchanged three additional times with PBS, pH 6.0 to remove any unreacted S-4FB.

Chemical and Biochemical Modification of Silicon Photonic Microring Resonator Surfaces Prior to treatment, sensor chips were cleaned in a fresh solution of Piranha (3:1 solution of 16 M H2SO4:30% wt H2O2) for 1 min, and subsequently rinsed with copious amounts of Millipore H2O. Chips were sonicated for 7 min in isopropanol (Branson 2510 Ultrasonic Cleaner), dried with a stream of N2, and stored until further use.

Chips were immersed in a 1 mg/mL solution of (3-N-((6-(N'-Isopropylidene-hydrazino)-nicotinamide)propyltriethoxysilane) (HyNicSilane, Solulink) for 30 min, and afterwards sonicated for 7 min in 100% EtOH to remove any physisorbed HyNic Silane. The chips were dried with a stream of N2, hand-spotted with 15 µL of DNA modified with a 4-molar excess of S-4FB, and allowed to incubate overnight in a humidity chamber. Prior to experiments, the chips were sonicated in 8 M urea for 7 min to remove any non-covalently bound capture probe.

Addition of Target miRNA to Sensor Surface

Target miRNA solutions were suspended in a high stringency hybridization buffer, consisting of 30% Formamide, 4×SSPE, 2.5×Denhardt's solution (USB Corp.), 30 mM EDTA, and 0.2% SDS, in Millipore H2O. The target miRNA solution (35 µL) was recirculated across the sensor surface at a rate of 24 µL/min for 1 hr utilizing a P625/10K.133 Instech miniature peristaltic pump. Solution was delivered to the chip surface via a microfluidic device consisting of a 0.007" Mylar gasket sandwiched between a Teflon cartridge and the sensor chip. Gaskets were laser etched by RMS Laser in various configurations to allow for multiple flow patterns.

Blocking and Addition of S9.6

Following addition of the target miRNA to the sensor surface, the Instech peristaltic pump was switched to an 11 Plus syringe pump (Harvard Apparatus) operated in withdraw mode. The chips were immediately exposed to Starting Block™ (PBS) Blocking Buffer (Thermo Scientific) for 30 min at 10 µL/min to block the sensor surface and help prevent fouling of S9.6 onto the sensor surface. After, PBS pH 7.4 with 0.05% TWEEN® (polysorbate) was flowed over the sensor surface at 30 µL/min for 7 min. A 2 µg/mL solution of S9.6 in PBS, pH 7.4 with 0.05% TWEEN® (polysorbate) was flowed over the sensor surface for 40 min at a rate of 30 µL/min.

Generation and Purification of the S9.6 Antibody

HB-8730, a mouse hybridoma cell line expressing a monoclonal antibody highly specific towards DNA:RNA heteroduplexes, was obtained from the American Type Culture Collection (ATCC). The line was cultured and the S9.6 antibody was purified using Protein G and resuspended at a concentration of 0.94 mg/mL in PBS, pH 7.4. The antibody solution was aliquoted and stored at −20° C. until use.

Data Analysis

To utilize the S9.6 response for quantitative purposes, the net sensor response after 40 min of exposure to a 2 µg/mL solution of S9.6 was used. Control rings functionalized with a non-complementary DNA capture probe were employed to monitor non-specific hybridization-adsorption of the target miRNA as well as the non-specific binding of the S9.6 antibody. Furthermore, the signal from temperature reference rings (rings buried underneath a polymer cladding layer on the chip) was subtracted from all sensor signals to account for thermal drift.

Figure 13:
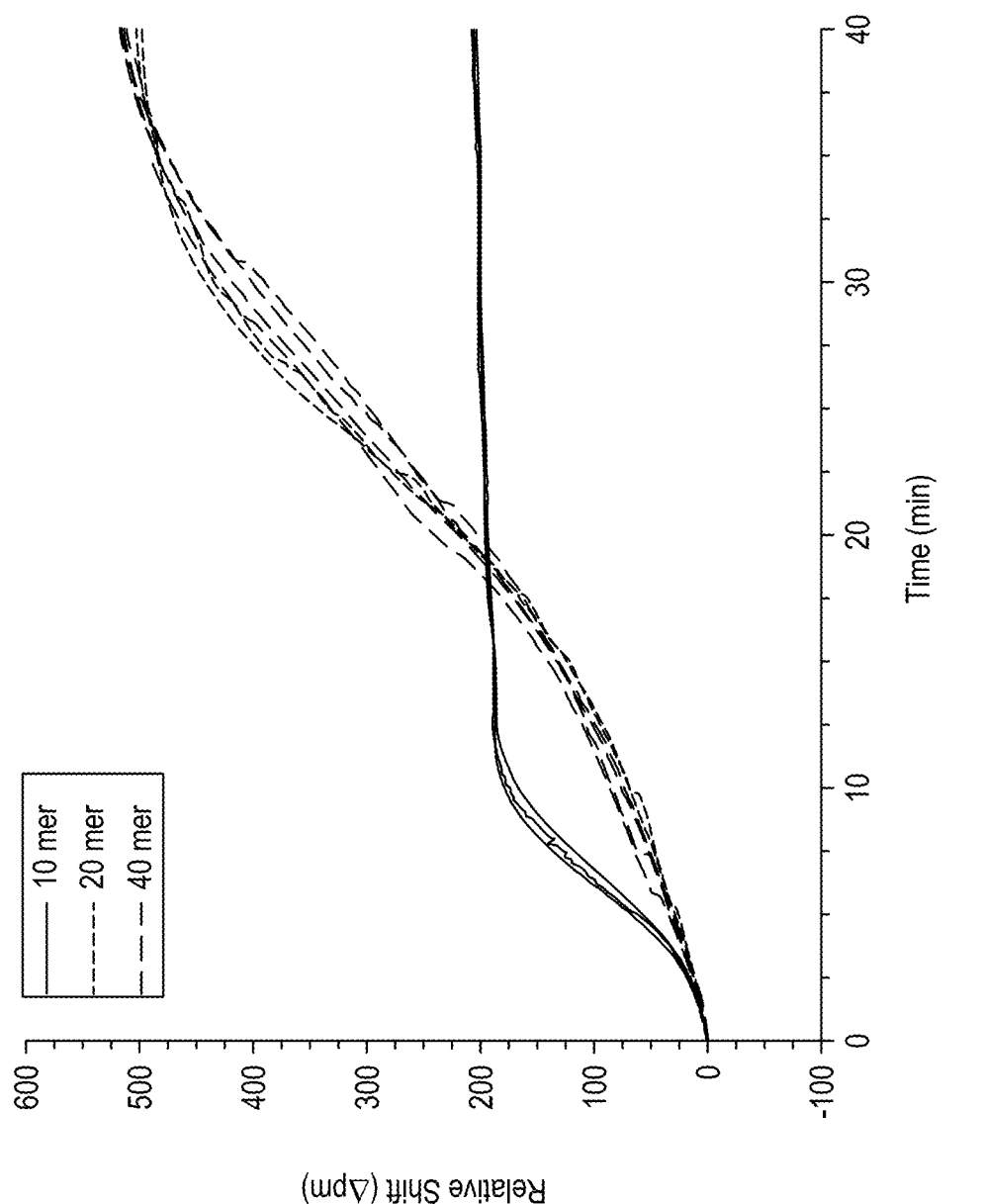
FIG. 13 is a graph showing the amplification response to microrings saturated with a 10mer RNA, 20mer RNA, or 40mer RNA bound to a 40mer ssDNA capture probe in terms of relative wavelength shift over time.

Calibration data was fit with the logistic function:

$$f(c) = (A_1/A_2)/(1+(c/c_0))+A_2$$

over a concentration range from 10 pM to 40 nM, with the exception of miRNA miR-16 (in which the 40 pM and 10 pM points were not obtained). Fitting Parameters used in generating the logistic function for miR-16, miR-21, miR-24-1, and miR-26a are shown in Table 3.

was created with a single 40mer ssDNA capture probe, and subsequently exposed it to three separate RNA sequences, a 10mer, 20mer, and 40mer (Table 2). As shown in FIG. 13, the S9.6 binding response increased significantly from the 10mer to 20mer target RNA, indicating that additional antibodies are bound to the surface, despite the approximately same number of DNA:RNA heteroduplexes. While the increase in S9.6 signal between the 10mer and 20mer target RNAs was roughly proportional to the target RNA length, this trend did not hold between the 20mer and 40mer. This could be due to steric hindrance of the antibodies at the sensor surface; that is, the binding of antibodies to the duplexes prohibited additional antibodies from reaching potential binding sites closer towards the sensor surface. The S9.6 binding epitope appeared to be <10 base pairs in length, a shorter length than reported previously.

Figure 14:
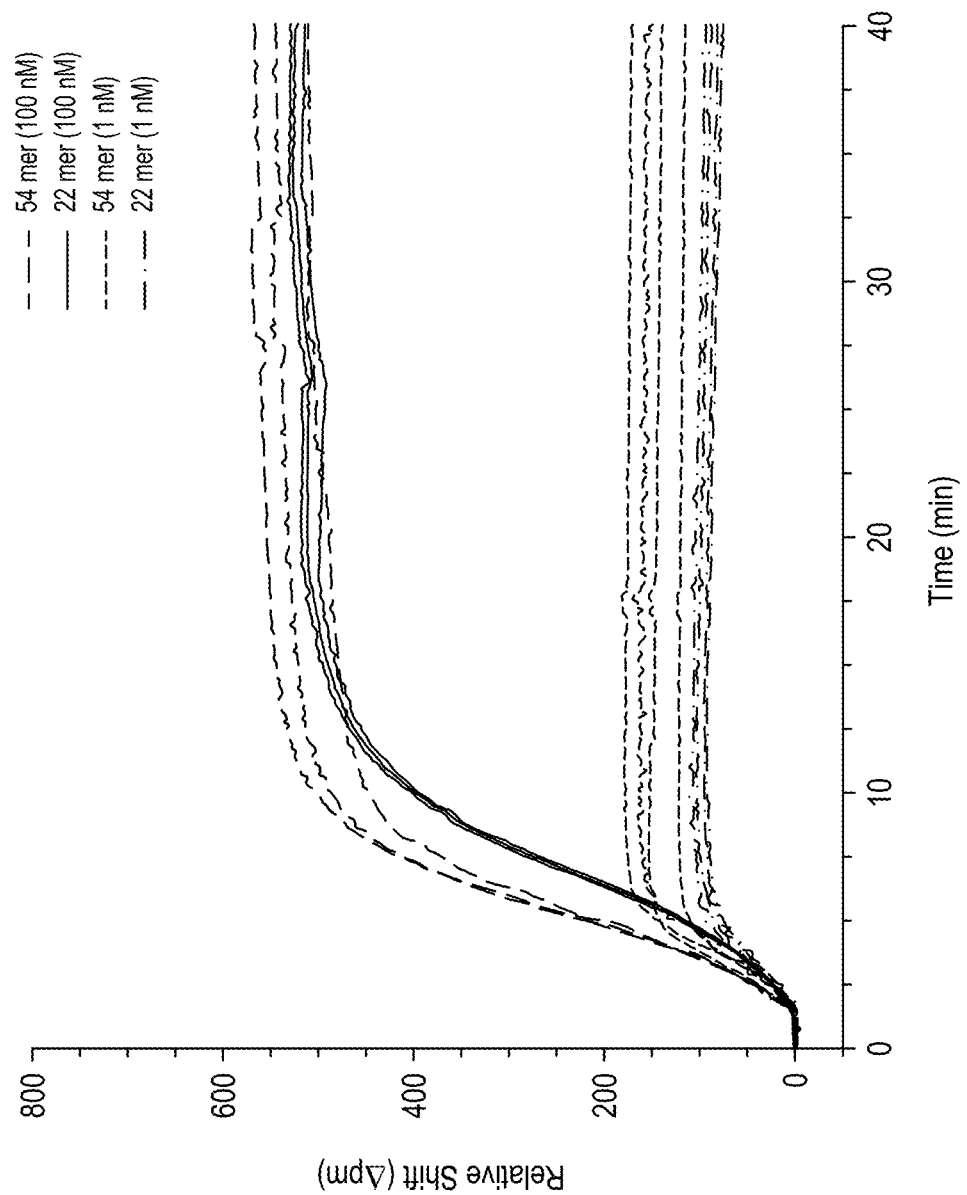
FIG. 14 shows S9.6 amplification response towards: 100 nM miR-24-1 with a 22mer capture probe, 100 nM miR-24-1 with a 54mer capture probe, 1 nM miR-24-1 with a 22mer capture probe, and 1 nM miR-24-1 with a 54mer capture probe in terms of relative wavelength shift over time.

To further interrogate the steric dynamics of S9.6 duplex binding, two ssDNA capture probes were designed—a 22mer capture probe completely complementary towards miR-24-1, and a second 54mer probe containing two binding regions completely complementary towards miR-24-1, separated by an A10 spacer. Assuming near saturation of the DNA capture sites with target miRNA based on the high concentration of miRNA and ionic strength of the hybridization buffer, twice as many S9.6 binding sites are available on the 54mer capture probe than the 22mer. Furthermore, the A10 stretch in the 54mer capture probe prevents complicating interactions between the upper and lower binding sites. As evident in FIG. 14, the S9.6 response for the 54mer capture probes was not double those of the 22mer despite the doubling of bound target miRNA, indicating a steric hindrance of the S9.6 binding.

To test the specificity of S9.6, two separate sets of sensors were functionalized with ssDNA capture probes comple-

TABLE 3

|  | $A_1$ | $A_2$ | $x_0$ | p | Reduced $\chi^2$ | Adjusted $R^2$ |
| --- | --- | --- | --- | --- | --- | --- |
| miR-16 | −4.05391 | 822.84786 | 5.81162 | 0.76797 | 2.12313 | 0.99675 |
| miR-21 | −12.11204 | 678.14618 | 2.23278 | 0.76436 | 31.47097 | 0.98835 |
| miR-24-1 | −35.39772 | 724.61159 | 1.61375 | 0.60747 | 0.93902 | 0.99921 |
| miR-26a | 9.22087 | 753.802 | 3.2261 | 0.69393 | 9.34387 | 0.96113 |

Results

Figure 12A:
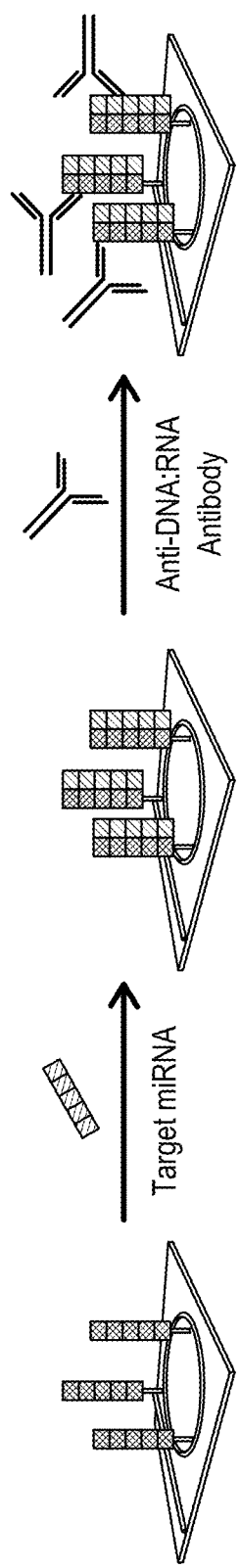
FIG. 12A shows a schematic diagram of the S9.6 amplification assay. A microring is covalently modified with ssDNA capture probes on its surface. The sensor is exposed to a solution containing the target miRNA, after which the S9.6 antibody is flowed across the surface, binding only to DNA:RNA heteroduplexes.
Figure 12B:
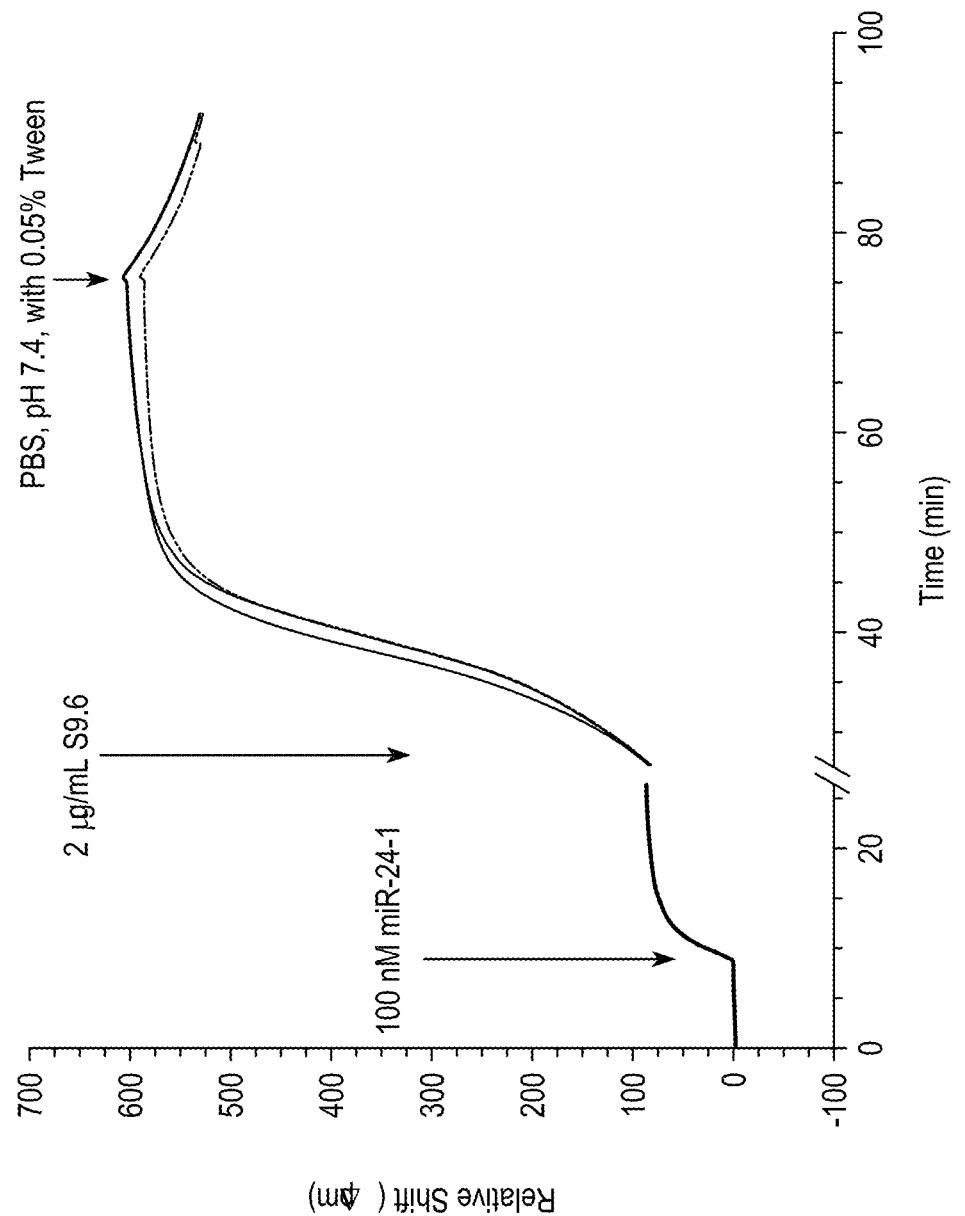
FIG. 12B is a graph showing the signal response from 3 separate microrings corresponding to the schematic in FIG. 12A.

A schematic of the S9.6 assay is shown in FIG. 12A. The microrings were initially functionalized with ssDNA capture probes complementary to the target miRNAs of interest. A solution containing the miRNA was flowed across the sensor surface, after which the surface is blocked with a protein mixture, and subsequently exposed to the S9.6 antibody. A representative response of 3 microrings corresponding to the schematic is shown in FIG. 12B.

An interesting aspect of the S9.6 antibody was the large signal amplification observed upon S9.6 binding to sensor surfaces, especially under nonsaturating conditions. As shown in FIG. 12B, the net shift for the hybridization-adsorption of a 100 nM solution of miR-24-1 (a concentration that will saturate binding sites) onto the sensor surface was ~80 pm. The S9.6 response for amplification was ~520 pm, limited by steric crowding of the antibody. However this secondary amplification became even more dramatic at nonsaturating miRNA conditions, increasing the response over 100-fold.

Figure 15A:
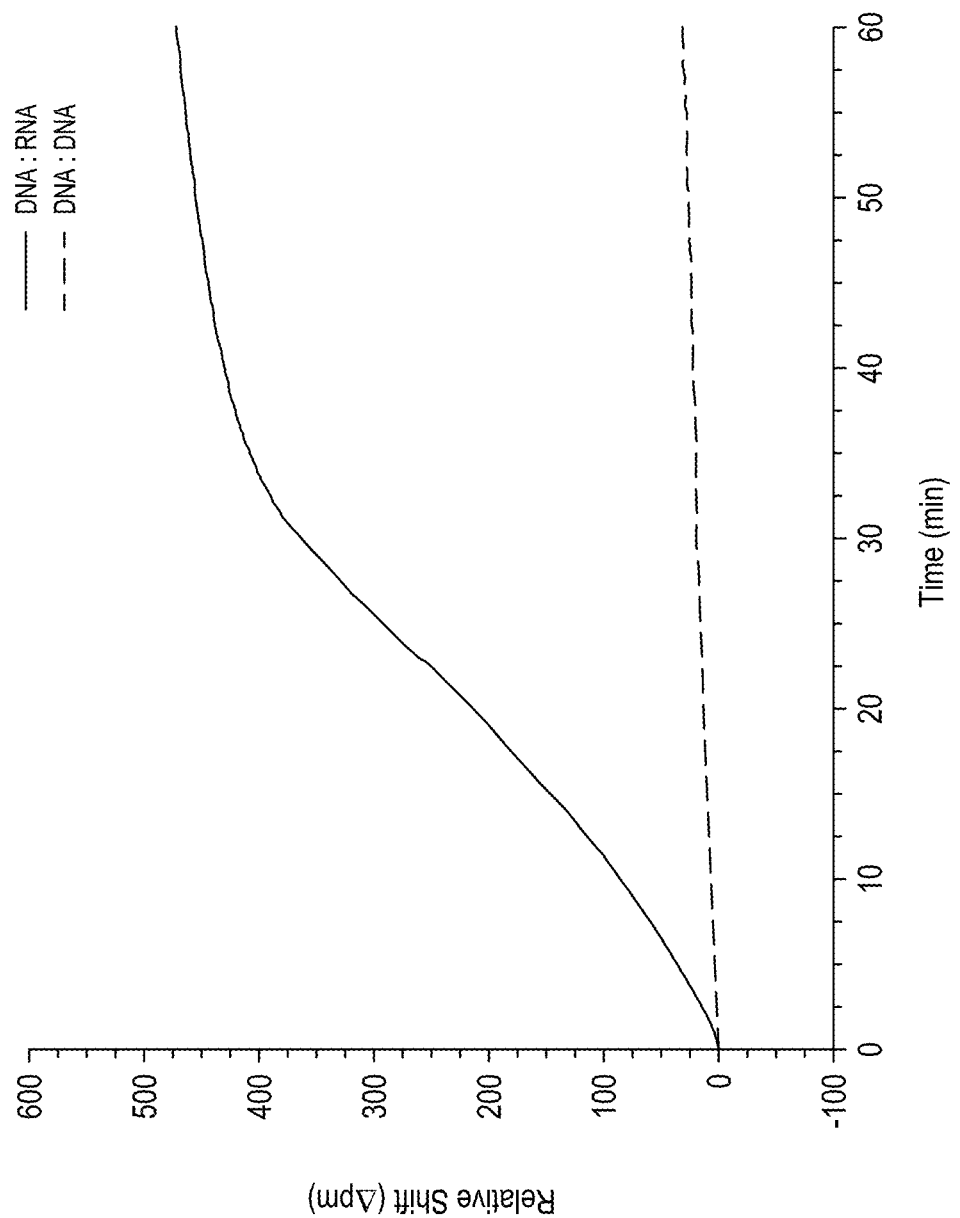
FIG. 15A is a graph showing the real time response of S9.6 amplification towards a DNA:DNA homoduplex and a DNA:RNA heteroduplex in terms of relative wavelength shift over time.

To determine whether a single DNA:RNA heteroduplex could be bound by multiple S9.6 antibodies, a sensor surface mentary towards miR-24-1, and exposed to 1 µM solutions of miR-24-1 and the DNA version of the same sequence to ensure no sequence bias. A representative S9.6 response for an DNA:RNA heteroduplex and DNA:DNA homoduplex were compared in FIG. 15A. Even with the sensor surface fully saturated with DNA:DNA duplexes, the non-specific binding response of the S9.6 was 28 pm, ~6% of the heteroduplex signal, indicating an extremely low non-specific response.

Figure 15B:
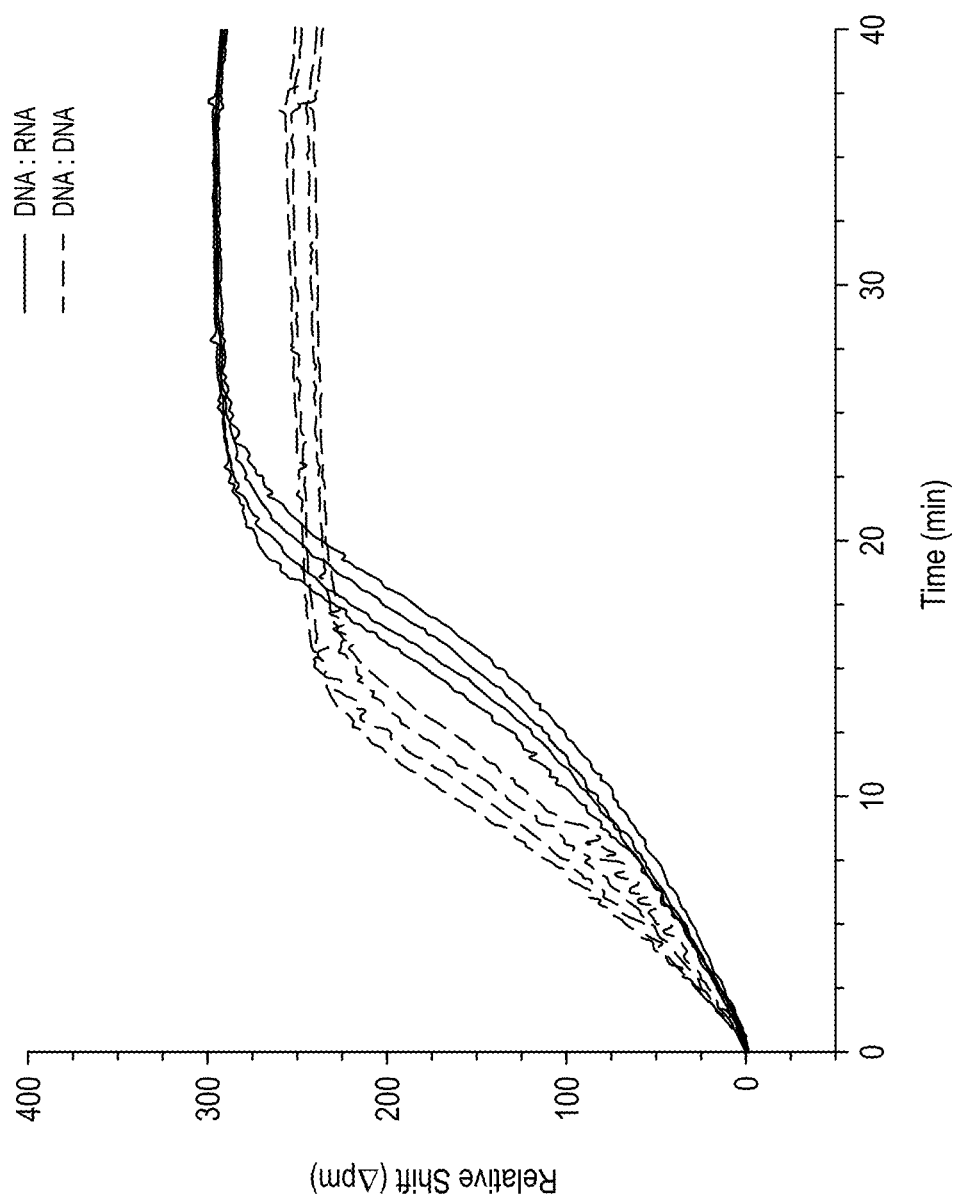
FIG. 15B is a graph showing the response of S9.6 amplification towards a DNA:DNA homoduplex and a DNA:RNA heteroduplex under saturation conditions in terms of relative wavelength shift over time.

To further gauge the binding properties of the antibody, a sensor containing ssDNA and single-stranded locked-nucleic acid (LNA) capture probes, both complementary towards miR-24-1, was created. LNAs are synthetic oligonucleotides containing a 2'-O, 4'-C-methylene bridge which confers added rigidity to the duplex. Spaced periodically in an oligonucleotide, LNAs have been shown to increase the specificity of complementary sequences and raising the Tm values by 3-8° C. per nucleotide. Even though LNAs convert the ssDNA helix into an A-form from the native B-form, as seen in FIG. 15B both the DNA:RNA and LNA:RNA heteroduplexes are bound by S9.6.

Example 2

Multiplex Optical Sensor Detection and Measurement of miRNA Levels in Tissue Sample miRNA levels in mouse brain tissue were measured. The microring resonators, capture probes, and S9.6 antibody were prepared as in Example 1. 50 µg of total mouse brain RNA (Clontech) was diluted 1:5 with hybridization buffer and recirculated overnight prior to amplification with S9.6. The net sensor response after 40 min exposure to 2 µg/mL S9.6 was calibrated to each miRNA to account for variable Tm values and any secondary structure.

Figures 1, 16:
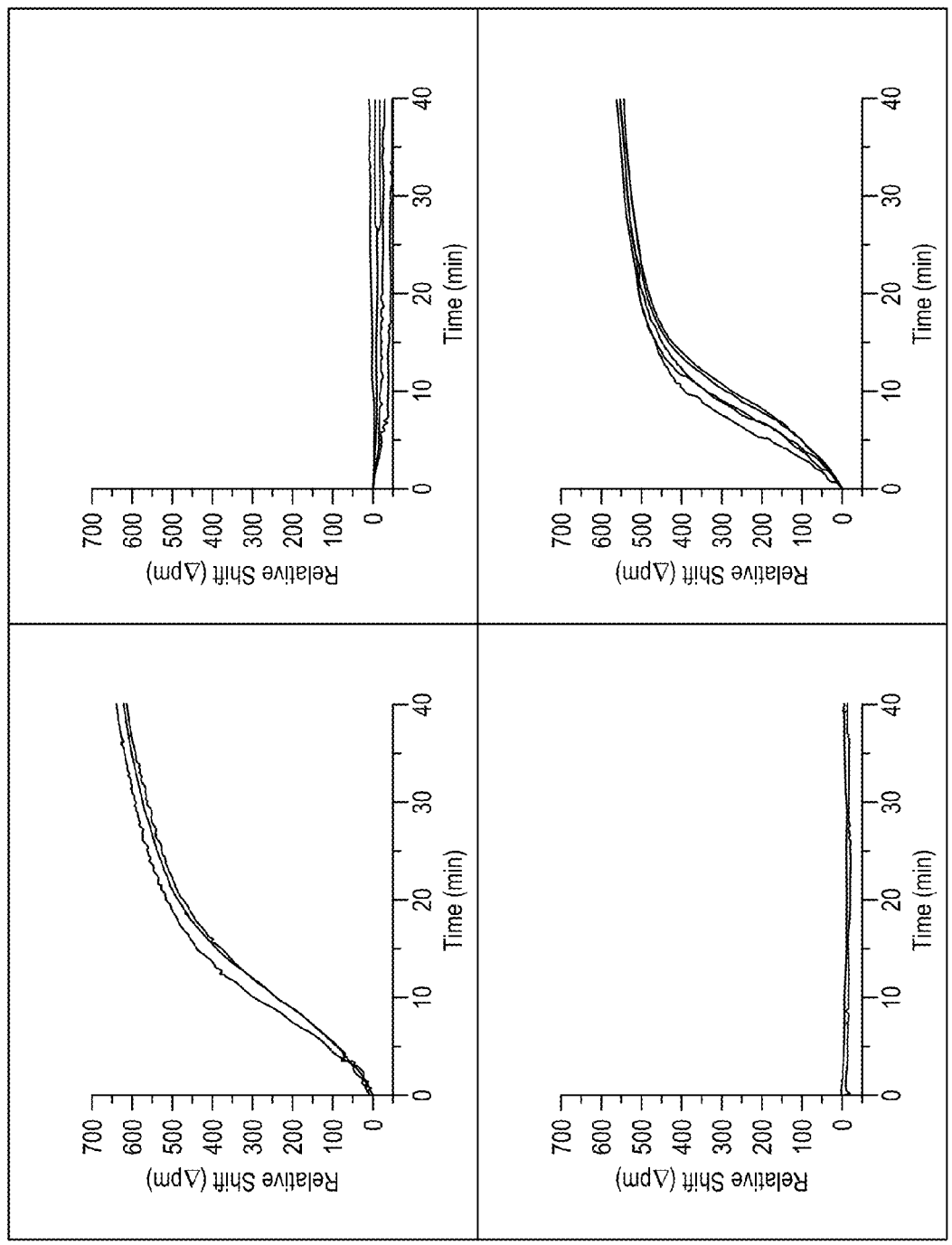
Figures 2, 16:
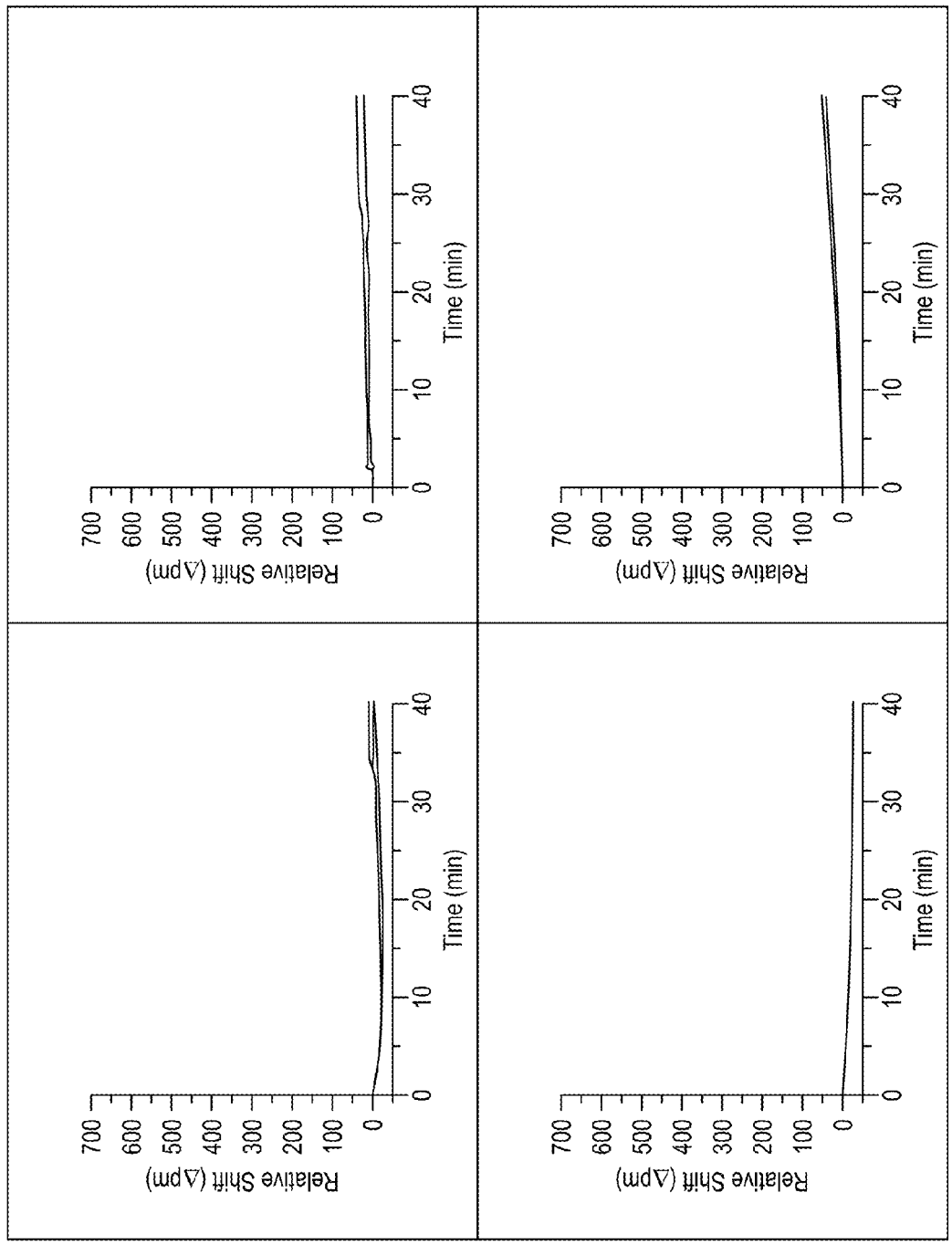
Figures 3, 16:
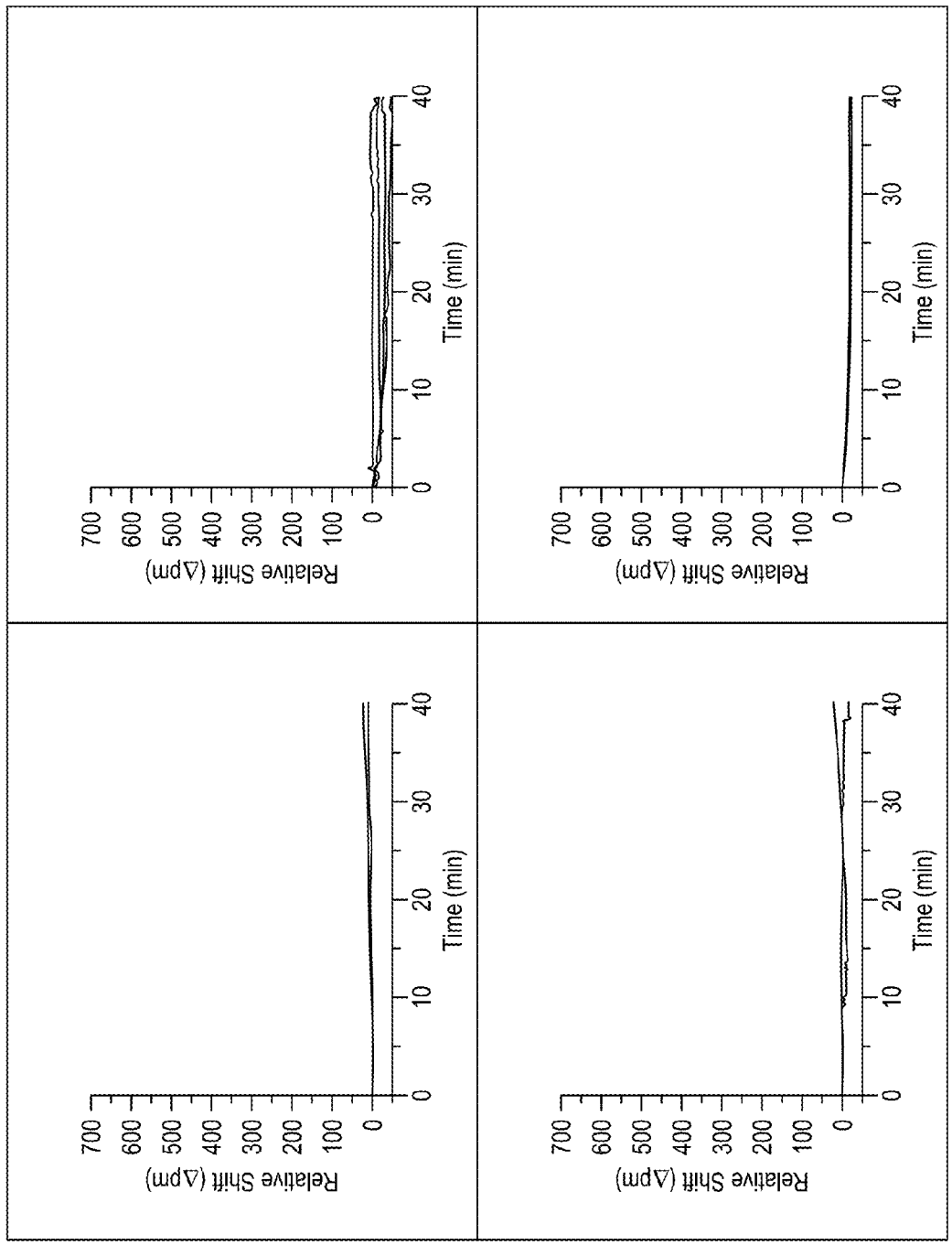
Figure 16:
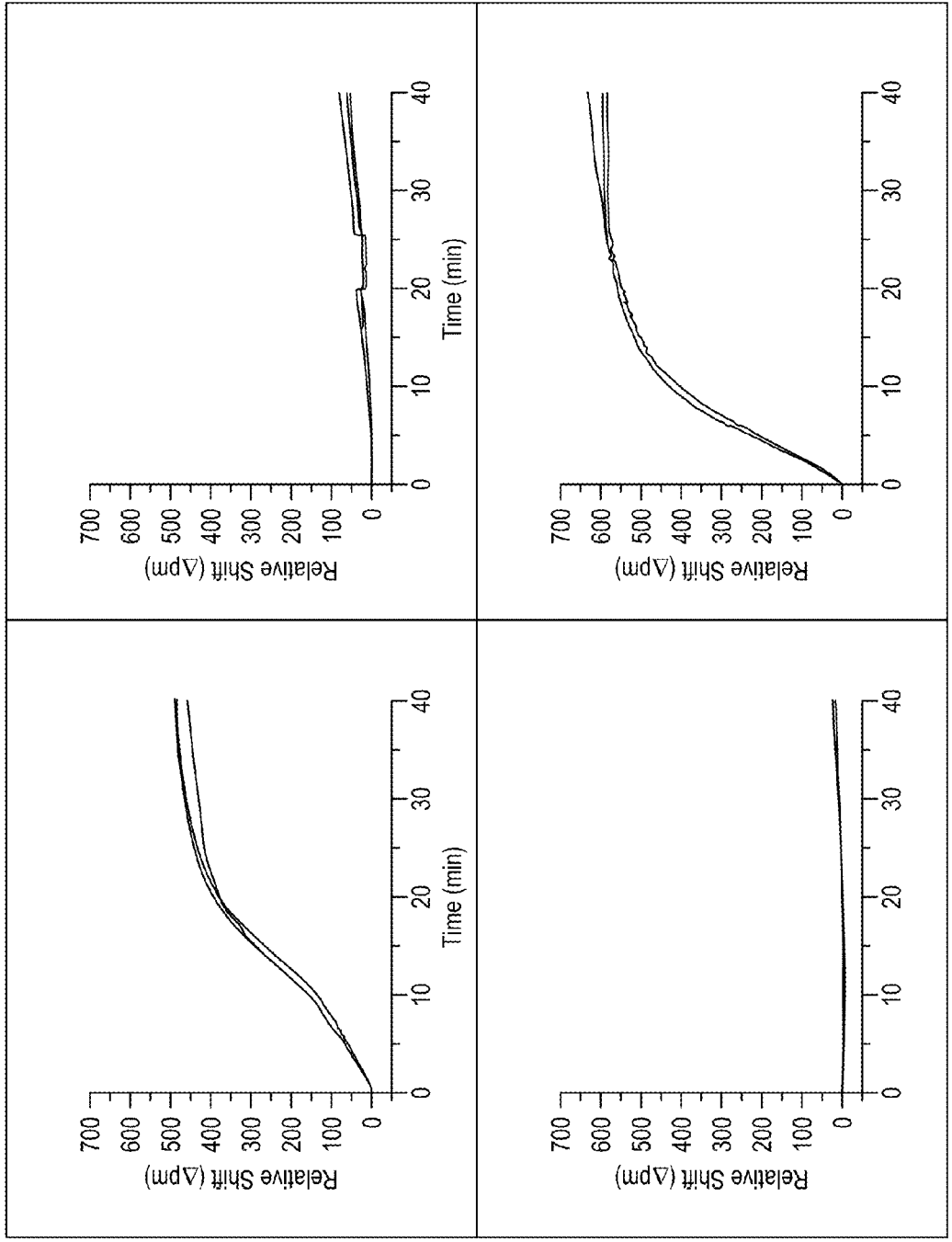
Figure 18A:
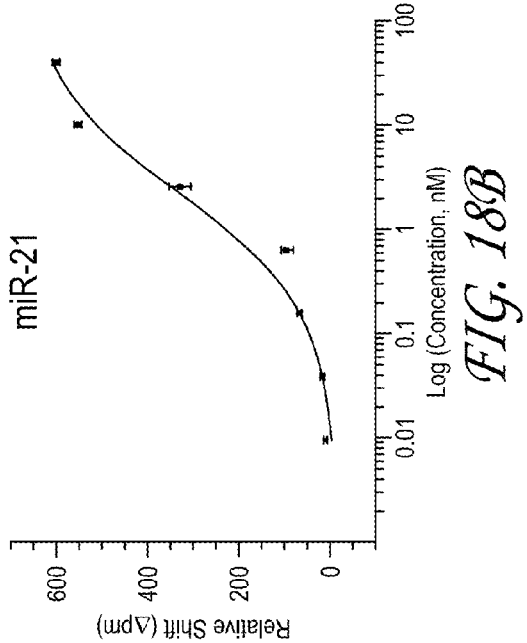
FIG. 18 shows calibration curves for the S9.6 response for miR-16 (FIG. 18A), miR-21 (FIG. 18B), miR-24-1 (FIG. 18C), and miR-26a (FIG. 18D) that represent the logistic fits to the data points. Error bars represent ±1 standard deviation for between 4 and 12 independent measurements at each concentration.
Figure 18B:
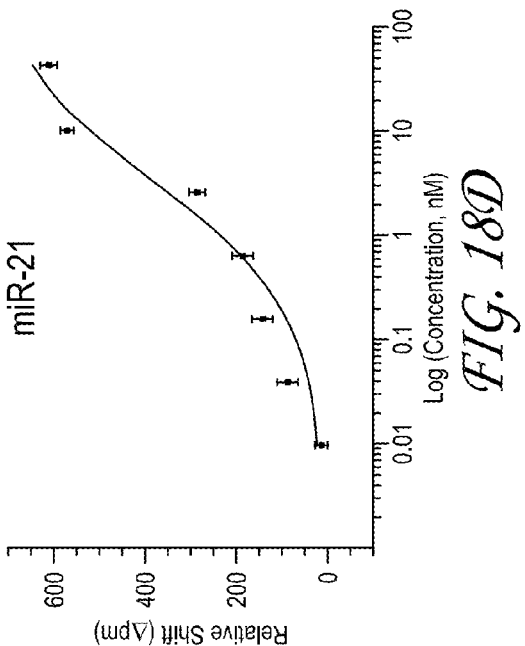
Figure 18C:
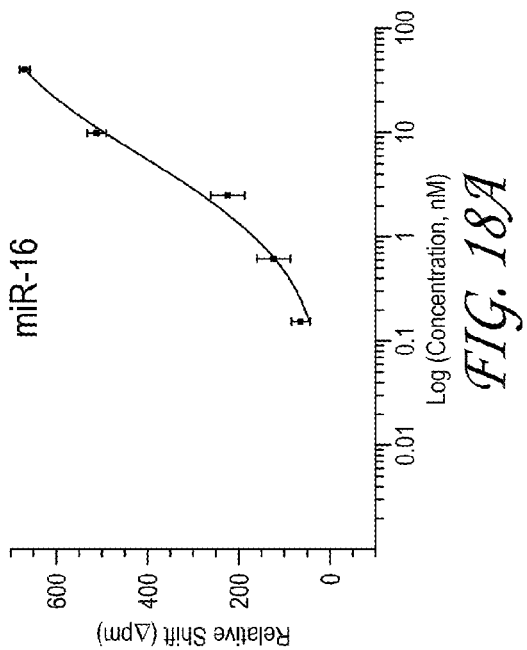
Figure 18D:
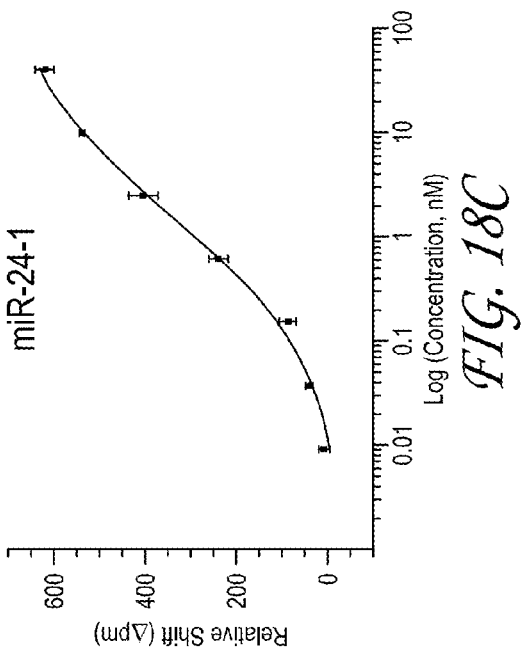

To detect several miRNAs in a sample in multiplex, a single chip containing ssDNA capture probes towards miR-16, miR-21, miR-24, and miR-26a was created. The probes demonstrated no discernable cross-talk even at high concentrations (FIG. 16), due to the sequence non-complementarity and high stringency of the hybridization buffer.

The relative expression profiles of the four aforementioned miRNAs in mouse total brain RNA were analyzed. Mouse brain RNA was used due to its commercial availability as well as literature precedent characterizing the relative expression of some of the aforementioned miRNAs. Three of the sequences are established as being overexpressed in the mouse brain, while expression levels for miR-24-1 have not yet been established. An 8-point calibration curve for each of the target miRNAs (with the exception of miR-16, which included 6 separate concentrations) was generated using synthetic miRNAs in buffer on separate chips (FIGS. 17 and 18). Table 4 summarizes the average net shifts, standard deviations, and number of measurements for each miRNA, at every concentration used in generating the calibration curves.

TABLE 4

| Concentration | Average Net Shift (Δpm) | Standard Deviation (Δpm) | n |
|---|---|---|---|
| miR-16 | | | |
| 40 nM | 667.8233 | 11.68674 | 6 |
| 10 nM | 511.1485 | 20.73502 | 10 |
| 2.56 nM | 223.4956 | 36.97746 | 10 |
| 640 pM | 126.107 | 37.4514 | 12 |
| 160 pM | 66.18232 | 21.82598 | 12 |
| 0 pM | −4.6422 | 4.676103 | 12 |
| miR-21 | | | |
| 40 nM | 600.5059 | 4.884918 | 6 |
| 10 nM | 552.0066 | 8.021747 | 10 |
| 2.56 nM | 328.4126 | 23.88331 | 7 |
| 640 pM | 95.49972 | 12.97273 | 8 |
| 160 pM | 67.16636 | 4.670938 | 7 |
| 40 pM | 17.8158 | 1.7194 | 12 |
| 10 pM | 9.373472 | 1.87066 | 6 |
| 0 pM | −20.9375 | 1.896485 | 12 |
| miR-24-1 | | | |
| 40 nM | 618.8836 | 20.21606 | 11 |
| 10 nM | 537.5413 | 6.39932 | 10 |
| 2.56 nM | 403.696 | 32.5795 | 12 |
| 640 pM | 239.1976 | 18.63782 | 12 |
| 160 pM | 87.22411 | 18.20515 | 10 |
| 40 pM | 40.13903 | 7.246751 | 10 |
| 10 pM | 8.668097 | 11.29013 | 11 |
| 0 pM | −35.7432 | 2.210016 | 11 |
| miR-26a | | | |
| 40 nM | 608.6443 | 19.12271 | 11 |
| 10 nM | 569.5448 | 14.52657 | 8 |
| 2.56 nM | 285.0542 | 18.44371 | 4 |
| 640 pM | 185.4222 | 23.101 | 9 |

TABLE 4-continued

| Concentration | Average Net Shift (Δpm) | Standard Deviation (Δpm) | n |
|---|---|---|---|
| 160 pM | 141.0185 | 21.39422 | 11 |
| 40 pM | 88.14865 | 24.61825 | 5 |
| 10 pM | 13.80172 | 13.57775 | 10 |
| 0 pM | 1.818311 | 10.73274 | 10 |

Figure 19:
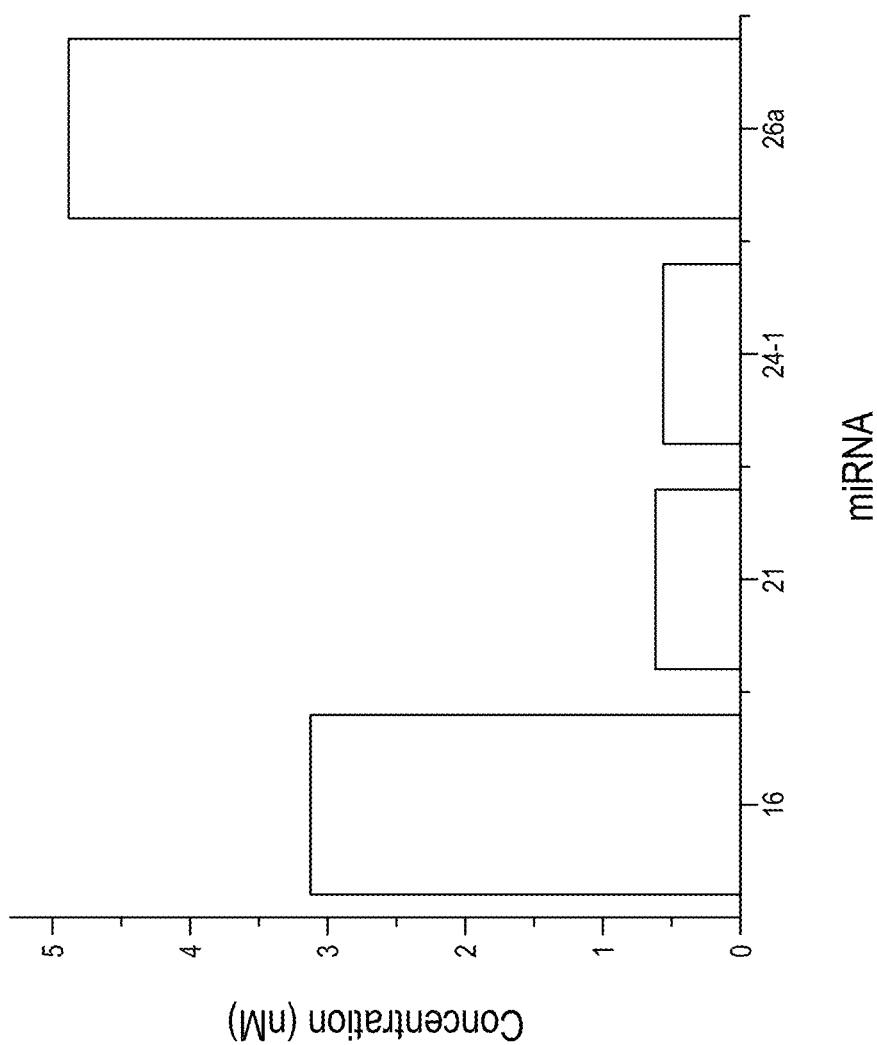
FIG. 19 is a bar graph showing a comparison of the concentrations for each of the four target miRNAs (miR-16, miR-21, miR-24-1, and miR-26a) in total mouse brain RNA.

The expression of the aforementioned miRNAs was analyzed in total mouse brain RNA, and after calibration and accounting for the 5 fold dilution in hybridization buffer, original expression levels were determined to be 3.12 nM, 0.60 nM, 0.56 nM, and 4.87 nM for miR-16, miR-21, miR-24-1, and miR-26a, respectively (FIG. 19). The overexpression of miR-16 and miR-26a relative to miR-21 was consistent with previous literature reports. Table 5 summarizes the S9.6 shifts for total mouse brain RNA and derived concentrations.

TABLE 5

| | Average Net Shift (Δpm) | Standard Deviation (Δpm) | n | Concentration (nM) |
|---|---|---|---|---|
| miR-16 | 122.1655 | 36.76069 | 8 | 3.1185 |
| miR-21 | 54.39331 | 27.2849 | 8 | 0.597 |
| miR-24-1 | 89.7634 | 23.45957 | 9 | 0.557 |
| miR-26a | 235.10568 | 55.97535 | 9 | 4.8485 |

Figure 20:
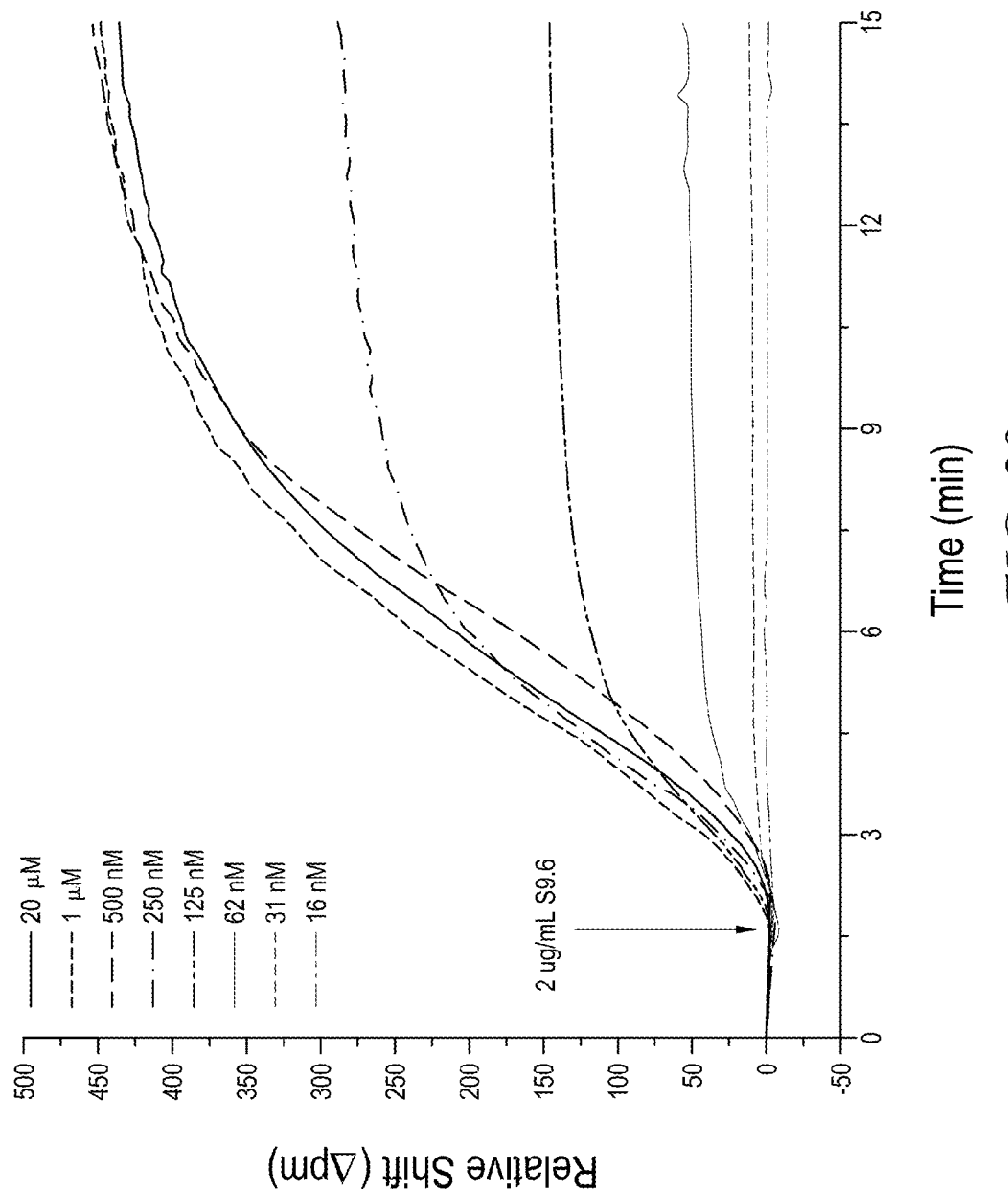
FIG. 20 is a graph showing the S9.6 response in terms of relative wavelength shift over time to varied ssDNA capture probe concentrations with a constant miR-24-1 target concentration (40 nM).

An interesting observation throughout the course of these studies was the sigmoidal nature of the S9.6 binding that occurred at high target miRNA concentrations. Further experiments with various capture probe concentrations revealed that the shape of the binding curve was, in part, dependent on the capture probe density, as shown in FIG. 20. At high capture probe densities, the binding becomes sigmoidal in nature, while at low densities, the binding curves take on a logarithmic shape that characteristic of a Langmuir binding isotherm. It appears that at high capture probe densities or target probe concentrations, the initial S9.6 binding stabilized the DNA:RNA heteroduplex structure, making it easier for additional antibodies to bind. This collaborative binding effect would explain the sigmoidal shape, but does not account for the slow initial binding rate of the antibody. One possible explanation might be that the DNA:RNA duplexes acted as an anti-fouling surface for the antibody. Once S9.6 initially bound to the primarily nucleic acid surface, it disrupted some of the biofouling properties, allowing other antibodies to bind nearby as well.

Example 3

Signal Amplification with Nanoparticles

Optical sensor signal amplification was achieved using capture agents tagged with either organic or inorganic nanoparticles. Sequential immunoassays were performed for purified interleukins 2 and 4 (IL-2 and IL-4) using biotinylated secondary antibodies against both, but then included a further amplification step for IL-2 via a tertiary recognition event with streptavidin-coated CdSe quantum dots.

Materials

3-N-((6-(N'-Isopropylidene-hydrazino))nicotinamide) propyltriethyoxysilane (HyNic silane) and succinimidyl 4-formyl benzoate (S-4FB) were purchased from SoluLink (San Diego, Calif.). Monoclonal mouse anti-human IL-2 and IL-4 (capture antibody, material #555051, clone 5344.111)], monoclonal biotin mouse anti-human IL-2 (detection antibody, catalog #555040, clone B33-2) and monoclonal biotin mouse anti-human IL-4 (detection antibody, detection antibody, material #555040, clone B33-2)], in phosphate buffered saline (PBS) containing 0.09% sodium azide, were purchased from BD Biosciences (San Jose, Calif.). These served as the primary and secondary antibodies, respectively. Recombinant human IL-2 (catalog#14-8029) in PBS (pH 7.2, with 150 mM NaCl and 1.0% BSA) was purchased from eBioscience (San Diego, Calif.). PBS was reconstituted in deionized water from Dulbecco's phosphate buffered saline packets purchased from Sigma-Aldrich (St. Louis, Mo.). Aniline was obtained from Acros Organics (Geel, Belgium). Phorbol 12-myristate 13-acetate (PMA, Product#P 1585) was purchased from Sigma-Aldrich and dissolved in dimethyl sulfoxide to 0.5 mg/mL. The lectin phytohemagglutinin (PHA-P) from *Phaseolus vulgaris* (Product#L 9132) was also purchased from Sigma-Aldrich and dissolved in PBS, pH 7.4 to 0.5 mg/mL. Zeba spin filter columns were obtained from Pierce (Rockford, Ill.). Cell culture media, RPMI 1640 supplemented with 10% fetal bovine serum (FBS) and penicillin/streptomycin (100 U/mL each), was obtained from the School of Chemical Sciences Cell Media Facility at the University of Illinois at Urbana-Champaign. All other chemicals were obtained from Sigma-Aldrich and used as received.

Qdot® 525 streptavidin conjugates (CdSe core with ZnS coating) were purchased as a 1.0 μM solution in 50 mM borate buffer, pH=8.3, with 1.0 mM Betaine and 0.05% sodium azide from Molecular Probes, Inc. (catalog #: Q10141 MP). Prior to the assay, the quantum dots were diluted to 2 nM in 10 mM PBS pH=7.4 with 0.1 mg/mL BSA.

All buffers and dilutions were made with purified water (ELGA PURELAB filtration system; Lane End, UK), and the pH was adjusted with either 1 M HCl or 1 M NaOH. Antibody immobilization buffer was 50 mM sodium acetate and 150 mM sodium chloride adjusted to pH 6.0. Capture antibody regeneration buffer was 10 mM glycine and 160 mM NaCl adjusted to pH 2.2. BSA-PBS buffer used for IL-2 sensor calibration and detection was made by dissolving solid bovine serum albumin (BSA) in PBS (pH 7.4) to a final concentration of 0.1 mg/mL. For blocking, 2% BSA (w/v) in PBS was used.

Silicon photonic microring resonator array chips and the instrumentation for microring resonance wavelength determination were designed in collaboration with and built by Genalyte, Inc. (San Diego, Calif.). Briefly, silicon microring substrates (6×6 mm) contain sixty-four microrings that are accessed by linear waveguides terminated with input and output diffractive grating couplers, allowing independent determination of the resonance wavelength for each microring. Up to thirty-two microring sensors are monitored simultaneously, eight of which are used solely to control for thermal drift. The instrumentation employs computer-controlled mirrors and a tunable, external cavity diode laser (center frequency 1560 nm) to rapidly scan the chip surface and sequentially interrogate the array of microring resonators, allowing determination of resonance wavelength for each independent sensor with ~250 msec time resolution.

Functionalization of Silicon Photonic Microring Resonator Arrays

Prior to functionalizing the microring surfaces, sensor chips were cleaned by a 30-sec immersion in piranha solution (3:1 $H_2SO_4$:30% $H_2O_2$) followed by rinsing with copious amounts of water and drying in a stream of nitrogen gas. For all subsequent steps, sensor chips were loaded into a previously described custom cell with microfluidic flow channels defined by a Mylar gasket (Washburn, A. L.; Gunn, L. C.; Bailey, R. C. Anal. Chem. 2009, 81, 9499-9506), and flow was controlled via an 11 Plus syringe pump (Harvard Apparatus; Holliston, Mass. operated in withdraw mode. Flow rates for functionalization and cytokine detection steps were set to 5 μL/min. The flow rate was set to 30 μL/min for all additional steps.

The chip was first exposed to a solution of 1 mg/mL HyNic silane in 95% ethanol and 5% dimethyl formamide (DMF) for 20 minutes to install a hydrazine moiety on the silicon oxide chip surface, followed by rinsing with 100% ethanol. In a separate reaction vial, the capture antibody was functionalized with an aldehyde moiety by reacting anti-IL-2 (0.5 mg/mL) with a 5-fold molar excess of 0.2 mg/mL S-4FB (dissolved first in DMF to 2 mg/mL for storage and diluted in PBS to 0.2 mg/mL) for 2 hrs at room temperature. After buffer-exchanging to remove excess S-4FB using Zeba spin filter columns and dilution to 0.1 mg/mL, the antibody-containing solution was flowed over the chip to allow covalent attachment to the hydrazine-presenting chip surface. Aniline (100 mM) was added to the antibody solution prior to flowing over the chip, serving as a catalyst for hydrazone bond formation that improves biosensor surface functionalization. The previously-described Mylar gasket (Washburn, A. L.; Gunn, L. C.; Bailey, R. C. Anal. Chem. 2009, 81, 9499-9506) allows for selective antibody functionalization on 15 rings under fluidic control. After the coupling reaction, a low-pH glycine-based regeneration buffer rinse removed any non-covalently bound antibody. A final blocking step was carried out by exposing the sensor surface to a 2% solution (w/v) of BSA in PBS overnight.

Calibration of Sensors and Detection of IL-2 and IL-4

IL-2 and IL-4 calibration standards were prepared by serial dilution of recombinant human IL-2 (≥0.1 mg/mL) and IL-4 in BSA-PBS to the following concentrations: 50, 25, 10, 4, 1.6, 0.64, 0.26, 0.10, and 0 ng/mL. Blinded unknown samples were prepared independently from similar stocks. All sandwich assays performed on the chip surface were monitored in real time and involved a 30-min incubation (5 μL/min) in IL-2 standard, IL-4 standard, or unknown solution followed by a 15-min read-out with the secondary detection anti-IL-2 antibody (2 μg/mL, 5 μL/min) or anti-IL-4 antibody. A low-pH glycine buffer rinse, which disrupts non-covalent protein interactions, was used to regenerate the capture anti-IL-2 and anti-IL-4 surface. The chip was blocked with BSA-PBS prior to subsequent IL-2 and IL-4 detection experiments.

Data Processing

The response from the detection antibody binding to captured IL-2 or IL-4 at the surface as a function of IL-2 or IL-4 concentration was used to calibrate the sensor response for each ring (n=15 independent measurements). Prior to quantitation, the shift response of a control ring, which was not functionalized with capture anti-IL-2 antibody or anti-IL-4 antibody but was exposed to the same solution as the functionalized rings, was subtracted from each of the functionalized ring signals to account for any non-specific binding, as well as temperature or instrumental drift. The corrected secondary signal after 15 minutes of detection antibody incubation was measured as a net shift for each IL-2 and IL-4 standard and unknown, with the signal from each ring serving as an independent measure of IL-2 and IL-4 concentration. The average corrected secondary shift was plotted against concentration to obtain a calibration plot, which was then fit with a quadratic regression for quantitation of unknowns by inverse regression.

Jurkat Cell Culture, Stimulation, and Secretion Profiling

Jurkat T lymphocytes were passaged into fresh media at 106 cell/mL (10 mL culture in each of two T25 vented flasks). One flask was immediately stimulated to secrete IL-2 and IL-4 by adding the mitogens PMA (50 ng/mL) and PHA (2 μg/mL) using an established procedure (Gebert, B.; Fischer, W.; Weiss, E.; Hoffmann, R.; Haas, R. Science 2003, 301, 1099-1102, Weiss, A.; Wiskocil, R.; Stobo, J. J. Immunol. 1984, 133, 123-128, Manger, B.; Hardy, K. J.; Weiss, A.; Stobo, J. D. J. Clin. Invest. 1986, 77, 1501-1506, Sigma-Aldrich Cat#P1585 Datasheet 2002, www.sigmaaldrich.com) while the other flask served as a non-stimulated control. Both flasks were immediately returned to the cell culture incubator (37° C., 5% CO2, 70% relative humidity). Aliquots (1 mL) were withdrawn from both the control and stimulated flasks at four time points: 0, 8, 16, and 24 hours post-stimulation. The cell culture aliquots were centrifuged at 1,000 RPM for 5 min to pellet the cells, and then the supernatant was removed and centrifuged at 10,000 RPM for 5 min to pellet any remaining cellular debris. Cell culture aliquots were divided into two identical tubes and stored for less than 24 hours at 4° C. for subsequent parallel analysis by both ELISA and the microring resonator platform.

A sensor chip was selectively functionalized with anti-IL-2 and IL-4 capture antibody as described above and calibrated to secondary antibody response with the following IL-2 and IL-4 standards prepared by serial dilution in cell culture media: 50, 20, 8, 3.2, and 1.3 ng/mL. Immediately after calibration, aliquots taken at each time point for both control and stimulated cells were flowed over all rings on the chip (30 min, 5 μL/min) followed by introduction of the detection anti-IL-2 and IL-4 (2 μg/mL, 15 min, 5 μL/min).

Figure 21:
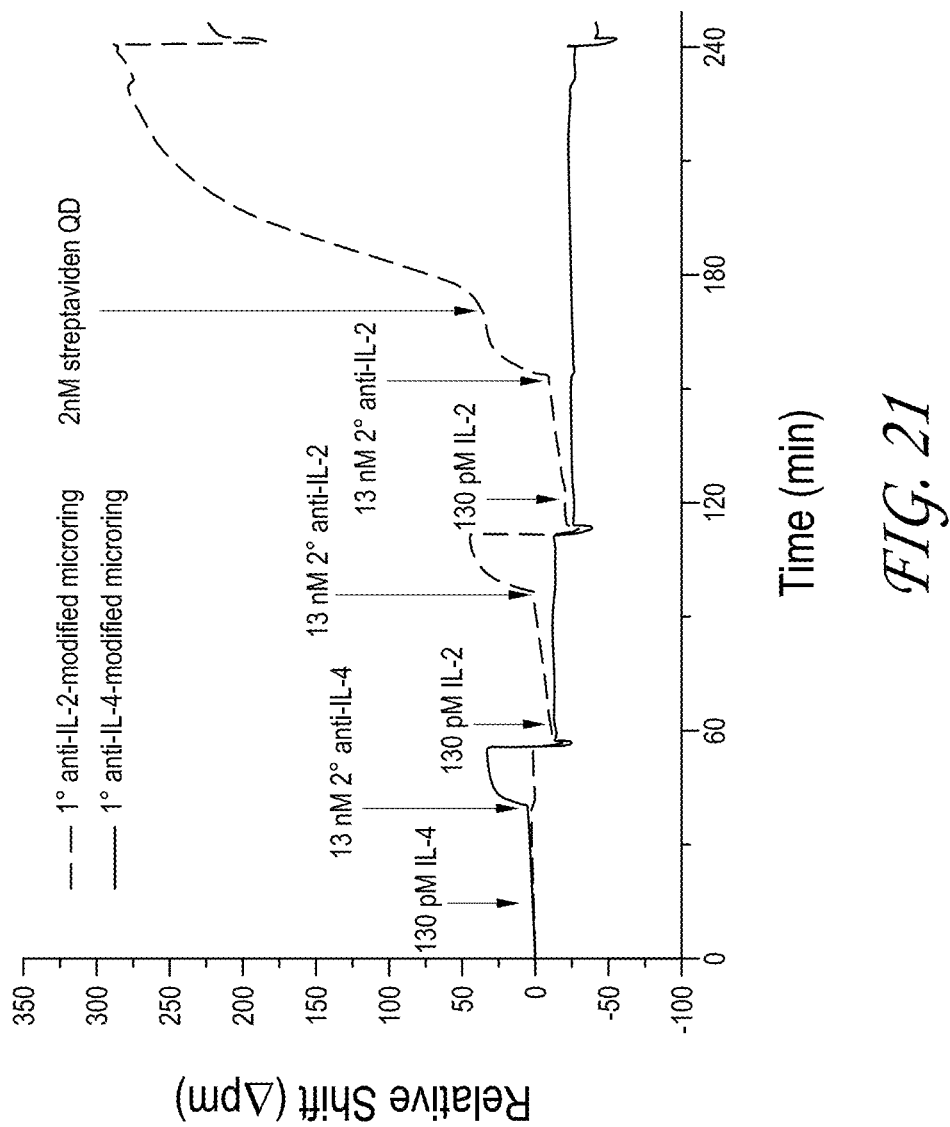
FIG. 21 is a graph showing tertiary binding of streptavidin quantum dots to a biotinylated secondary antibody in terms of relative wavelength shift over time. The tertiary binding lowers the detection limit for the analyte IL-2 by at least 10-fold down to the low 100s of fM.

Once the rings were functionalized with capture anti-IL-2 and IL-4 primary antibodies, a 240-min IL-2 and IL-4 sandwich assay was performed, as shown in FIG. 20. IL-4 (130 pM) was added to the rings, followed by addition of secondary anti-IL-4 antibody (13 nM). Next, IL-2 (130 nM) was added to the rings, followed by addition of secondary anti-IL-2 antibody (13 nM). Then, streptavidin-labeled quantum dots were added. As shown in FIG. 21, the secondary labels allowed detection down to the order of 5 pM, but the addition of the streptavidin-labeled quantum dots provided a large and specific signal, pushing the assay limit of detection down to the low 100s of fM.

Example 4

Single Binding Event Detection and Signal Amplification with Polystyrene Beads

To perform single binding event detection, the binding of commercially-available protein G-coated polystyrene beads to an array of antibody modified microring resonators was monitored in real-time as shown in FIG. 22A. Protein G is a bacterial protein that recognized the FC region of antibodies with high affinity, thus facilitating localization of beads onto the microring surface. Microring resonators were prepared similar to as in Examples 1 and 3.

As shown in FIG. 22A, protein G-coated polystyrene beads induced discrete jumps in relative resonance wavelength shift attributable to individual binding events of single beads or bead aggregates. This data suggests that single binding events are easily resolvable, with most of the stair step responses being >10σ. A similar experiment was carried out measuring the binding of streptavidin-modified polystyrene beads to biotinylated microrings. For this experiment, the number of beads bound to each ring was determined via scanning electron microscopy (SEM) (FIG. 22B) and plotted versus the net resonance wavelength shift of the corresponding ring. The SEA image was stitched from four high resolution images and allowed enumeration of beads bound to a given microring. Only beads directly contacting the ring, and thus safely within the evanescent field, were counted. As shown in the plot of resonance wavelength shifts versus number of bound beads in FIG. 22C, a clear trend was observed between sensor response and bead number, providing strong evidence that single bead binding events are being visualized as "quantized" ~3.5 pm resonance shifts in real time.

Example 5

Figure 23:
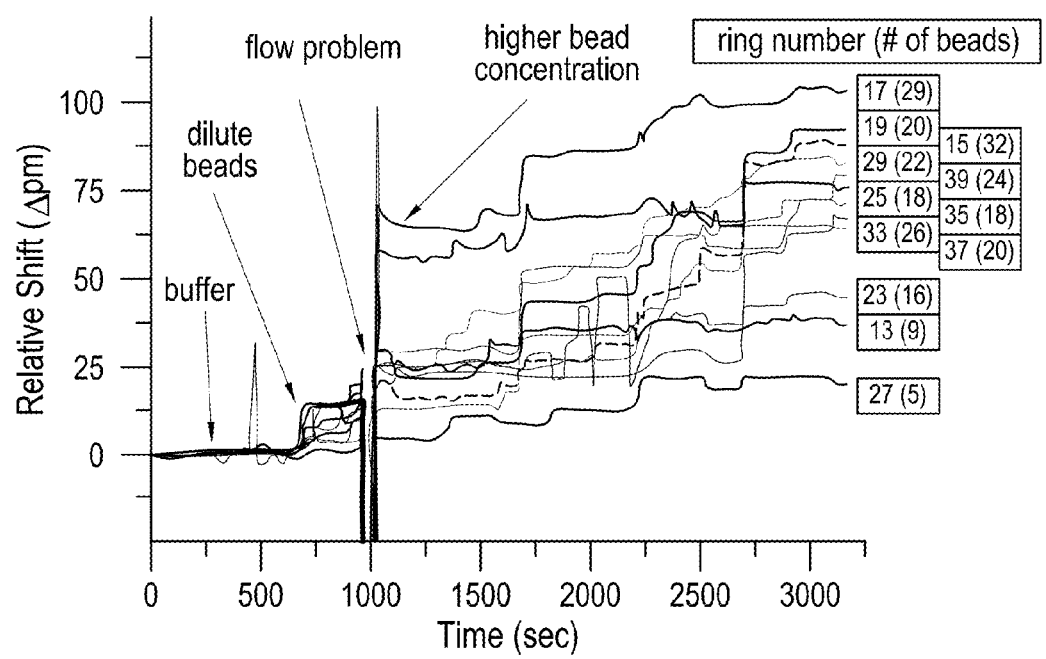
FIG. 23 is a graph showing real-time response of an array of twelve biotin-functionalized microring resonators to avidin-coated latex beads. The resonances show discrete jumps in resonance frequence that can be attributed to individual bead binding events.
Figures 24A, 24B, 24C:
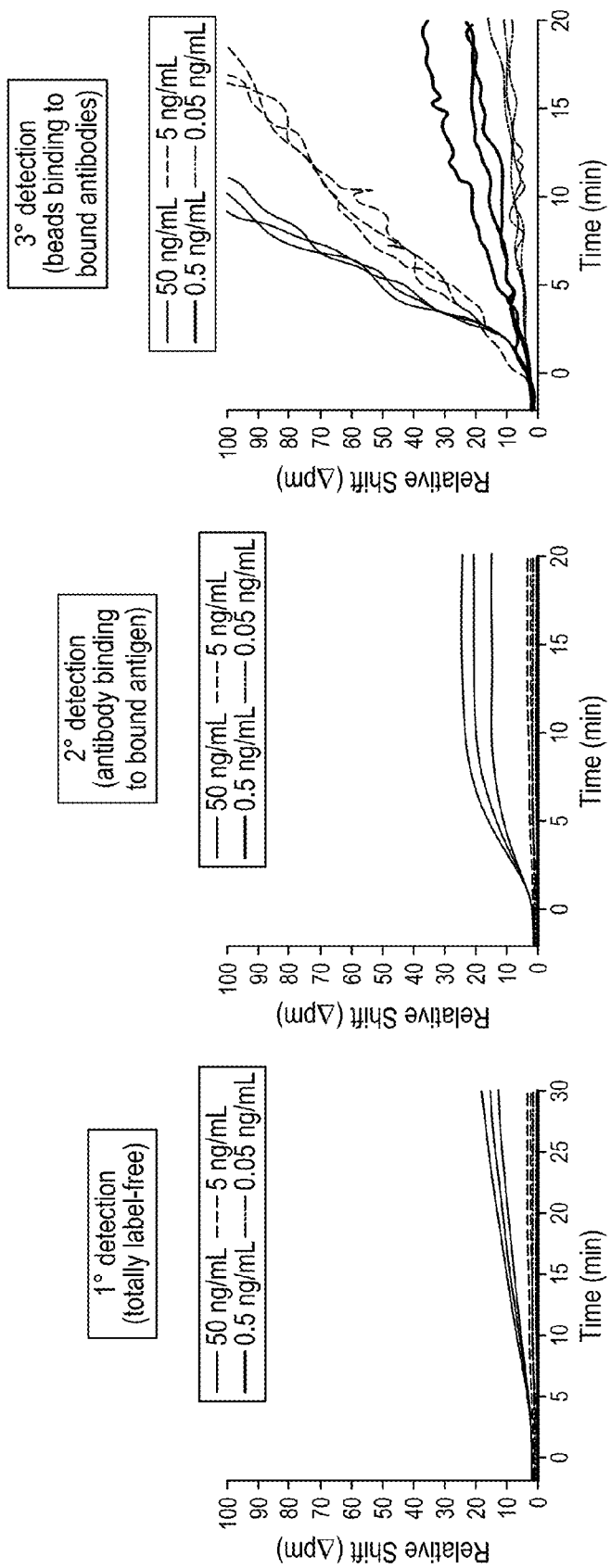
FIGS. 24A-F are graphs showing signal enhancement using secondary antibody and tertiary bead-based detection applied to the detection of the serum cancer biomarker alpha-fetoprotein in terms of relative wavelength shift over time (FIGS. 24A-C) or over concentration (FIGS. 24D-F). Label-free primary binding event detection is shown in FIGS. 24A and 24D, antibody binding to bound antigen secondary binding event detection is shown in FIGS. 24B and 24E, and beads binding to bound antibodies tertiary binding event detection is shown in FIGS. 24C and 24F.
Figures 24D, 24E, 24F:
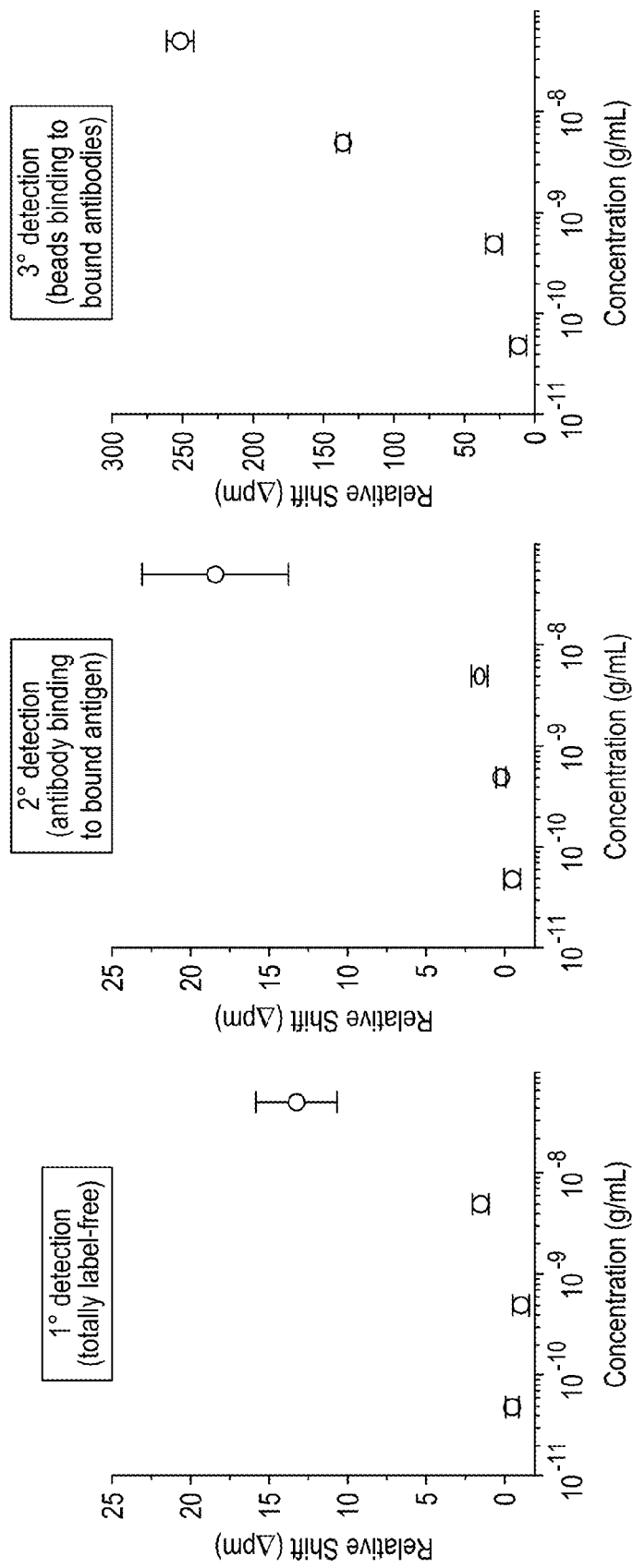

Protein-labeled latex beads were used to generate a measurable sensor response that directly corresponded to an individual binding event. Microrings functionalized with APTES were covalently labeled with biotin using a commercial reagent (NHS-PEO4-biotin, Pierce) and avidin-coated latex beads introduced to the flow channel. As shown in FIG. 23, the real-time sensor response showed discrete jumps in resonance frequency, predominantly to higher values consistent with the increase in the local refractive index due to the binding of a large latex bead. The number of beads bound to each ring was determined via scanning electron microscopy and plotted versus the resonance response of the corresponding ring. A trend was observed between sensor response and bead number providing strong evidence that single bead binding events were being visualized as "quantized" ~3.5 pm resonance shifts in real time. Individual stochastic binding events of bead-labeled biomolecules were detected with the optical micorring resonators.

Example 6

Optical sensors are used for deterministic counting of binding events. 1° antibody-modified microring resonators are incubated with the sample of interest for a defined period. The solution in the flow cell is then replaced with buffer containing a high concentration of nanoparticle-tagged 2° antibodies so that all of the bound target molecules are quickly saturated by the nanoparticle-tagged 2° antibodies. During this process, the number of discrete shifts in resonance wavelength over a defined time period is enumerated.

Example 7

Optical sensors are used for stochastic recording of binding events. Nanoparticle-tagged 2° antibodies are introduced directly into the sample and allowed to associate with the small amount analyte in solution, a process that is expedited by high relative antibody concentrations (2° antibody in excess compared to antigen) and 3-D diffusion. After an appropriate time, this solution is introduced into the sensing chamber and the shifts in resonance wavelength are recorded. Since the localization of nanoparticles at the sensor surface is guided by the interaction between the antigen and 1° antibody (already on the surface), the shifts in resonance wavelength are expected to be transient with the binding and unbinding events having characteristic average time constants that directly relate back to the interaction kinetics. For a simple equilibrium the average time in the "bound" state, $\tau_{off}$, is related to the dissociation rate constant via, $\tau_{off}=1/k_{off}$, and the average time between binding events, $\tau_{on}$, is related to the association rate constant and analyte concentration, $\tau_{on}=1/k_{on}[A]$, as described in Bayley, H; Cremer, P S Stochastic sensors inspired by biology. *Nature* 2001, 413, 226-230.

Example 8

Succinimidyl 4-formylbenzoate (S-4FB), succinimidyl 6-hydrazinonicotinamide acetone hydrazone (S-HyNic), 3-N-((6-(N'-Isopropylidene-hydrazino))nicotinamide)propyltriethyoxysilane (HyNic Silane), and antibody-oligonucleotide conjugation kits were obtained from SoluLink (San Diego, Calif.). Custom DNA oligonucleotides were synthesized by Integrated DNA Technologies (Coralville, Iowa). Monoclonal mouse anti-human AFP antibody clone B491M (referred to as anti-AFP-B491M) was purchased from Meridian Life Science, Inc. (Saco, Me.). Monoclonal mouse anti-human AFP antibody clone 2127435 (referred to as anti-AFP-435) were obtained from Fitzgerald Industries International (Concord, Mass.). Streptavidin-coated polystyrene/iron oxide beads with a mean diameter of 114 nm were purchased from Ademtech (Pessac, France).

Zeba spin filter columns and Starting Block were purchased from Pierce (Rockford, Ill.). Vivaspin molecular weight cutoff filters (both 50,000 and 5,000 Da MWCO), were from GE Healthcare (Waukesha, Wis.). Phosphate buffered saline (PBS, 10 mM phosphate ion concentration) was reconstituted from Dulbecco's phosphate buffered saline packets purchased from Sigma-Aldrich (St. Louis, Mo.). All other chemicals were obtained from Sigma-Aldrich and used as received.

Buffers were prepared with purified water (ELGA PURELAB filtration system; Lane End, UK), and the pH was adjusted with either 1 M HCl or 1 M NaOH. PBS buffer with 100 mM phosphate (100 mM PBS) was made with 150 mM NaCl, 22.5 mM monobasic sodium phosphate, and 77.7 mM dibasic sodium phosphate and pH-adjusted to either pH 7.4 or pH 6.0. PBS with tween (PBST, 0.05% Tween-20) was made by adding Tween-20 to standard PBS buffer (Dulbecco's formulation). All solutions were degassed via vacuum sonication before use.

The microring sensor chip for this experiment was first cleaned with piranha solution (3:1 $H_2SO_4$:30% $H_2O_2$) for 30 seconds followed by rinsing with water and $N_2$ drying. To introduce reactive functional groups, the chip was immersed in a 1 mg/mL solution of HyNic Silane (20 mg/mL HyNic Silane in DMF stock solution diluted to 1 mg/mL with ethanol) for 30 minutes, followed by rinsing with ethanol and then water.

Oligonucleotides were used to attach primary antibody to the surface and allow the beads to bind to the secondary antibodies. The surface bound antibody was attached via strands B and B' and the secondary antibody was functionalized with F' while the streptavidin beads were functionalized with biotinylated strand F.

All oligonucleotides were synthesized with a 5' amino terminal group to facilitate attachment to either the substrate or antibody, except for Strand F which had a terminal biotin group. Oligonucleotides were functionalized with S-4FB according to manufacturer (SoluLink) instructions. Briefly, oligonucleotides were buffer exchanged to 100 mM PBS pH 7.4 and then a 20-fold molar excess of S-4FB in DMF was added. Solutions were allowed to react overnight at room temperature and then were buffer exchanged into 100 mM PBS pH 6.0 using 5 kDa MWCO filters.

HyNic-silane-functionalized chips are DNA-functionalized by manually pulling a 0.5-μL drop of 4FB-modified strand B (at 150 μM) across the surface with a 2.5-μL pipette tip. For this experiment, 3 sensors in each channel were functionalized with strand B with the remaining sensors serving as controls. After spotting the DNA, the drops of solution were dried on a hot plate (~70° C.) and incubated in 80% relative humidity (or higher) for 1-2 hours to allow rehydration of the DNA on the surface. The chip was then immersed into S-4FB-modified Starting Block. The Starting Block was modified following the same procedure as oligonucleotide functionalization but 100 μL of 5 mg/mL S-4FB was added to 1.5 mL Starting Block. The blocking solution was removed by rinsing with water, and then additional S-4FB modified blocking solution was added to the chip before incubating overnight in a humidity chamber at 4° C. The sensor chip was then rinsed with water, and immersed in PBST until use.

To create DNA-antibody conjugates, antibodies were first functionalized with S-HyNic following the manufacturer's guidelines. Briefly, S-HyNic in DMF was added in 5-fold molar excess to ~1 mg/mL antibody that had previously been buffer exchanged into 100 mM PBS pH 7.4 with a Zeba spin filter and reacted for at least two hours at room temperature. The antibody was then exchanged into 100 mM PBS pH 6.0 and concentrated using a 50 kDa MWCO filter, which also served to remove residual S-HyNic. The 4FB-modified DNA was then added in 20-fold molar excess to the HyNic-modified antibody solution and allowed to react overnight at 4° C. DNA-antibody conjugates were then purified away from the excess DNA using a Superdex 200 10/300 GL column on an AKTA FPLC, both from GE Healthcare (Waukesha, Wis.). The separation was performed at 4° C. with a PBS isocratic elution. The collected fractions were concentrated with 50 kDa MWCO filters to yield purified solutions of DNA-antibody conjugates. The final conjugate concentration measured ~100 μg/mL, as determined by measuring the differential absorption at 260 versus 280 nm, corresponding to the DNA and IgG, respectively, using a NanoDrop UV-Vis absorbance system (Thermo-Fisher Scientific, Wilmington, Del.). The primary antibody was called B'-anti-AFP (B491M) and the secondary antibody was called F'-anti-AFP-435.

Streptavidin-coated, 100 nm beads were functionalized with strand F by first adding 16 uL of biotinylated strand F (~300 μM) to 50 μL of 5 mg/mL beads. Beads were then buffer exchanged to PBST via magnetic separation and resuspension. They were then diluted to 50 μg/mL prior to use.

The fluidic cell used for this experiment consisted of a 4-channel fluidic cell created by a 0.007-inch thick Mylar gasket topped with a polytetrafluoroethylene (PTFE) top to enable attachment to standard fluidic attachments. Solutions were pulled over the chip via 11 Plus syringe pump (from Harvard Apparatus; Holliston, Mass.) operated in withdraw mode. For this experiment, each channel had B'-anti-AFP (B491M) flowed over the chip until ~100 pm relative shift was observed on all sensors. Then 0.05, 0.5, 5, and 50 ng/mL AFP were flowed across the chip at 30 μL/min, each in a separate fluidic channel, for ~30 minutes. Following addition of AFP, 1 ug/mL F'-anti-AFP-435 was flowed across the chip for ~25 minutes. As a final step, 50 μg/mL 100 nm beads (functionalized with biotinylated strand F) were flowed over the surface for ~20 minutes.

Raw microring resonance wavelength data, recorded as a function of time, was corrected for any thermal drift of bulk refractive index shifts using on-chip control rings (exposed to solution, but not functionalized with DNA). The signal from all of the control rings was averaged and then subtracted from each of the individual active sensor rings. Results are shown in FIG. 24A-F.

Example 9

Multiplex Detection of Auto-Antibody Biomarkers of Auto-Immune Disorders

A multiplex chip was produced having silicon optical rings as described in Washburn et al., Analytical Chemistry, 2009. 81(22): p. 9499-9506 and Bailey, R. C. et al., Proceedings of SPIE—The International Society for Optical Engineering, 2009. Each optical ring was spotted with one of 5 antigens (Jo-1, Smith, SSA, SSB, and Scl-70), which are respectively associated with auto-immune diseases polymyositis (PM), systemic lupus erythematosis (SLE), Sjogren's Syndrome and SLE, Sjogren's Syndrome and SLE, and Sjogren's Syndrome.

Figure 25:
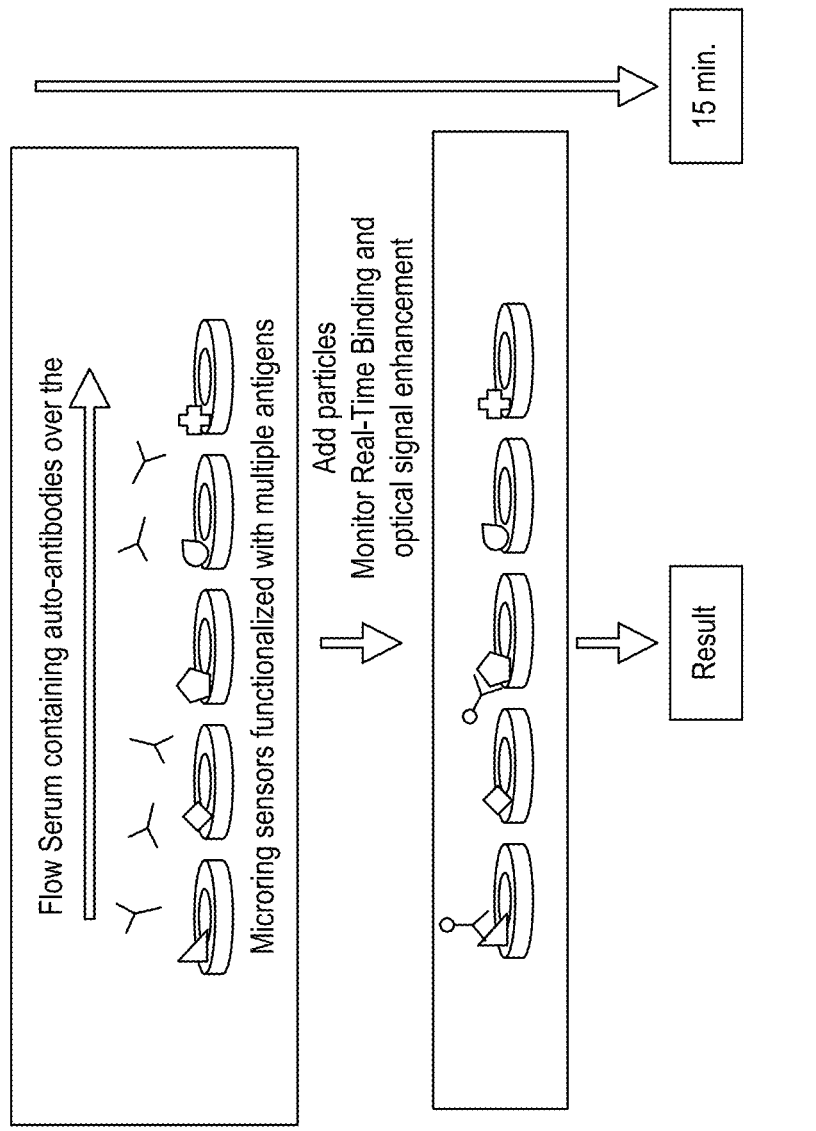
FIG. 25 is a schematic diagram of an auto-antibody multiplex optical ring detection system.
Figure 26B:
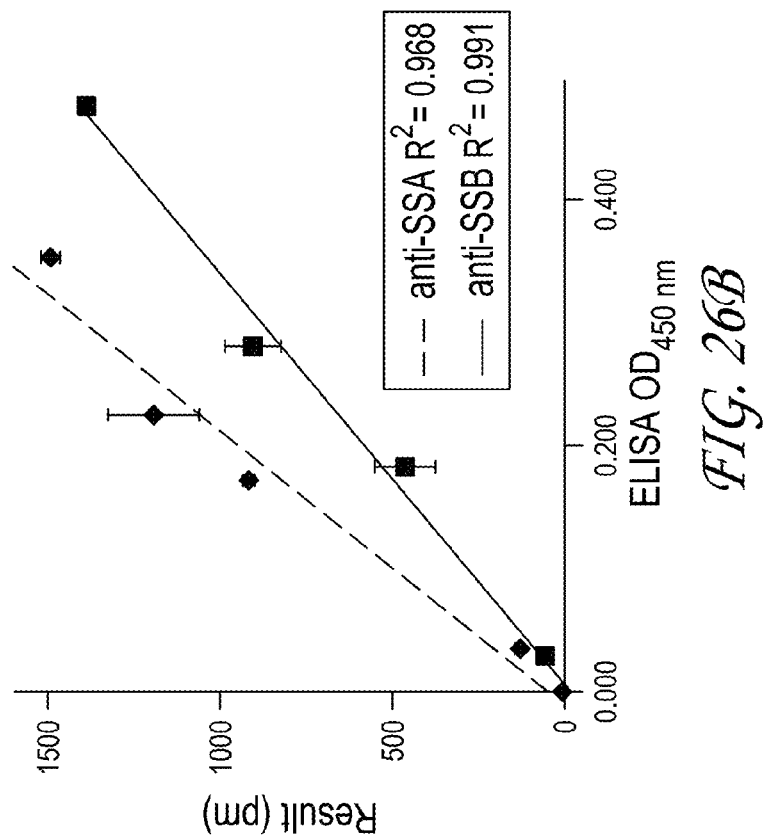
Figure 26A:
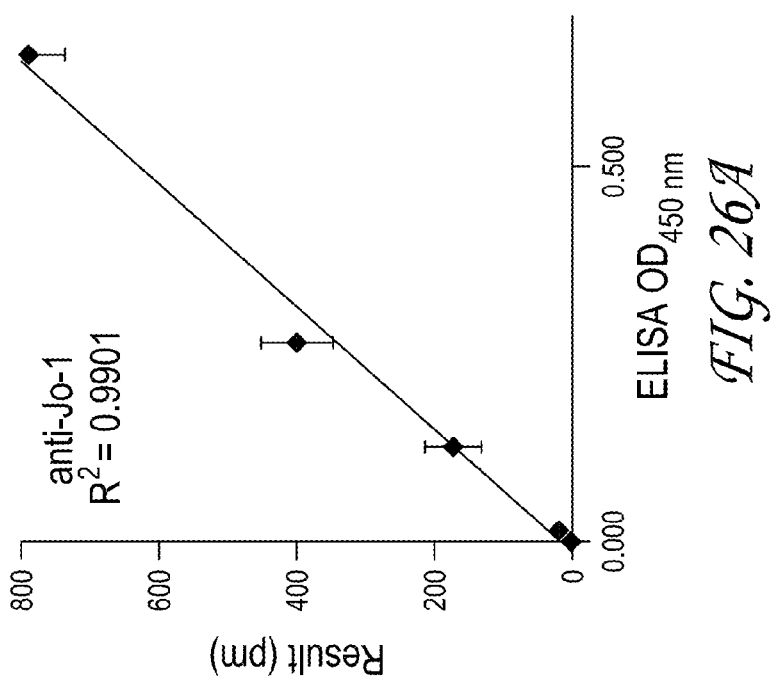

A serially diluted serum sample positive for all 5 antigens was tested on the multiplex chip and on a commercially available ELISA for comparison. First, the serum sample was flowed over the multiplex chip and auto-antibodies present in the serum were allowed to bind to the antigen capture probes. Subsequently, beads were flowed over the multiplex chip and allowed to bind to the auto-antibodies that previously bound to the antigen capture probes. Binding between the beads and auto-antibodies was detected and measured. A schematic of the workflow is shown in FIG. 25. As shown in FIG. 26, excellent correlation was observed for all analytes in the multiplex chip. The chip required only 2 µL, whereas ELISA required 50 µL sample volume. Real-time binding was observed and results were obtained within 15 minutes.

Figure 27:
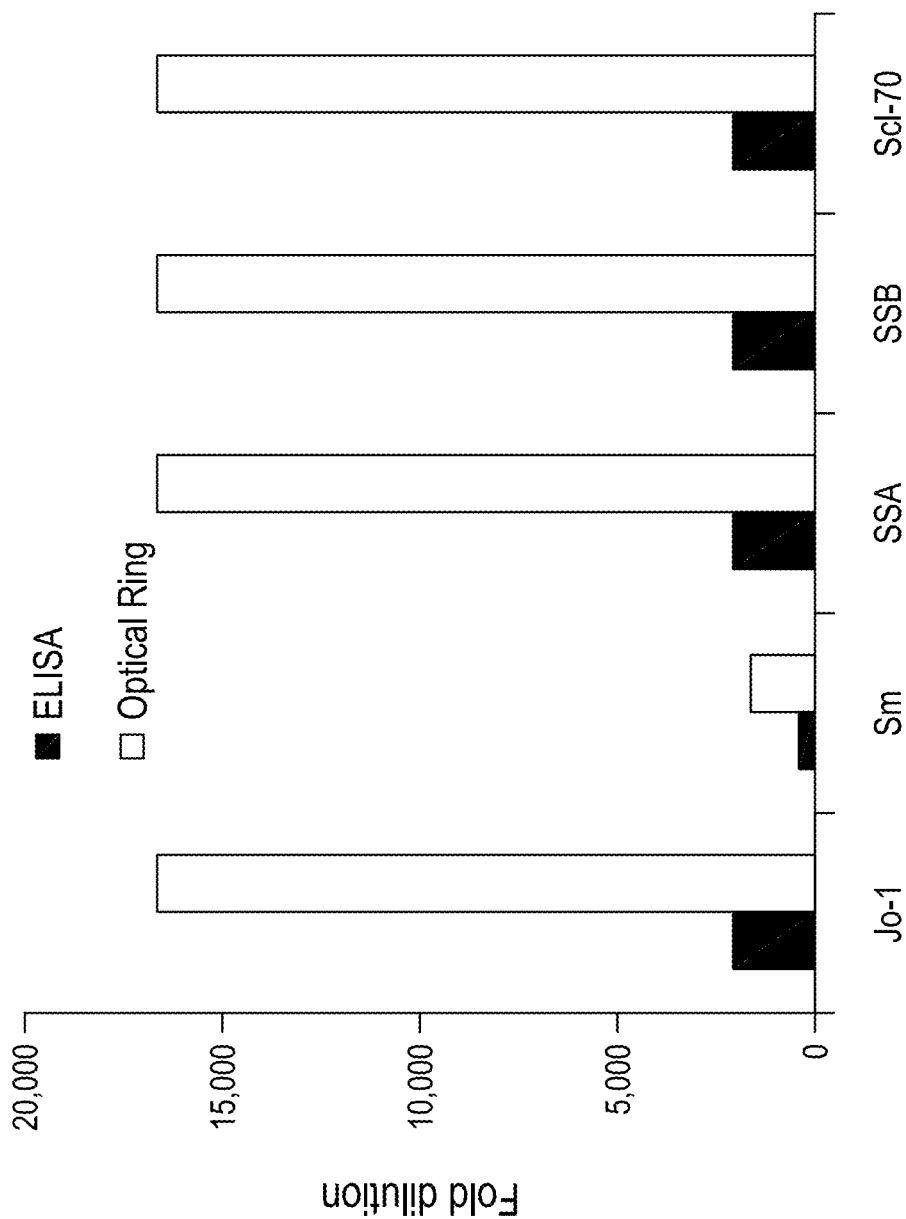
FIG. 27 is a bar graph comparing the sensitivity of the optical ring detection system compared to ELISA in detecting the auto-antibodies to Jo-1, SSA and SSB, Smith, and Scl-70.

As shown in FIG. 27, the multiplex chip was up to 10-fold more sensitive than ELISA at detecting the antigens in terms of dilution. A positive signal was detected at a 10-fold greater dilution with the multiplex chip as compared to ELISA.

Example 10

Cross-Talk Elimination in Multiplex Optical Detection Systems

Figure 28:
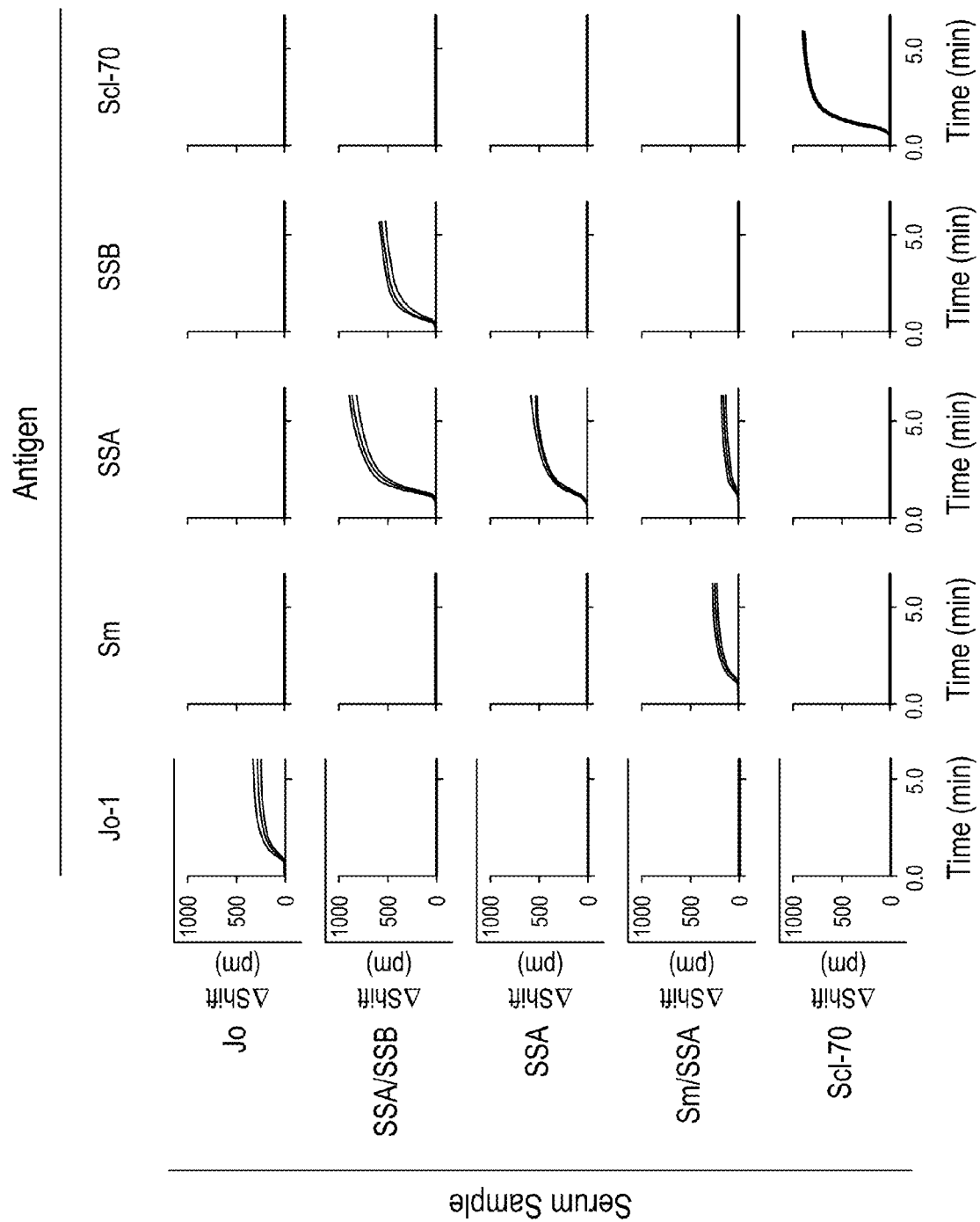
FIG. 28 is a panel of graphs plotting wavelength shift over time on 5 chips, each having a microring to detect one of the Jo-1, SSA and SSB, Smith, and Scl-70 auto-antibodies in control sera sample known to be positive for 1 or 2 of the autoantibodies. The results show no-cross talk between the microrings.

Control sera that were known to be positive for 1 or 2 auto-antibodies were tested at high concentrations to check for cross-talk on a multiplex chip having silicon optical rings, each functionalized with one of 5 antigens (Jo-1, Smith, SSA, SSB, and Scl-70). As shown in FIG. 28, no cross-talk was observed, as indicated by the observation that no more than two binding events were detected for each tested serum sample known to have 1 or 2 auto-antibodies.

Example 11

Result Reproducibility of Multiplex Optical Detection Systems

A sample known to be positive for all 5 antigens (Jo-1, Smith, SSA, SSB, and Scl-70) was run on a total of 5 chips, each chip as described in Examples 9 and 10. As shown in Table 6, the results observed were highly reproducible with a coefficient of variation (CV) less than 15%.

TABLE 6

| Antigen | Result (pm) | Standard Deviation | Coefficient of Variation (% CV) |
|---|---|---|---|
| Jo-1 | 113 | 14 | 12.5% |
| Smith | 201 | 22 | 10.8% |
| SSA | 654 | 83 | 12.7% |
| SSB | 201 | 25 | 12.4% |
| Scl-70 | 331 | 36 | 10.8% |

Imaging Based Scatter Detection System

As discussed above, sensitivity can be increased by using refractive index tags such as particles or beads in conjunction with the optical sensor 104. In various embodiments, analyte detection involves a binding event wherein a ring resonator 208 captures an analyte and a refractive index tag adheres to the captured analyte. The presence of the refractive index tag further increases the refractive index of the ring resonator beyond that induced by the presence of the analyte alone. The resonance wavelength is thereby shifted to a larger extent. Similarly, the dip in the spectral output 212 from the output waveguide 924 as measure by the apparatus 900 for interrogating the sensor chip shifts to a greater extent. The result is increased sensitivity in detection.

Another effect of the refractive index tag, such as a particle or bead, is to increase the scatter of light from the waveguide sensor. The presence of the bead in proximity to the waveguide sensor 104 (e.g., the ring resonator 208 and/or the waveguide 202 optically coupled thereto) may disrupt the confinement of the light propagating in the ring resonator 208 and/or the waveguide 202 optically coupled thereto and cause the light to scatter out of the waveguide. Some light may leak from the waveguide structure (e.g., ring resonator 208) even without the presence of a bead or other object in proximity to the optical sensor, and more light may be emitted from the resonator at wavelengths injected into the resonator that are at the resonance wavelength of the resonator. The presence of the bead or other object is in proximity to the optical sensor will enhance scattering at the resonance wavelength of the resonator. (Note that the bead or other object is in proximity to the optical sensor will shift the resonance wavelength as a result of the refractive index of the bead or other object). A binding event that brings a bead in close proximity to the sensor 104 could thus be detected by monitoring radiation exiting the ring resonator 208 and/or the waveguide 202 optically coupled thereto, for example, using a system that images the chip 902 such as the imaging system 930 shown in FIG. 9. Multiple sensors 104, e.g., the entire array of biosensors on a chip 902 could be monitored simultaneously; instead of sequentially measuring light coupled out of the different waveguide couplers 924. Additionally, output grating coupler 924 may not be necessary in some embodiments. In other embodiments, however, radiation exiting the ring resonator 208 and/or the waveguide 202 optically coupled thereto, can be monitored by scanning across the chip 902 and interrogating different optical sensors 104 using scanning mirrors 918 and signal collection optics 928 such as shown in FIG. 9. This later embodiment is discussed in connection with FIG. 29A.

Figure 29A:
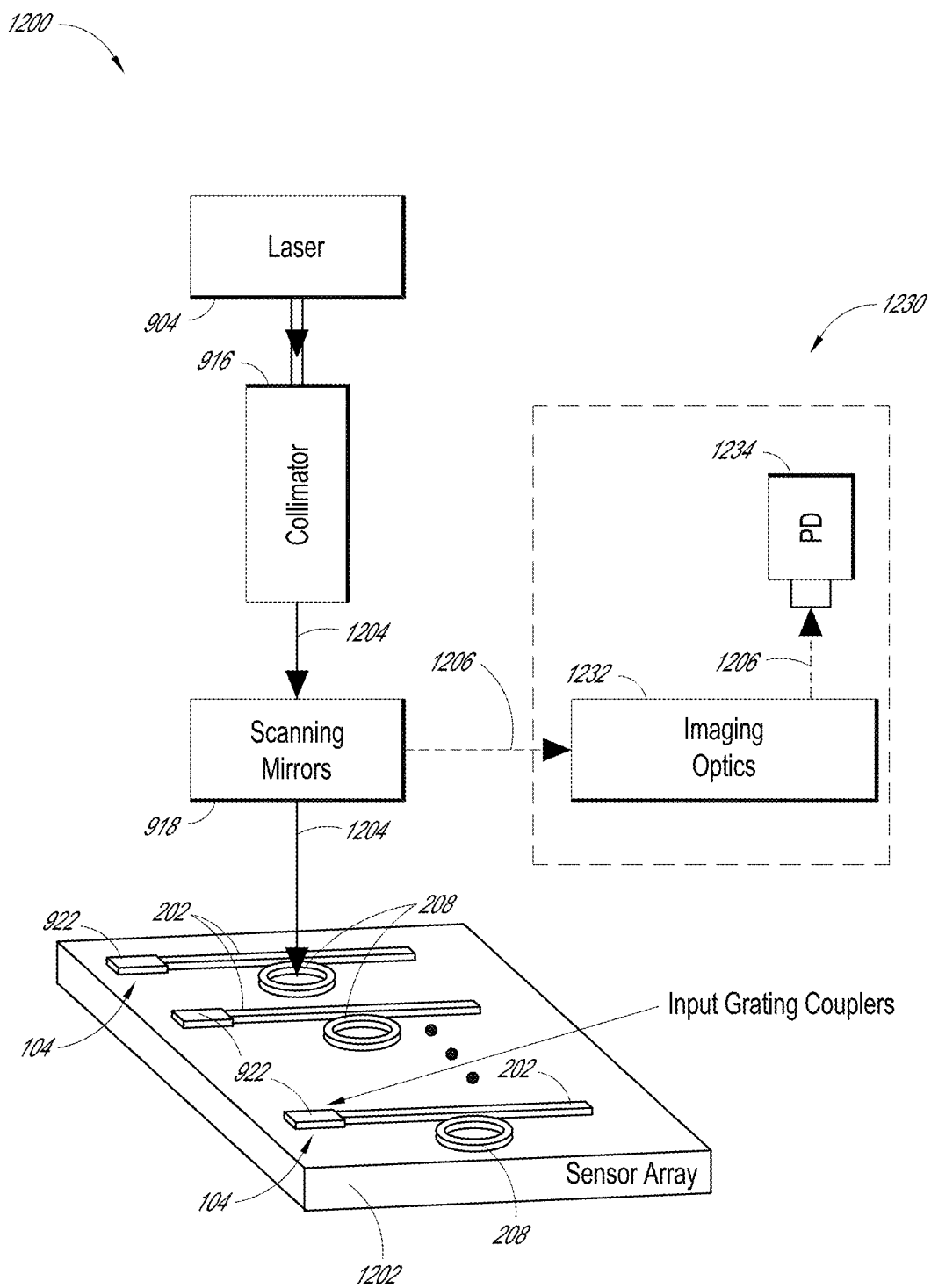
FIG. 29A schematically illustrates an apparatus for interrogating optical scattering from optical resonators on a chip by using scanning mirrors.

In particular, FIG. 29A shows an example apparatus 1200 for interrogating the optical sensors 104 on a chip 1202 by detecting scattering from individual optical resonators 208. The apparatus 1200 includes a laser light source 904, such as a tunable laser, for directing light onto the chip 1202. Beam shaping optics such as collimating optics 916, may be included in the first optical path 1204 (indicated by solid arrows) between the laser 904 and the chip 1202 to adjust the shape of the beam as desired. The apparatus 1200 further comprises one or more scanning mirrors 918 or other optical elements configured to selectively direct the beam to the appropriate location on the chip 1202.

The chip 1202 includes input couplers 922 configured to couple the beam propagating in free space into the waveguides 202 on the chip. As discussed above, these input couplers 922 may comprise, for example, waveguide gratings that use diffraction to couple the light beam propagating down toward the chip 1202 into optical modes that propagate along the waveguides 202 on the chip. The scanning mirrors 918 in the apparatus 1200 for interrogating the optical sensors 104 are moved such that the light is directed into the input grating coupler 922 of the optical sensor 104 to be interrogated.

As shown, the chip 1202 includes a plurality of optical sensors 104 each comprising linear waveguides 202 and ring resonators 208. Accordingly, light may be injected into the linear waveguides 202 via an input coupler 922 and propagated to the ring resonator 208. A binding event that brings a bead or other object in close proximity to the sensor 104 (e.g., the ring resonator 208 and/or the waveguide 202 optically coupled thereto) may disrupt the confinement of the light propagating in the ring resonator 208 and/or the waveguide 202 optically coupled thereto and cause the light to scatter out of the waveguide into free space along a path such as 1206 (indicated by dashed arrows) shown in FIG. 29A. This light could thus be detected by monitoring radiation exiting the optical sensor 104 using collection optics and a detector 1234. As discussed above, the scattering is greater for light having a wavelength corresponding to the resonance wavelength of the resonator. Additionally, the presence of the bead or other object in proximity to the optical sensor will shift this resonance.

In the embodiment shown in FIG. 29A, the focusing optics 920 can double as the collection optics. Alternatively, separate collection optics may used.

The apparatus 1200 in FIG. 29A also includes a detector 1234. The detector 1234 is disposed to receive light from the collection optics 920. In the particular embodiment shown, light from the chip 1202 propagates along second optical path 1206 through the collection optics 920 and propagates to the detector 1234 via the scanning mirrors 918 and the beam-splitter 926. Optional additional optics 1232, labeled imaging optics in FIG. 29A, may also be included as needed to couple the light to the detector 1234.

In some embodiments, the apparatus 1200 may be used in conjunction with an imaging system 1230 comprising the imaging optics 1232 and the image sensor 1234. Accordingly, the imaging system 1230 may be incorporated into the apparatus 1200 or it may be separate from the apparatus 1200. In some embodiments, the image sensor 1234 may comprise a detector array such as a CCD or CMOS detector array. The imaging system 1230 may be used to image the chip 1202 and facilitate identification of which optical sensor 104 is being interrogated at a given time. Imaging of the chip 1202 may be accomplished alternatively with a single detector as opposed to a detector array, as the scanning mirror 918 enables the detector's field of view to be scanned across the chip.

Accordingly, as the scanning mirror 918 scans the chip 1202, the detector 1234 can monitor increases in scattered light from the sensors 104. For example, if the field of view of the detector 1234 included an optical sensor 104 having a ring resonator 208 to which a bead is bound such that light propagating within that optical sensor 104 and in particular within that ring resonator 208 will be scattered into free space, this light can be detected by the detector 1234. As the scanning mirror 918 scans the chip 1202, optical sensors 104 from which light is emitted into free space will be identified and associated with a binding event. As described above, identification markers 1108 may be included on the chip 1202 and can be used to identify the optical sensors 104. In some embodiments, the imaging system 1230 is used to read the identification markers 1108. As described above, in some embodiments, input grating couplers 922 may be placed in a distinct pattern that allows the unique identification of each optical sensor 104. Accordingly, in such embodiments, separate identification markers 1108 need not be included on chip 1202. Other techniques can also be used for identifying the sensors 104.

Figure 29B:
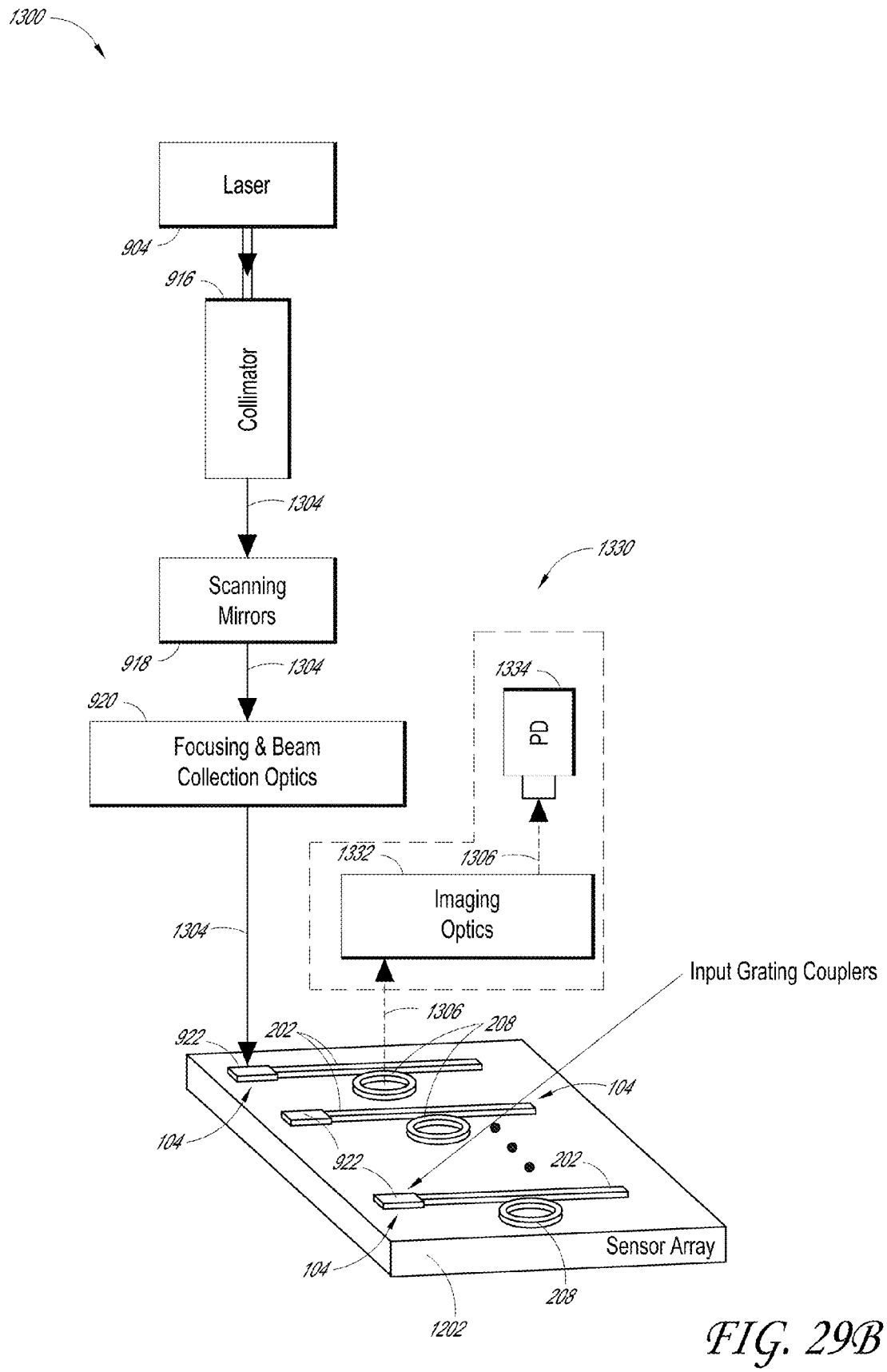
FIG. 29B schematically illustrates an apparatus for interrogating scattering from optical resonators on a chip by using imaging optics that form an image of a portion of the chip containing a plurality of such resonators onto a detector array.

Another embodiment of an apparatus 1300 for interrogating the optical sensors 104 on a chip 1202 is schematically illustrated in FIG. 29B. The apparatus 1300 includes a laser light source 904, scanning mirrors 918 (or other optical elements configured to selectively direct the beam to the appropriate location on the chip 1202), as well as focusing optics 920. The scanning mirrors 918 and focusing optics 920 are included in a first optical path 1304 (indicated by solid arrows) from the light source 904 to the chip 1202. The apparatus 1300 may also include beamshaping optics 916, which may be included along first optical path 1304.

In a manner as described in connection with FIG. 29A, light from the light source 904 is coupled into respective input grating couplers 922 of different optical sensors 104. In the case of a binding event wherein a bead or other object is in proximity to the optical sensor 104 so as to scatter light from the waveguide structure, light will be emitted into free space by the optical sensor.

FIG. 29B differs from FIG. 29A in the approach used to detect this light. An imaging system 1330 comprising imaging optics 1332 that forms an image of the chip 1202 onto a detector array 1334 is used to monitor light scattered from the optical sensors 104 by beads attached thereto. The imaging optics 1332 may comprise, for example, one or more lenses. In some embodiments, the detector array 1334 may comprise a CCD or CMOS detector array. As the lens 1332 forms an image of the chip 1202 on the detector array 1334, light emitted by optical sensors 104 on the chip 1202 will be observable by the detector array.

Although FIG. 29B shows light from a ring resonator 208 of an optical sensor 104 on the chip 1202 propagating through free space along a second optical path 1306 to the imaging system 1330, it should be noted that the imaging optics 1332 may form an image of a larger portion of the chip (possibly the entire chip or substantial portions thereof) onto the detector array 1334. The image formed may thus include scattered light from a plurality of optical sensors 104. Imaging a larger portion of the chip 1202 may facilitate identification of the particular sensors 104 from which light is scattered by the presence of a bead or other object.

As described above, identification markers 1108 on the chip 1202 can be also used to identify the sensors 104. In the embodiment shown in FIG. 29B, the identification markers may also be imaged onto the detector array 1334 by the imaging lens 1332. However, as described above, in some embodiments, input grating couplers 922 may be placed in a distinct pattern that allows the unique identification of each optical sensor 104. Accordingly, in such embodiments, separate identification markers 1108 need not be included on chip 1202. Other techniques can also be used for identifying the sensors 104.

Note that unlike the embodiment in FIG. 29A, the light from the optics sensors 104 does not pass back through the scanning mirrors 918 to reach the detector array 1334. In fact, in some embodiments, the imaging optics 1332 and detector array 1334 may be situated on the opposite side of the chip 1202 such that light is directed into grating couplers 922 on one side of the chip (e.g., above the chip) and scattered from the waveguide sensor 104 in many directions such that a portion is collected from a detector array 1334 located on the other side of the chip (below the chip) Likewise, the imaging system 1330 may be incorporated into the apparatus 1300 or it may be separate from the apparatus 1300.

Other variations are also possible. For example, instead of or in addition to the scanning mirrors 918 (such as shown in FIGS. 29A and/or 29B), actuators (e.g. motors such as stepper motors or piezoelectric devices) may be used to translate the chip 1202. Alternatively, instead of using scanning mirrors 918 to direct light into the waveguide structures, the chip 1202 could be illuminated with less focus, e.g., flood illumination.

Additionally, the optical spectrum of the light emitted from the resonators can be monitored. As discussed above, the bead or other object is in proximity to the resonator will enhance scattering at the resonance wavelength of the resonator. However, the bead or other object in proximity to the optical sensor will shift the resonance wavelength of the optical resonator as a result of the refractive index of the bead or other object. The light emitted from the resonator via scattering may thus have a spectral peak and that peak may be shifted as well as increased in magnitude with the binding event involving the bead or other object in proximity to the resonator. Monitoring the spectrum of emitted light may thus provide additional information.

In some embodiments, in addition to detecting the scatter from the optical sensors, e.g., ring resonators, output from output waveguides 924 such as shown in FIG. 9 (e.g., shift in the dip in the optical spectrum) can be monitored as described above to provide more information.

Still other variations are possible, for example, in some embodiments, the ring resonator 208 is excluded. For example, a particle coupled to the linear waveguide 202 can cause the light therein to be decoupled and scattered from the waveguide 202.

What is claimed is:

1. A system for detecting a polypeptide of interest in a sample comprising:
   an optical sensor that comprises a ring resonator;
   a plurality of first antibodies that specifically bind to the polypeptide of interest, wherein the first antibodies are attached to a surface of the ring resonator;
   a plurality of second antibodies that specifically bind to the polypeptide of interest;
   a plurality of particles attached to the second antibodies or particles capable of binding the second antibodies; and
   a detector,
   wherein said optical sensor has a resonant wavelength that is shifted when said second antibodies are bound to said polypeptide of interest bound to said first antibodies, such that said optical sensor is configured to sense said second antibodies combined with said polypeptide bound to said first antibodies, and the particles amplify the shift of the resonant wavelength, and
   wherein the detector is configured to determine the concentration of the polypeptide in the sample based on the shift of the resonant wavelength resulting from multiple bound particles at the ring resonator.

2. A system for detecting a polypeptide of interest in a sample comprising:
   an optical sensor that comprises a ring resonator configured to resonate at a resonant wavelength;
   a tunable laser capable of providing light at said resonant wavelength for the optical sensor;
   a plurality of first antibodies that specifically bind to the polypeptide of interest, wherein the first antibodies are attached to a surface of the ring resonator;
   a plurality of second antibodies that specifically bind to the polypeptide of interest;
   a plurality of particles attached to the second antibodies or particles capable of binding the second antibodies; and
   a detector,
   wherein said optical sensor has a resonant wavelength that is shifted when said second antibodies bind to said polypeptide bound to said first antibodies such that said optical sensor is configured to sense said second antibodies combined with said polypeptide bound to the first antibodies;
   wherein the particle amplifies the shift of the resonant wavelength;
   wherein the detector is capable of detecting the shifted resonant wavelength, and
   wherein the detector is configured to determine the concentration of the polypeptide in the sample based on the shift of the resonant wavelength resulting from multiple bound particles at the ring resonator.

3. A system for detecting an analyte of interest in a sample comprising:
   an optical sensor that comprises a ring resonator;
   a plurality of capture probes attached to a surface of the ring resonator, wherein the capture probes are capable of binding to the analyte;
   a plurality of antibodies capable of specifically binding to the analyte or a plurality of complexes formed between the analyte and the capture probes;
   a plurality of particles attached to the antibodies or capable of binding to the antibodies; and
   a detector,
   wherein said optical sensor has a resonant wavelength that is shifted by said antibodies bound to said complexes or analyte bound to the capture probes, such that said optical sensor is configured to sense said antibodies combined with said analyte or complexes, and the particles amplify the shift of the resonant wavelength, and
   wherein the detector is configured to determine the concentration of the analyte in the sample based on the shift of the resonant wavelength resulting from multiple bound particles at the ring resonator.

4. The system of claim 3, wherein the particles comprise a bead, polypeptide, nanoparticle, semiconductor crystal, titanium-oxide crystal, or quantum dot.

5. The system of claim 3, wherein the particles comprise an average diameter of at least 1 nm.

6. The system of claim 4, wherein the bead comprises silicon, polystyrene, agarose, sepharose, metal, or metal-oxide.

7. The system of claim 3, wherein the particles comprise a polypeptide of at least 200 Daltons (Da).

8. The system of claim 3, wherein the analyte is a polypeptide.

9. The system of claim 8, wherein the capture probes comprise an antibody that specifically binds to the polypeptide, an aptamer that specifically binds to the polypeptide, or a protein that specifically binds to the polypeptide.

10. The system of claim 3, wherein the analyte is a nucleic acid.

11. The system of claim 10, wherein the nucleic acid comprises ribonucleic acid (RNA).

12. The system of claim 10, wherein the capture probes comprise a DNA oligonucleotide.

13. The system of claim 3, wherein the optical sensor comprises a silicon waveguide structure.

14. The system of claim 13, wherein the optical sensor has an output portion configured to output an optical signal, and wherein the optical output yields different outputs when said capture probe binds to the analyte of interest forming said complex and said antibody binds said complex, and when said antibody does not bind to said complex.

15. The system of claim 3, wherein the ring resonator comprises an input portion and an output portion, and wherein the optical sensor further comprises an input waveguide and an output waveguide having the ring resonator therebetween configured to increase coupling of said light from said input waveguide to said output waveguide when said capture probes bind to the analyte of interest forming said complexes and said antibodies bind to said complexes.

16. The system of claim 3, wherein said optical sensor is integrated on an integrated optical chip comprising optical waveguides.

17. A method for detecting a polypeptide of interest in a sample comprising:
providing an optical sensor that comprises a ring resonator, the optical sensor comprising a plurality of first antibodies attached to a surface of the ring resonator, wherein the first antibodies specifically bind to the polypeptide of interest;
applying a sample for which the presence or absence of the polypeptide of interest is to be determined to the optical sensor, under conditions in which the polypeptide of interest, when present, and the first antibodies bind;
providing a plurality of second antibodies that specifically bind the polypeptide of interest, wherein binding between the second antibodies and the polypeptide of interest, when bound to the first antibodies, shifts a resonant wavelength of the optical sensor;
providing a plurality of particles attached to the second antibodies or particles capable of binding the second antibodies, wherein the particles amplify the shift of the resonant wavelength; and
determining the concentration of the polypeptide of interest in the sample based on the shift of the resonant wavelength resulting from multiple bound particles at the ring resonator.

18. The method of claim 17, wherein said ring resonator comprises a waveguide structure.

19. A method for detecting an analyte of interest in a sample comprising:
providing an optical sensor that comprises a ring resonator, the optical sensor comprising a plurality of capture probes attached to a surface of the ring resonator, wherein the capture probes are capable of binding to the analyte of interest to form complexes;
applying a sample for which the presence or absence of the analyte of interest is to be determined to the optical sensor, under conditions in which the analyte of interest, when present, and the capture probes bind to form the complexes;
providing plurality of antibodies that specifically bind to the complexes or analyte, wherein binding between the antibodies and the complexes or the analyte, when the analyte is bound to the capture probes, shifts a resonant wavelength of the optical sensor;
providing a plurality of particles attached to the antibodies or particles capable of binding the antibodies, wherein the particles amplify the shift of the resonant wavelength; and
determining the concentration of the analyte of interest in the sample based on the shift of the resonant wavelength resulting from multiple bound particles at the ring resonator.

20. The method of claim 19, wherein the analyte of interest comprises ribonucleic acid (RNA).

21. The method of claim 19, wherein said ring resonator comprises a waveguide structure.

* * * * *